United States Patent
Ji et al.

(10) Patent No.: US 9,241,991 B2
(45) Date of Patent: Jan. 26, 2016

(54) AGENTS, COMPOSITIONS, AND METHODS FOR TREATING PRURITUS AND RELATED SKIN CONDITIONS

(75) Inventors: Ru-Rong Ji, Medford, MA (US); Temugin Berta, Boston, MA (US); Zhen-Zhong Xu, Malden, MA (US); Tong Liu, Jamaica Plain, MA (US); Chul-Kyu Park, Chestnut Hill, MA (US)

(73) Assignee: The Brigham and Women's Hospital, Inc., Boston, MA (US)

(*) Notice: Subject to any disclaimer, the term of this patent is extended or adjusted under 35 U.S.C. 154(b) by 195 days.

(21) Appl. No.: 13/878,478

(22) PCT Filed: Oct. 21, 2011

(86) PCT No.: PCT/US2011/057336
§ 371 (c)(1),
(2), (4) Date: Jun. 24, 2013

(87) PCT Pub. No.: WO2012/054862
PCT Pub. Date: Apr. 26, 2012

(65) Prior Publication Data
US 2013/0266588 A1    Oct. 10, 2013

Related U.S. Application Data

(60) Provisional application No. 61/405,452, filed on Oct. 21, 2010.

(51) Int. Cl.
| | |
|---|---|
| A61K 39/395 | (2006.01) |
| A61K 31/4706 | (2006.01) |
| A61K 31/713 | (2006.01) |
| A61K 31/165 | (2006.01) |
| A61K 31/417 | (2006.01) |
| A61K 45/06 | (2006.01) |

(52) U.S. Cl.
CPC ........... *A61K 39/3955* (2013.01); *A61K 31/165* (2013.01); *A61K 31/417* (2013.01); *A61K 31/4706* (2013.01); *A61K 31/713* (2013.01); *A61K 45/06* (2013.01)

(58) Field of Classification Search
None
See application file for complete search history.

(56) References Cited

PUBLICATIONS

Liu et al; The Journal of Clinical Investigation; 2012; vol. 122; No. 6, pp. 2195-2207.*
Liu et al; Nature Neuroscience, 2010; vol. 13, No. 12, pp. 1460-1462.*
International Search Report and Written Opinion mailed on May 24, 2012 in International Application No. PCT/US2011/057336, 5 pages.

* cited by examiner

*Primary Examiner* — Bridget E Bunner
*Assistant Examiner* — Fozia Hamud
(74) *Attorney, Agent, or Firm* — Fish & Richardson P.C.

(57) ABSTRACT

This invention relates generally to a therapeutic use of TLR3 and TLR7 inhibitors to treat or reduce pruritus in a subject.

20 Claims, 20 Drawing Sheets

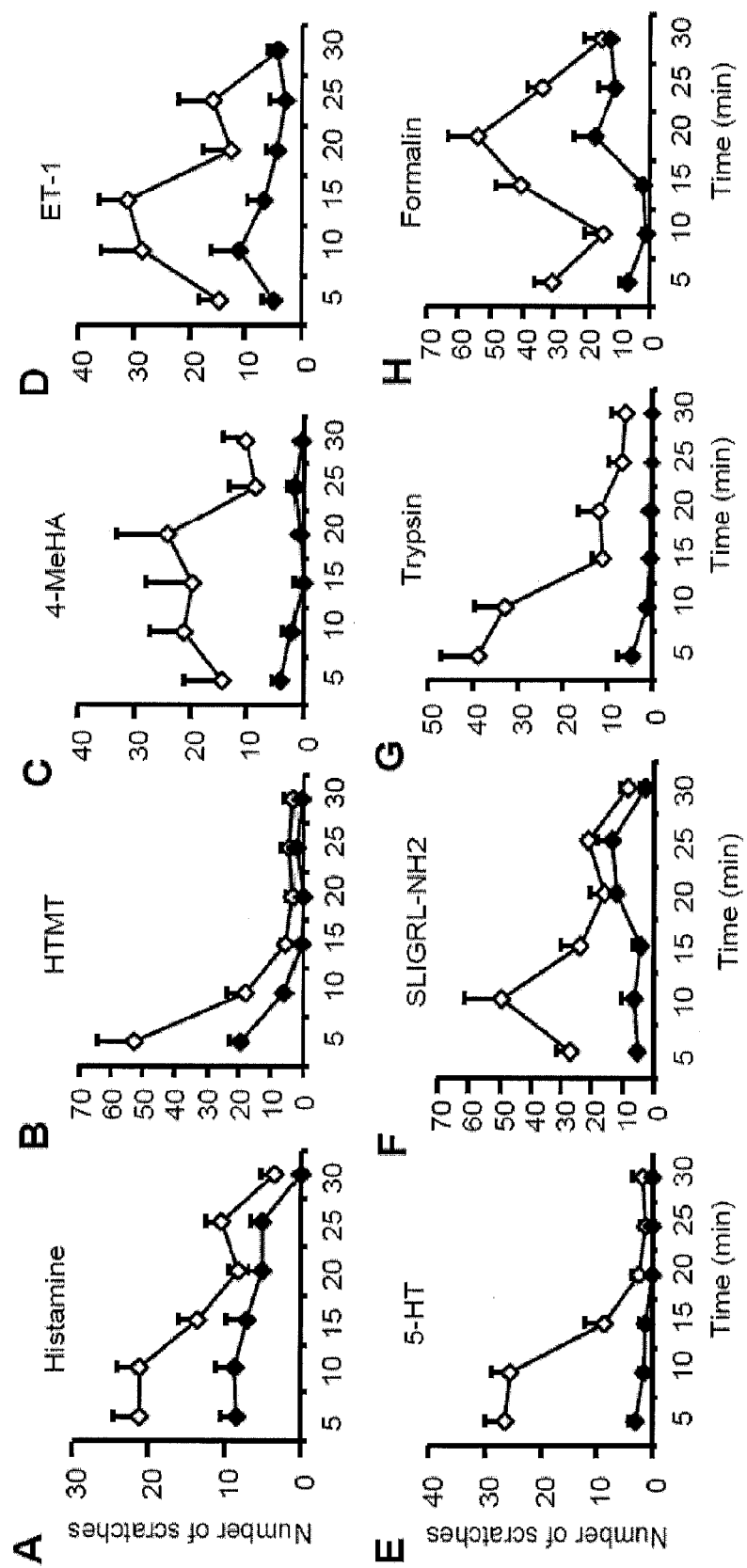
FIGs. 9A-H

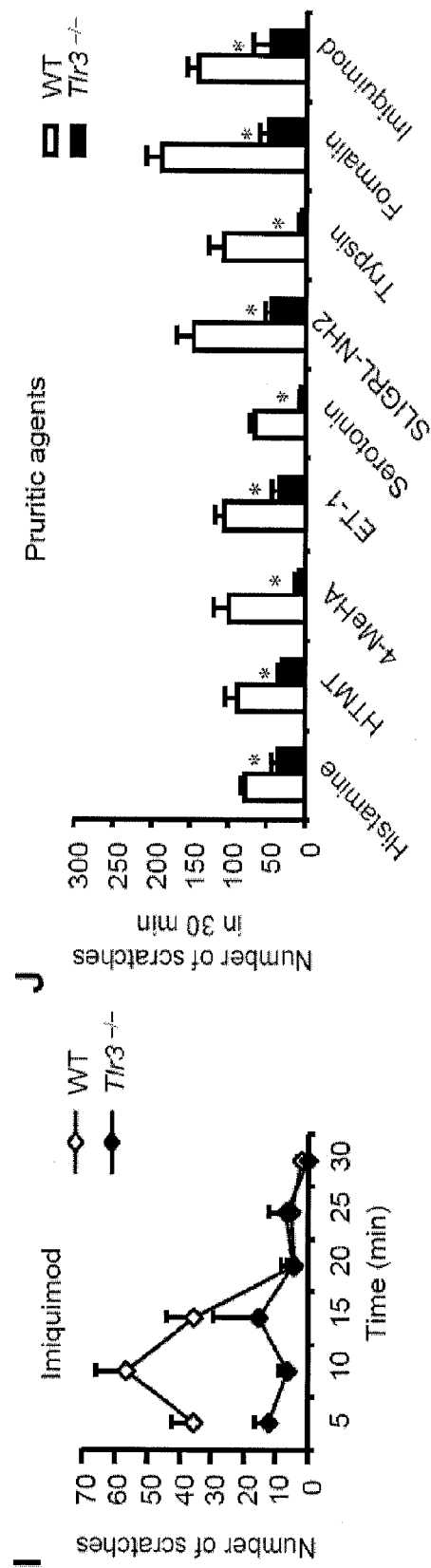
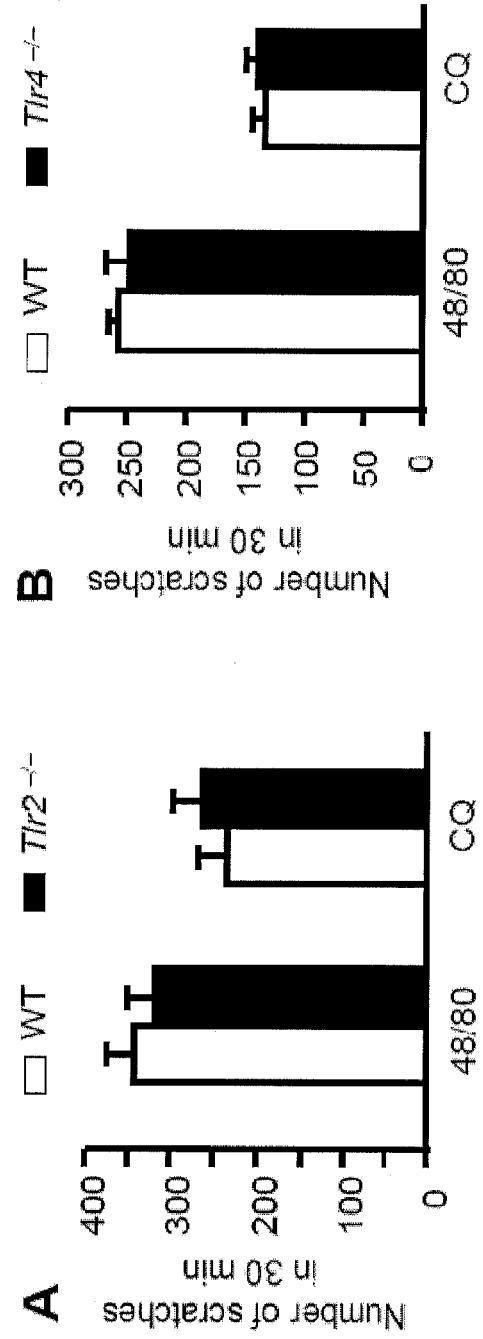
FIGs. 9I and 9J
FIGs. 10A and 10B

```
                              SEQUENCE LISTING

<160> NUMBER OF SEQ ID NOS: 63

<210> SEQ ID NO 1
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1
aacaattgct tcaagtcc                                                       18

<210> SEQ ID NO 2
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 2
actactacac tagactac                                                       18

<210> SEQ ID NO 3
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 3
ctctgatggc tttggctact                                                     20

<210> SEQ ID NO 4
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 4
gatgttgaac aggaagtcgg                                                     20

<210> SEQ ID NO 5
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 5
gaagggtgga gccaaaagg                                                      19

<210> SEQ ID NO 6
<211> LENGTH: 20
<212> TYPE: DNA
<213> ORGANISM: Artificial Sequence
<220> FEATURE:
<223> OTHER INFORMATION: Description of Artificial Sequence: Synthetic
      primer
```

-continued

```
<400> SEQUENCE: 6
aaggtggaag agtgggagtt                                              20

<210> SEQ ID NO 7
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 7
tgtaatacga ctcactatag ggcg                                         24

<210> SEQ ID NO 8
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 8
ccuuacacua uuuccgaua                                               19

<210> SEQ ID NO 9
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 9
uagcgacuaa acacaucaau u                                            21

<210> SEQ ID NO 10
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 10
tgatcatctt caccacggct g                                            21

<210> SEQ ID NO 11
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 11
ccttgcgatg gctgaagtac a                                            21

<210> SEQ ID NO 12
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 12
```
ccaaggagca aaacaaaacc c                                           21

<210> SEQ ID NO 13
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 13
gcaaattgga gccctgaatc t                                           21

<210> SEQ ID NO 14
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 14
agcctcgtcc cgtagacaaa a                                           21

<210> SEQ ID NO 15
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 15
ttttggctcc accccttca                                              19

<210> SEQ ID NO 16
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 16
tcttggaatg tcaccaggct g                                           21

<210> SEQ ID NO 17
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 17
tcgctccgta cgaagttctc a                                           21

<210> SEQ ID NO 18
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 18
ccagttcctt tgcattggtc c					21

<210> SEQ ID NO 19
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 19
gcccgaaaac atccttctca a					21

<210> SEQ ID NO 20
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 20
gtgtagccat tgctgccaac a					21

<210> SEQ ID NO 21
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 21
ggtccaagtt gccgtttctt g					21

<210> SEQ ID NO 22
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 22
cagtgaactc tggccgttga ga				22

<210> SEQ ID NO 23
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 23
tggcggcata ccctcaaaa					19

<210> SEQ ID NO 24
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 24
aaggcttgcc cccctataa					19

<210> SEQ ID NO 25
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 25
caccagcatg aacagtgact gt                                              22

<210> SEQ ID NO 26
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 26
agactgcctt ctgcaaacgt c                                               21

<210> SEQ ID NO 27
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 27
aagcctagct ggaaaaagcg                                                 20

<210> SEQ ID NO 28
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 28
tgaaggtcgg tgtgaacgaa tt                                              22

<210> SEQ ID NO 29
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 29
gctttctcca tggtggtgaa ga                                              22

<210> SEQ ID NO 30
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 30
tgtgcccttc tcctgttgat ct                                              22

<210> SEQ ID NO 31
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 31
gttttgtggc tcttttcgat gg                                            22

<210> SEQ ID NO 32
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 32
cagccttcaa agactgatgc tc                                            22

<210> SEQ ID NO 33
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 33
gatttcatct aagccgttgg ac                                            22

<210> SEQ ID NO 34
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 34
tcatccagga aggcttcca                                                19

<210> SEQ ID NO 35
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 35
ttcgaggctt ttccatcca                                                19

<210> SEQ ID NO 36
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 36
ttctccaaca accggcttga t                                             21

```
<210> SEQ ID NO 37
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 37
tcaggaggca aggaattcag g                                              21

<210> SEQ ID NO 38
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 38
tccatgacaa ctttggcatt g                                              21

<210> SEQ ID NO 39
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 39
acaacttacc gaaacctcag a                                              21

<210> SEQ ID NO 40
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 40
gcgttgcgaa gtgaagaact                                                20

<210> SEQ ID NO 41
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 41
ttcagaactt cagtggctgg                                                20

<210> SEQ ID NO 42
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 42
tttgtctctt ccgtgtccac                                                20

<210> SEQ ID NO 43
```

<211> LENGTH: 24
<212> TYPE: DNA
<213> ORGANISM: Artificial Sequence
<220> FEATURE:
<223> OTHER INFORMATION: Description of Artificial Sequence: Synthetic primer

<400> SEQUENCE: 43
atgttcgtct acctcgtgtt cttg                                          24

<210> SEQ ID NO 44
<211> LENGTH: 20
<212> TYPE: DNA
<213> ORGANISM: Artificial Sequence
<220> FEATURE:
<223> OTHER INFORMATION: Description of Artificial Sequence: Synthetic primer

<400> SEQUENCE: 44 aggctctttta tggacatggc                                              20

<210> SEQ ID NO 45
<211> LENGTH: 20
<212> TYPE: DNA
<213> ORGANISM: Artificial Sequence
<220> FEATURE:
<223> OTHER INFORMATION: Description of Artificial Sequence: Synthetic primer

<400> SEQUENCE: 45
ccccaaaggg atgagaagtt                                               20

<210> SEQ ID NO 46
<211> LENGTH: 22
<212> TYPE: DNA
<213> ORGANISM: Artificial Sequence
<220> FEATURE:
<223> OTHER INFORMATION: Description of Artificial Sequence: Synthetic primer

<400> SEQUENCE: 46
cccaataaag gttttgccaa gg                                            22

<210> SEQ ID NO 47
<211> LENGTH: 22
<212> TYPE: DNA
<213> ORGANISM: Artificial Sequence
<220> FEATURE:
<223> OTHER INFORMATION: Description of Artificial Sequence: Synthetic primer

<400> SEQUENCE: 47
atttctgact atgtccaccc tg                                            22

<210> SEQ ID NO 48
<211> LENGTH: 22
<212> TYPE: DNA
<213> ORGANISM: Artificial Sequence
<220> FEATURE:
<223> OTHER INFORMATION: Description of Artificial Sequence: Synthetic primer

<400> SEQUENCE: 48
cacttctgag aactacctgt cg                                            22

<210> SEQ ID NO 49
<211> LENGTH: 21

```
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 49
tgtggctaaa gatgaaccct c                                              21

<210> SEQ ID NO 50
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 50
cagtcttctg ggtggcagtg a                                              21

<210> SEQ ID NO 51
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 51
accccagaag catcacatg                                                 19

<210> SEQ ID NO 52
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 52
ttcaagagga gggcgaataa                                                20

<210> SEQ ID NO 53
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 53
tgttagtcca gagaaacttc ctg                                            23

<210> SEQ ID NO 54
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 54
gatgtccttg gctcccttt c                                               20

<210> SEQ ID NO 55
<211> LENGTH: 25
<212> TYPE: DNA
```

```
<213> ORGANISM: Artificial Sequence
<220> FEATURE:
<223> OTHER INFORMATION: Description of Artificial Sequence: Synthetic
      primer

<400> SEQUENCE: 55
aggcagtgag ttattcttcc catcc                                              25

<210> SEQ ID NO 56
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 56
tctttcgtag ttctgcatcg c                                                  21

<210> SEQ ID NO 57
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 57
cacttggtgg tttgctacga                                                    20

<210> SEQ ID NO 58
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 58
ttgctatctg tgtacggttc tg                                                 22

<210> SEQ ID NO 59
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 59
aatgggaact tgcacctcc                                                     19

<210> SEQ ID NO 60
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 60
tgttttgtta tgggctccta gg                                                 22

<210> SEQ ID NO 61
<211> LENGTH: 21
<212> TYPE: DNA
<213> ORGANISM: Artificial Sequence
```

-continued

```
<220> FEATURE:
<223> OTHER INFORMATION: Description of Artificial Sequence: Synthetic
      primer

<400> SEQUENCE: 61
acactccaga atcgtcaact c                                                    21

<210> SEQ ID NO 62
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: c-term amidated

<400> SEQUENCE: 62

Ser Leu Ile Gly Arg Leu
1               5

<210> SEQ ID NO 63
<211> LENGTH: 18
<212> TYPE: DNA
<213> ORGANISM: Artificial Sequence
<220> FEATURE:
<223> OTHER INFORMATION: Description of Artificial Sequence: Synthetic
      primer
<220> FEATURE:
<221> NAME/KEY: misc_feature
<222> LOCATION: (1)..(18)
<223> OTHER INFORMATION: This sequence may be 12-18 nucleotides in
      length

<400> SEQUENCE: 63
tttttttttt tttttttt                                                        18
```

AGENTS, COMPOSITIONS, AND METHODS FOR TREATING PRURITUS AND RELATED SKIN CONDITIONS

CLAIM OF PRIORITY

This application is a U.S. National Phase Application under 35 U.S.C. §371 of International Patent Application No. PCT/US2011/057336, filed Oct. 21, 2011, which claims the benefit of U.S. Provisional Application Ser. No. 61/405,452, filed on Oct. 21, 2010, all of which are incorporated herein by reference in their entireties.

FEDERALLY SPONSORED RESEARCH OR DEVELOPMENT

This invention was made with government support under grant nos. R01-DE17794, R01-NS54932, and R01-NS67686 awarded by the National Institutes of Health. The government has certain rights in the invention.

TECHNICAL FIELD

This disclosure relates to methods of treating pruritus by administering compositions comprising Toll-like receptor (TLR) 3 or TLR7 inhibitors.

BACKGROUND

Itch, or pruritus, is an unpleasant cutaneous sensation that evokes scratching behavior, which is distinct from pain that elicits withdrawal reflex of affected body (1). Like pain, itch serves as a self-protective and warning system in normal conditions (1). Under pathological conditions, such as dermatitis, liver or kidney diseases and metabolic disorders, itch becomes persistent, recurrent and intractable (2-5). Although itch is transiently relieved by scratching, itch-scratch cycles often results in further skin damage that exacerbates the problem (6). Antihistamines are normally used for itch relief, but many chronic itchy conditions are resistant to antihistamine treatment (7).

Although itch and pain share many similarities (1; 7; 8), increasing evidence points to distinct molecular mechanisms of itch (9-12). Primary sensory neurons located in trigeminal ganglion and dorsal root ganglion (DRG) are responsible for transducing itch stimuli to the central nervous system (1; 7). As the best-characterized itch mediator, histamine is released from mast cells and binds H1/H4 receptors on skin nerve terminals to elicit itch (13), via activation the PLCbeta3 and transient receptor potential subtype V1 (TRPV1)(14-16). Chloroquine, an anti-malaria drug and also an agonist of sensory neuron-specific G-protein-coupled receptor (GPCR) MrgprA3 and BAMS-22, an endogenous agonist of MrgprC11, can produce histamine-independent itch, in a TRPA1-dependent manner (11; 17). Both histamine-dependent and independent itch require the TRPV1-expressing nociceptors (15; 18). Recent studies showed that loss of vesicular glutamate transporter-2 (vGLUT2) in nociceptors lead to reduced pain but enhanced itch, indicating that glutamate release from these nociceptors is dispensable for signaling itch (19; 20). At the spinal cord level, gastrin releasing peptide (GRP), released from TRPV1-expressing nociceptors, activate GRP receptor (GRPR)-expressing neurons in the laminae I-II to elicit itching sensation (9; 10). Moreover, loss of Bhlhb5-expressing inhibitory interneurons in the spinal cord results in enhanced itch, providing evidence of central sensitization-initiated itch (21).

SUMMARY

The present invention is based, at least in part, on the discovery that TLR3 and TLR7 signaling plays a role in itch. Thus, inhibitors of TLR3 and or TLR7 can be used to reduce itching in subjects suffering from itch, e.g., pruritus associated with dermatitis, liver or kidney diseases and metabolic disorders.

In one aspect, the invention features methods of reducing or inhibiting pruritus in a subject. The methods can include administering to a subject a therapeutically effective amount of a TLR3 or TLR7 inhibitor, thereby reducing or inhibiting pruritus in the subject.

TLR3 inhibitors can include anti-TLR3 antibodies or antigen-binding fragments thereof, inhibitory nucleic acids effective to specifically reduce expression of TLR3, e.g., small interfering RNA molecules or antisense nucleic acids, or small molecules.

TLR7 inhibitors can include anti-TLR7 antibodies or antigen-binding fragments thereof, inhibitory nucleic acids effective to specifically reduce expression of TLR7, e.g., small interfering RNA molecules or antisense nucleic acids, or small molecules.

In some embodiments, the subject has, or is at risk of developing, pruritus.

In one embodiment, the subject has atopic dermatitis, psoriasis, renal disease, or liver disease.

In some embodiments, the subject is infected with a virus, e.g., human immunodeficiency virus or varicella zoster virus.

In one embodiment, the subject is being treated with a drug that causes pruritus, e.g., anti-malarials (chloroquine, amodiaquine, halofantrine and hydroxychloroquine); opioids (e.g., morphine, sufentanil, fentanyl, or butorphanol); glimepride; hydroxyethyl starch; or other drugs, e.g., those listed in Reich et al., Acta Derm Venereol. 2009; 89(3):236-44, e.g., in Table I, II, or III thereof (which is incorporated herein by reference in its entirety).

In some embodiments, the subject is a black African, e.g., being treated with chloroquine.

In one embodiment, the subject is a mammal, e.g, a human, dog, cat, pig, cow, or horse.

In some embodiments, administration is topical. In some embodiments, administration is systemic (e.g., oral or parenteral).

As used herein, the term "TLR3/7" means "TLR3 and/or TLR7".

Unless otherwise defined, all technical and scientific terms used herein have the same meaning as commonly understood by one of ordinary skill in the art to which this invention belongs. Methods and materials are described herein for use in the present invention; other, suitable methods and materials known in the art can also be used. The materials, methods, and examples are illustrative only and not intended to be limiting. All publications, patent applications, patents, sequences, database entries, and other references mentioned herein are incorporated by reference in their entirety. In case of conflict, the present specification, including definitions, will control.

Other features and advantages of the invention will be apparent from the following detailed description and figures, and from the claims.

DESCRIPTION OF DRAWINGS

FIG. 1A is a bar graph showing thermal sensitivity measured by tail-flick latency in hot water is comparable between groups (P>0.05). FIG. 1B is a bar graph showing Mechanical sensitivity assessed by tail withdrawal threshold in Randall-Selitto test is indistinguishable between groups (P>0.05). FIGS. 1C and 1D are bar graphs showing acute spontaneous pain assessed by the number of flinches or duration of licking and flinching behavior following intraplantar injection of capsaicin (FIG. 1C) and mustard oil (FIG. 1D) is comparable between groups (P>0.05). FIG. 1E is a bar graph showing motor function assessed by recording the falling latency in Rotarod test was normal in Tlr3$^{-/-}$ mice (P>0.05). FIG. 1F is a line graph showing spontaneous pain responses in the second-phase (10 to 45 minutes), but not in the first-phase (0 to 10 minutes) in the formalin test is decreased in Tlr3$^{-/-}$ mice. FIG. 1G is a series of two line graphs showing primary and secondary mechanical hypersensitivity following intraplantar injection of capsaicin (5 μg), assessed by a von Frey filament (0.16 g). Tlr3$^{-/-}$ mice have intact primary mechanical hyperalgesia at the injection site but impaired secondary mechanical hyperalgesa in the adjacent site of paw. *P<0.05, compared with WT mice. Student's t test, n=5-9 mice for each group, all data are mean±SEM.

FIGS. 2A and 2B are a series of four graphs showing number of scratches in 30 minutes following nape injection of 50 μl of compound 48/80 (48/80; 100 μg) and chloroquine (CQ; 200 μg). Note a reduction of both histaminergic (48/80) and nonhistaminergic (CQ) itch in Tlr3$^{-/-}$ mice. *P<0.05, Student's t test, n=11-13 mice; mean±SEM. Two-way repeatedly measured AVONA analysis also shows significant difference in the time course of 48/80 and CQ-induced scratching between two groups (P<0.05). FIG. 2C is a series of four photomicrographs showing c-Fos-like immunoreactivity (FLI) in the dorsal horn of the cervical spinal cord in WT and Tlr3$^{-/-}$ mice two hours after intradermal injection 48/80 or CQ into the nape of the neck. *P<0.05, Student's t test, n=4-6, all the data are mean±SEM.

FIG. 3A depicts a reduction of 48/80 and CQ-induced scratching behaviors in Tlr3$^{-/-}$ mice. FIG. 3B show that CQ, but not 48/80-induced scratching is reduced in Tlr7$^{-/-}$ mice. FIGS. 3C and 3D are bar graphs showing that neither 48/80 nor CQ-induced scratching behaviors is affected in Tlr2$^{-/-}$ mice (FIG. 3C) or Tlr4$^{-/-}$ mice (FIG. 3D). Note that wiping behaviors induced by 48/80 or CQ are normal in all 4 lines of Tlr KO mice. *P<0.05, Student's t test, n=5-8. All the data are mean±SEM.

FIG. 4A is a series of photomicrographs from single-cell RT-PCR analysis of dissociated small-size DRG neurons showing the distinct and overlapped distribution patterns of TLR2, 3, 4 and 7 in DRG neurons. FIG. 4B is a series of photomicrographs from single-cell RT-PCR from dissociated small-size DRG neurons showing co-localization of TLR3 with TPRV1 and GRP. Note that all TLR3+ cells also express GRP and TRPV1. Similar results were obtained from three independent experiments in 30 cells collected from different animals. FIG. 4C is a series of photomicrographs showing double immunostaining in DRG section showing co-colocalization of TLR3 and GRP. Bottom, cell size distribution of TLR3+ and GRP+ neurons. Scale, 50 μm. FIG. 4D is a series of photomicrographs from double immunostaining in cultured DRG neurons showing co-cocolization of TLR3 with TRPV1 (left), but not with NF200 (right). Arrows indicate double-labeled neurons. Scale, 50 μm. FIG. 4E is a series of confocal microscope images revealing the intracellular localization of TLR3. Note that TLR3 is colocalized with EEA1, an early endosome marker and partially overlapped with RAB7, a late endosome marker. DRG sections were prepared from adult mice and cultured DRG neurons from young mice (4-5 weeks).

FIG. 5A is a graph showing inward currents evoked by PIC and capsaicin in dissociated DRG neurons from WT and Tlr3$^{-/-}$ mice. Note that PIC fails to induce inward currents in Tlr3$^{-/-}$ mice. FIG. 5B is a bar graph showing a dose-dependent increase of PIC-induced inward currents. The number of responsive neurons is indicated on the top of each bar. FIG. 5C is a series of graphs from a combination of patch clamp recording and single-cell RT-PCR in small DRG neurons showing that all four neurons (out of ten) that respond to PIC (200 ng/ml) also express TLR3 mRNA. NC, negative control. FIG. 5D is a series of traces of patch clamp recording of spontaneous EPSCs (sEPSCs) in lamina II neurons in spinal cord slices from WT and Tlr3$^{-/-}$ mice. FIG. 5E is a bar graph showing sEPSC frequency and amplitude. Note that PIC (100 ng/ml) only increases the frequency but not amplitude of sEPSC frequency in WT, but not in Tlr3$^{-/-}$ mice. *P<0.05, compared with WT pretreatment baseline; $^{\#}$P<0.05, compared with WT PIC group. Student's t test, n=6 neurons. All the data are mean±SEM.

FIG. 6A is a series of traces of patch clamp recording for spontaneous EPSCs (sEPSCs) in lamina II neurons in spinal cord slices from WT and Tlr3$^{-/-}$ mice. FIG. 6B is a bar graph of sEPSC frequency and amplitude. Capsaicin (1 μM) only increases the frequency but not amplitude of sEPSC frequency in WT but not in Tlr3$^{-/-}$ mice. Note that basal synaptic transmission (sEPSC frequency without capsaicin) is also reduced in Tlr3$^{-/-}$ mice. *P<0.05, compared to pretreatment baseline; $^{\#}$P<0.05, compared to WT capsaicin group. $^{\$}$P<0.05, compared to WT control, Student's t test, n=6 neurons. FIG. 6C is a series of traces of patch clamp recording for spontaneous EPSCs (sEPSCs) in lamina II neurons in spinal cord slices from WT and Tlr7$^{-/-}$ mice. FIG. 6D is a bar graph of sEPSC frequency and amplitude. Both basal and evoked sEPSCs do not change in Tlr7$^{-/-}$ mice. n=5 neurons. FIGS. 6E and 6F are line graphs of spinal cord in vivo recordings of C-fiber evoked filed potentials in Tlr3$^{-/-}$ mice (FIG. 6E) and Tlr7$^{-/-}$ mice (FIG. 6F) and their corresponding WT controls. Note that spinal LTP is induced in Tlr7$^{-/-}$ mice (FIG. 6F), but not in Tlr3$^{-/-}$ mice (FIG. 6E). *P<0.05, compared with WT mice, Two-way repeated measures ANOVA, n=5 mice. All the data are mean±SEM.

FIG. 7A depicts knockdown effects on TLR3 expression in DRGs after intrathecal injections of Tlr3 antisense oligodeoxynucleotides (AS-ODNs, 10 μg daily for five days). Note that both TLR3 protein and mRNA levels in DRGs are down-regulated after AS-ODNs treatment, revealed by Western blotting (left) and quantitative PCR (right). *P<0.05, Student t test, n=4. FIG. 7B is a panel of two bar graphs showing inhibition of scratching induced by compound 48/80 (48/80) or chloroquine (CQ) after treatment with TLR3 AS-ODNs. *P<0.05, Student t test, n=5. FIG. 7C is a panel of two bar graphs showing no effect of TLR3 AS-ODNs on basal mechanical, heat, and cold sensitivity (P>0.05). FIG. 7D is a panel of two bar graphs showing intrathecal TRIF peptide inhibitor, an inhibitor of TLR3 signaling, reduces scratching induced by 48/80 and CQ in mice. *P<0.05, Student t test, n=5. All the data are mean±SEM.

FIG. 8A is a bar graph showing spontaneous scratching behavior induced by acetone and diethyether (1:1) following by water (AEW, twice a day for 7 days) on day 8 and 9 in WT and Tlr3$^{-/-}$ mice. *P<0.05 versus WT. FIG. 8B is a panel of two bar graphs showing real-time quantitative RT-PCR analysis of TLR3 up-regulation in skin but not DRG after AEW treatment in WT mice. *P<0.05. FIG. 8C is a panel of two bar graphs showing real-time quantitative RT-PCR analysis showing that AEW-induced upregulation of NGF, but not TNF-α, in dry skin is abrogated in Tlr3$^{-/-}$ mice. *P<0.05, #P<0.05. FIG. 8D is a bar graph of ELISA analysis showing that AEW-induced up-regulation histamine in skin is not affected in Tlr3$^{-/-}$ mice. *P<0.05, compared with vehicle control (CTRL). FIG. 8E is a bar graph showing intradermal injection of PIC is not sufficient to induce scratching. P>0.05, compared to vehicle. FIG. 8F is a bar graph showing intradermal injection of PIC enhances AEW-induced spontaneous scratching behavior, which is lost in Tlr3$^{-/-}$ mice. *P<0.05, #P<0.05, n.s., no significance. Student's t test, n=5. All the data are mean±SEM.

FIGS. 9A-9J are ten graphs showing that Tlr3$^{-/-}$ mice have impaired scratching behaviors induced by both histamine-dependent and independent pruritic agents. FIGS. 9A-9I show time courses of scratching responses for a period of 30 minutes in Tlr3$^{-/-}$ mice and WT mice, following intradermal injection of 50 μl of pruritic agents including histamine (FIG. 2A; 500 μg), HTMT (FIG. 2B; H1 receptor agonist; 100 μg), 4-MeHA (FIG. 2C; histamine H4 receptor agonist; 500 μg), endothelin-1 (FIG. 2D; ET-1; 25 ng), serotonin (FIG. 2E; 5-HT; 20 μg), SLIGRL-NH2 (FIG. 2F; PAR2 agonist; 100 μg), trypsin (FIG. 2G; 300 μg), formalin (FIG. 2H; 0.6%), and imiquimod (FIG. 2I; TLR7 agonist; 100 μg), in WT and Tlr3$^{-/-}$ mice. P<0.05, two-way repeated measured AVONA was used in the time course analysis of scratching behavior. FIG. 9J is a histogram showing the summary of scratches in 30 minutes following intradermal injection of pruritic agents. *P<0.05, Student's t test, n=6-12 mice, mean±SEM.

FIGS. 10A and 10B are bar graphs showing that Tlr2 and Tlr4 knockout mice exhibit intact acute itch responses. Tlr2 (10A) and Tlr4 knockout mice (10B) display comparable scratching responses induced by the pruritic agents compound 48/80 and chloroquine relative to WT mice (P>0.05, n=6 mice/group, Student's t test; mean±SEM).

FIGS. 11A and 11B are bar graphs showing acute and persistent inflammatory pain induced by intraplantar formalin (5%; n=5) and carrageenan (1%, n=5). P>0.05 compared with WT control. FIG. 11C is a bar graph depicting total number of scratches in 30 minutes following intradermal injection of 50 μl of pruritic agents including histamine (500 μg), HTMT (H1 agonist, 100 μg), compound 48/80 (48/80; 100 μg), serotonin (5-HT; 20 μg), endothelin-1 (ET-1, 25 ng), SLIGRL-NH2 (PAR2 agonist; 100 μg), and chloroquine (CQ; 200 μg) in Tlr7$^{-/-}$ and WT mice. *P<0.05, versus WT control, n=5-8 mice. All data are means±s.e.m.

FIG. 12A shows dose-dependent scratches after intradermal imiquimod (n=5-8). Inset, structure of imiquimod. FIG. 12B is a bar graph showing imiquimod-induced scratches in WT and Tlr7$^{-/-}$ mice (n=5). FIG. 12C depicts imiquimod-induced scratches after RTX and vehicle treatment, in Trpv1$^{-/-}$ and their WT control mice, as well as in mast cell-deficient SASH mice and their WT control mice. *P<0.05, versus saline (a), #P<0.05. N.S., not significant. n=5. All data are means±s.e.m.

FIG. 13A is a photomicrograph showing TLR7 expression in DRG neurons. Scale, 50 μm. FIGS. 13B and 13C are single cell RT-PCR analyses showing co-localization of TLR7 with TPRV1, GRP, and MrgprA3. M, molecular weights; N, negative controls from pipettes that did not harvest any cell contents but were submerged in the bath solution. * indicates TLR7+ neurons. FIG. 13D is a panel of two traces of an inward current evoked by imiquimod (500 μM) and capsaicin (0.5 μM) in small DRG neurons from WT mice. Eight out of 17 neurons from WT mice respond to imiquimod. All 10 neurons from Tlr7$^{-/-}$ mice fail to respond to imiquimod. FIG. 13E is a bar graph depicting amplitude of inward currents evoked by imiquimod (20-500 μM). Numbers over bracket indicate the number of responsive neurons. FIG. 13F is a panel of two traces of action potentials evoked by imiquimod (500 μM) and capsaicin (0.5 μM) in small DRG neurons from WT mice. Note that imiquimod-induced action potentials are lost in Tlr7$^{-/-}$ mice (n=8 neurons).

FIG. 16A is a line graph showing IMQ (20 μg)-induced scratches in WT (CD1) mice receiving treatment of TLR7 siRNA and non-targeting (NT) control siRNA. *P<0.05, compared to NT siRNA, n=5. FIG. 16B is a bar graph showing TLR7 mRNA levels in cervical DRGs, revealed by quantitative PCR. *P<0.05, n=5. siRNA (4 μg, i.t., mixed with PEI was injected 48 and 24 hours before the IMQ injection.

DETAILED DESCRIPTION

Figures 1A, 1B, 1C, 1D, 1E, 1F, 1G:
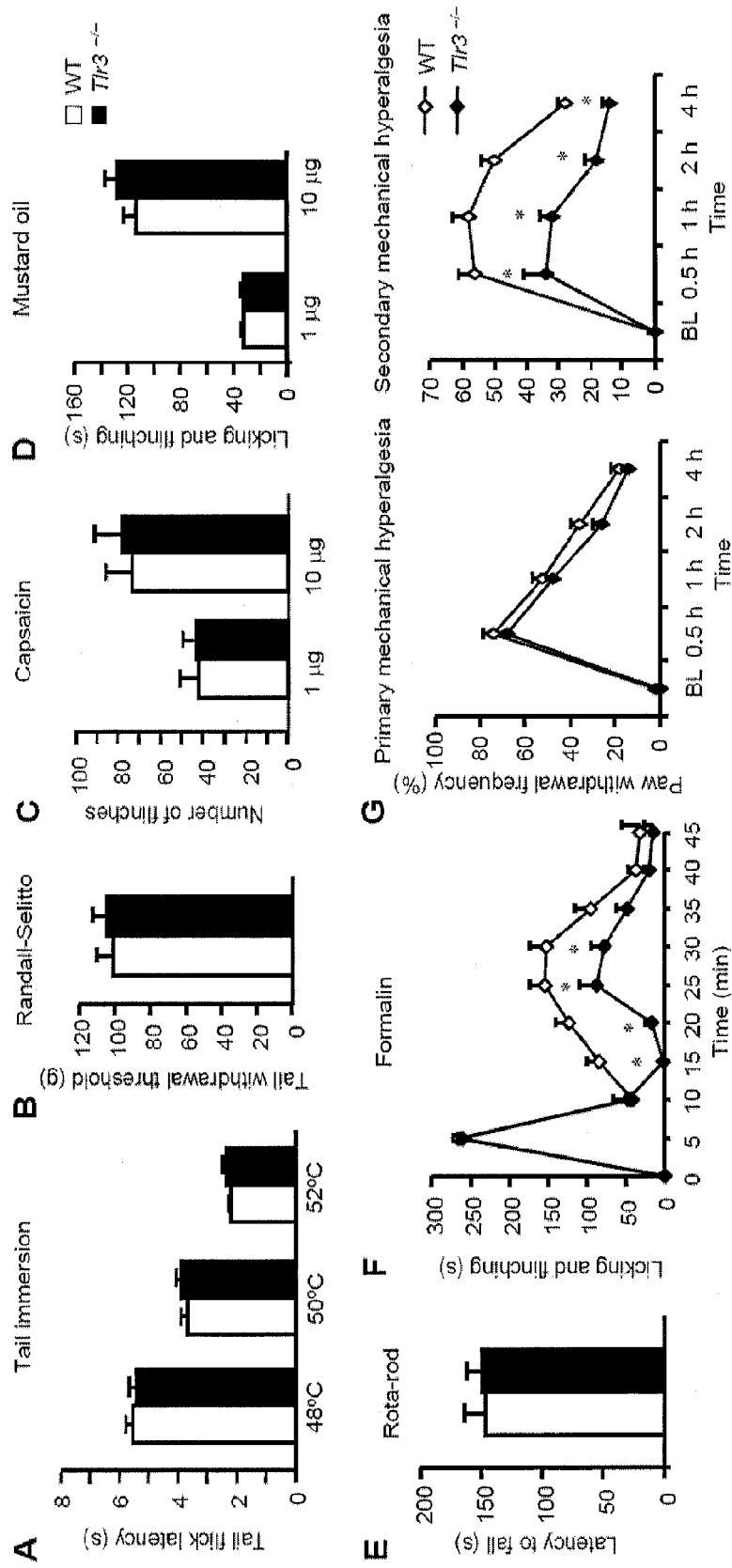
FIGS. 1A-1G are a panel of eight graphs showing that Tlr3$^{-/-}$ mice have intact acute pain but impaired central sensitization.

Itch or pruritus, commonly associated with certain medications, dermatitis, liver or kidney diseases and metabolic disorders, represents an intractable medical problem. Toll-like receptors (TLRs) are known to mediate innate immunity and regulate neuropathic pain, but their roles in pruritus are illusive. As described herein, scratching behaviors, induced by both histamine-dependent and independent pruritogens, are markedly reduced in Tlr3$^{-/-}$ mice but not in Tlr2$^{-/-}$ and Tlr4$^{-/-}$ mice. Tlr3$^{-/-}$ mice have intact acute pain, but central sensitization-driven pain is impaired in these mice. TLR3 is expressed by small-sized primary sensory neurons in dorsal root ganglion (DRG) that co-express TRPV1 and gastrin-releasing peptide (GRP). TLR3 agonist poly (I:C) induced inward currents in DRG neurons and increased excitatory synaptic transmission in spinal cord dorsal horn neurons. Notably, basal synaptic transmission, capsaicin-evoked enhancement of synaptic transmission and long-term potentiation in the spinal cord are all impaired in Tlr3$^{-/-}$ but not Tlr7$^{-/-}$ mice. Antisense knockdown of TLR3 in DRGs of wild-type adult mice also attenuated pruritus. Finally, chronic itch in a dry skin condition is substantially reduced in Tlr3$^{-/-}$ mice. These findings demonstrate an unexpected role of TLR3 in spinal cord synaptic transmission, central sensitization and identify TLR3 as a new target for anti-itch treatment.

In addition, as described herein, functional TLR7 is expressed in C-fiber primary sensory neurons and important for inducing itch (pruritus) but not necessary for eliciting mechanical, thermal, inflammatory and neuropathic pain in mice. Thus, TLR7 is a novel itch mediator and a potential therapeutic target for anti-itch treatment in skin disease conditions.

Methods of Treatment

The methods described herein include methods for the treatment of disorders associated with itching (e.g., pruritus). In some embodiments, the disorder is itch associated with dermatitis, liver or kidney diseases and metabolic disorders. In some embodiments, the disorder is itch associated with administration of a drug, i.e., acute or chronic drug-induced pruritus (see, e.g., Reich et al., Acta Derm Venereol. 2009; 89(3):236-44). Generally, the methods include administering, e.g., systemically or topically (e.g., to an affected area) a therapeutically effective amount of an inhibitor of TLR3/7 as described herein, to a subject who is in need of, or who has been determined to be in need of, such treatment.

As used in this context, to "treat" means to ameliorate at least one symptom of the disorder associated with itch. These conditions are characterized by chronic itching, thus, a treatment can result in a reduction in itching, e.g., a reduction in frequency or severity. Administration of a therapeutically effective amount of a compound described herein for the treatment of a condition associated with itching will result in decreased itching.

Toll-Like Receptors

Toll-like receptors (TLRs), the key pattern-recognition receptors (PRR), mediate innate immune responses via recognizing molecular structures from pathogen-associated molecular patterns (PAMPs) (22; 23). The mammalian TLR family consists of at least 13 members (TLR1-13). Each TLR recognizes distinct PAMPs. TLRs located in plasma membrane appear to sense bacterial membrane components. For example, TLR2 and TLR4 can sense peptidoglycan and lipopolysaccharide (LPS), respectively (23). On the other hand, TLRs located in intracellular endosomal compartments detect nucleic acids. For instance, TLR3 and TLR7 recognize double-stranded RNA (24; 25) and single-stranded RNA (26; 27), respectively. It has been shown that microglia recognize double-stranded RNA via TLR3 (25), and further, TLR3 mediates West Nile virus entry into the brain causing lethal encephalitis (24).

Of interest TLR2, TLR3 and TLR4 have been implicated in the development of neuropathic pain through inducing glial activation and proinflammatory cytokines in the spinal cord (28-30). Although TLRs are typically expressed by immune and glial cells, increasing evidence indicates that TLRs are also expressed by primary sensory neurons (31-33). But the functions of these TLRs in sensory neurons are largely unknown. Recently, we demonstrated that TLR7 is functionally expressed in TRPV1-expressing nociceptors and contributed to histamine-independent pruritus, without affecting mechanical, thermal, inflammatory and neuropathic pain (34). In the present study, we tested the hypothesis that TLRs play distinct roles in pain and itch.

TLR3 and TLR7—Itch Mediators

As described herein, TLR3, but not TLR2 and TLR4, is essential for eliciting both histamine-dependent and independent pruritus. Chronic itch following dry skin-induced dermatitis is abrogated in Tlr3$^{-/-}$ mice. By contrast, acute pain after thermal, mechanical, and chemical stimulation is normal in Tlr3$^{-/-}$ mice. In addition, TLR7 mediates itch sensation.

Central sensitization, hyperactivity of spinal cord dorsal horn neurons after tissue injury or persistent nociceptive input (e.g., C-fiber activation), is believed to cause hypersensitivity to pain (35) and itch (6; 36). Long-term potentiation (LTP) in the spinal cord is a typical example of synaptic plasticity (37) and central sensitization (35). In this study the role of TLR3 in central sensitization and spinal cord synaptic transmission was also examined. As described herein, spinal LTP was induced in Tlr7$^{-/-}$ mice but not Tlr3$^{-/-}$ mice. Further, behavioral expression of central sensitization, the formalin-induced $2^{nd}$ phase pain (35) and the capsaicin-induced secondary mechanical hyperalgesia (38), were impaired in Tlr3$^{-/-}$ mice.

TLR3 and TLR7 Antagonists

A number of TLR3 and TLR7 antagonists are known in the art and can be used in the methods described herein. For example, monoclonal antibodies have been described that bind the extracellular domain of TLR3 and inhibit TLR3 activity. See, e.g., Bunting et al., Cell Immunol. 2011; 267 (1):9-16. Epub 2010 Nov. 2; Duffy et al., Cell Immunol. 2007; 248(2):103-114; and US 20060115475. Small molecule inhibitors of TLR3 are also known in the art, see, e.g., Cheng et al., J Am Chem. Soc. 2011 Mar. 23; 133(11):3764-7. Epub 2011 Feb. 28 (e.g., compound 4a described therein); Zhu et al., J. Immunol. May 15, 2010; 184(10):5768-5776 (describing sertraline (SRT) and trifluoperazine (TFP) as TLR3/TLR7 signalling antagonists); and Schwartz et al., Clin Cancer Res. 2009 Jun. 15; 15(12):4114-22. Epub 2009 May 26 (describing phenylmethimazole (C10; Interthyr Corporation) as a TLR3 inhibitor, see U.S. Pat. No. 6,365,616 and FIG. 1 of Giuliani et al., J Endocrinol Jan. 1, 2010; 204:57-66 for structure of phenylmethimazole).

A number of small molecule inhibitors of TLR7 are known in the art, e.g., single-stranded phosphorothioate oligonucleotides, 2'-modified RNAs, and other TLR7 antagonist oligodeoxynucleotides (Wang et al., J Med. Chem. 2009 Jan. 22; 52(2):551-8; Yu et al., J Med. Chem. 2009 Aug. 27; 52(16): 5108-14; Hamm et al., Immunobiology. 2010 July; 215(7): 559-69. Epub 2009 Oct. 25; and Sioud, Methods Mol. Biol. 2010; 629:387-94), including Immune Modulatory Oligonucleotides IMO-3100 (Idera Pharmaceuticals); IRS661 and IRS954 (Pawar et al., J Am Soc Nephrol 18:1721-1731, 2007); quinazoline compounds such as CPG52364 described in U.S. Pat. No. 7,410,975 (Coley Pharmaceutical Group); the imidazoquinoline des-amino precursor of the 3H regioisomer of Gardiquimod (Shukla et al., Bioorg Med Chem. Lett. 2009 Apr. 15; 19(8):2211-4. Epub 2009 Feb. 28); quinacrine (Sun et al., Inflamm Allergy Drug Targets. 2007 December; 6(4): 223-35); and IRS 661 (Banat et al., 2005; J. Exp. Med. 202: 1131-1139). Other antagonists include 2-((4-((7-Chloro-4-quinolyl)amino)pentyl)ethylamino)ethanol.

Antibodies against TLR7 are also known in the art and may be useful in the present methods, including IMG-581A (Imgenex). Commercially available antibodies can be purchased from Abcam; AbD Serotec; AbFrontier Co., Ltd.; Abnova Corporation; ABR, now sold as Thermo Scientific Pierce Antibodies; Acris Antibodies GmbH; ARP American Research Products, Inc.; Assay Designs/Stressgen (Now Enzo Life Sciences); Biorbyt; BioVision; Cell Sciences; Cell Signaling Technology; eBioscience; EMD Millipore; Enzo Life Sciences, Inc.; Fitzgerald Industries International; GeneTex; GenWay Biotech, Inc.; Hycult Biotech; IBL—America (Immuno-Biological Laboratories); IMGENEX; Invitrogen; LifeSpan BioSciences; MBL International; Novus Biologicals; ProSci, Inc; Proteintech Group, Inc.; R&D Systems; Raybiotech, Inc.; Rockland Immunochemicals, Inc.; Santa Cruz Biotechnology, Inc.; Sigma-Aldrich; Thermo Scientific Pierce Protein Research Products; and United States Biological.

Antagonists known to cause pruritus should generally be avoided (e.g., chloroquine and hydroxychloroquine, see, e.g., Reich et al., Acta Derm Venereol. 2009; 89(3):236-44).

Inhibitory Nucleic Acids

Inhibitory nucleic acids targeting TLR3 and TLR7 as known in the art and described herein can also be used in the methods described herein.

Inhibitory nucleic acids useful in the present methods and compositions include antisense oligonucleotides, ribozymes, external guide sequence (EGS) oligonucleotides, siRNA compounds, single- or double-stranded RNA interference (RNAi) compounds such as siRNA compounds, modified bases/locked nucleic acids (LNAs), antagomirs, peptide nucleic acids (PNAs), and other oligomeric compounds or oligonucleotide mimetics which hybridize to at least a portion of the target nucleic acid and modulate its function. In some embodiments, the inhibitory nucleic acids include antisense RNA, antisense DNA, chimeric antisense oligonucleotides, antisense oligonucleotides comprising modified linkages, interference RNA (RNAi), short interfering RNA (siRNA); a micro, interfering RNA (miRNA); a small, temporal RNA (stRNA); or a short, hairpin RNA (shRNA); small RNA-induced gene activation (RNAa); small activating RNAs (saRNAs), or combinations thereof. See, e.g., WO 2010040112.

In some embodiments, the inhibitory nucleic acids are 10 to 50, 13 to 50, or 13 to 30 nucleotides in length. One having ordinary skill in the art will appreciate that this embodies oligonucleotides having antisense portions of 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, or 50 nucleotides in length, or any range therewithin. In some embodiments, the oligonucleotides are 15 nucleotides in length. In some embodiments, the antisense or oligonucleotide compounds of the invention are 12 or 13 to 30 nucleotides in length. One having ordinary skill in the art will appreciate that this embodies inhibitory nucleic acids having antisense portions of 12, 13, 14, 15, 16, 17, 18, 19, 20, 21, 22, 23, 24, 25, 26, 27, 28, 29 or 30 nucleotides in length, or any range therewithin.

In some embodiments, the inhibitory nucleic acids are chimeric oligonucleotides that contain two or more chemically distinct regions, each made up of at least one nucleotide. These oligonucleotides typically contain at least one region of modified nucleotides that confers one or more beneficial properties (such as, for example, increased nuclease resistance, increased uptake into cells, increased binding affinity for the target) and a region that is a substrate for enzymes capable of cleaving RNA:DNA or RNA:RNA hybrids. Chimeric inhibitory nucleic acids of the invention may be formed as composite structures of two or more oligonucleotides, modified oligonucleotides, oligonucleosides and/or oligonucleotide mimetics as described above. Such compounds have also been referred to in the art as hybrids or gapmers. Representative United States patents that teach the preparation of such hybrid structures comprise, but are not limited to, U.S. Pat. Nos. 5,013,830; 5,149,797; 5,220,007; 5,256,775; 5,366,878; 5,403,711; 5,491,133; 5,565,350; 5,623,065; 5,652,355; 5,652,356; and 5,700,922, each of which is herein incorporated by reference.

In some embodiments, the inhibitory nucleic acid comprises at least one nucleotide modified at the 2' position of the sugar, most preferably a 2'-O-alkyl, 2'-β-alkyl-O-alkyl or 2'-fluoro-modified nucleotide. In other preferred embodiments, RNA modifications include 2'-fluoro, 2'-amino and 2' O-methyl modifications on the ribose of pyrimidines, abasic residues or an inverted base at the 3' end of the RNA. Such modifications are routinely incorporated into oligonucleotides and these oligonucleotides have been shown to have a higher Tm (i.e., higher target binding affinity) than; 2'-deoxyoligonucleotides against a given target.

A number of nucleotide and nucleoside modifications have been shown to make the oligonucleotide into which they are incorporated more resistant to nuclease digestion than the native oligodeoxynucleotide; these modified oligos survive intact for a longer time than unmodified oligonucleotides. Specific examples of modified oligonucleotides include those comprising modified backbones, for example, phosphorothioates, phosphotriesters, methyl phosphonates, short chain alkyl or cycloalkyl intersugar linkages or short chain heteroatomic or heterocyclic intersugar linkages. <ost preferred are oligonucleotides with phosphorothioate backbones and those with heteroatom backbones, particularly CH2-NH—O—CH2, CH, ~N(CH3)~O~CH2 (known as a methylene(methylimino) or MMI backbone], CH2-O—N(CH3)-CH2, CH2-N(CH3)-N (CH3)-CH2 and O—N(CH3)-CH2-CH2 backbones, wherein the native phosphodiester backbone is represented as O—P—O—CH1); amide backbones (see De Mesmaeker et al. Ace. Chem. Res. 1995, 28:366-374); morpholino backbone structures (see Summerton and Weller, U.S. Pat. No. 5,034,506); peptide nucleic acid (PNA) backbone (wherein the phosphodiester backbone of the oligonucleotide is replaced with a polyamide backbone, the nucleotides being bound directly or indirectly to the aza nitrogen atoms of the polyamide backbone, see Nielsen et al., Science 1991, 254, 1497). Phosphorus-containing linkages include, but are not limited to, phosphorothioates, chiral phosphorothioates, phosphorodithioates, phosphotriesters, aminoalkylphosphotriesters, methyl and other alkyl phosphonates comprising 3' alkylene phosphonates and chiral phosphonates, phosphinates, phosphoramidates comprising 3'-amino phosphoramidate and aminoalkylphosphoramidates, thionophosphoramidates, thionoalkylphosphonates, thionoalkylphosphotriesters, and boranophosphates having normal 3'-5' linkages, 2'-5' linked analogs of these, and those having inverted polarity wherein the adjacent pairs of nucleoside units are linked 3'-5' to 5'-3' or 2'-5' to 5'-2; see U.S. Pat. Nos. 3,687,808; 4,469,863; 4,476,301; 5,023,243; 5,177,196; 5,188,897; 5,264,423; 5,276,019; 5,278,302; 5,286,717; 5,321,131; 5,399,676; 5,405,939; 5,453,496; 5,455, 233; 5,466,677; 5,476,925; 5,519,126; 5,536,821; 5,541,306; 5,550,111; 5,563, 253; 5,571,799; 5,587,361; and 5,625,050.

Morpholino-based oligomeric compounds are described in Dwaine A. Braasch and David R. Corey, Biochemistry, 2002, 41(14), 4503-4510; Genesis, volume 30, issue 3, 2001; Heasman, J., Dev. Biol., 2002, 243, 209-214; Nasevicius et al., Nat. Genet., 2000, 26, 216-220; Lacerra et al., Proc. Natl. Acad. Sci., 2000, 97, 9591-9596; and U.S. Pat. No. 5,034,506, issued Jul. 23, 1991.

Cyclohexenyl nucleic acid oligonucleotide mimetics are described in Wang et al., J. Am. Chem. Soc., 2000, 122, 8595-8602.

Modified oligonucleotide backbones that do not include a phosphorus atom therein have backbones that are formed by short chain alkyl or cycloalkyl internucleoside linkages, mixed heteroatom and alkyl or cycloalkyl internucleoside linkages, or one or more short chain heteroatomic or heterocyclic internucleoside linkages. These comprise those having morpholino linkages (formed in part from the sugar portion of a nucleoside); siloxane backbones; sulfide, sulfoxide and sulfone backbones; formacetyl and thioformacetyl backbones; methylene formacetyl and thioformacetyl backbones; alkene containing backbones; sulfamate backbones; methyleneimino and methylenehydrazino backbones; sulfonate and sulfonamide backbones; amide backbones; and others having mixed N, O, S and CH2 component parts; see U.S. Pat. Nos. 5,034,506; 5,166,315; 5,185,444; 5,214,134; 5,216,141; 5,235,033; 5,264,562; 5,264,564; 5,405,938; 5,434,257; 5,466,677; 5,470,967; 5,489,677; 5,541,307; 5,561,225; 5,596,086; 5,602,240; 5,610,289; 5,602,240; 5,608,046; 5,610,289; 5,618,704; 5,623,070; 5,663,312; 5,633,360; 5,677,437; and 5,677,439, each of which is herein incorporated by reference.

One or more substituted sugar moieties can also be included, e.g., one of the following at the 2' position: OH, SH, SCH$_3$, F, OCN, OCH$_3$ OCH$_3$, OCH$_3$O(CH$_2$)n CH$_3$, O(CH$_2$)n NH$_2$ or O(CH$_2$)n CH$_3$ where n is from 1 to about 10; Ci to C10 lower alkyl, alkoxyalkoxy, substituted lower alkyl, alkaryl or aralkyl; Cl; Br; CN; CF3; OCF3; O-, S-, or N-alkyl; O-, S-, or N-alkenyl; SOCH3; SO2 CH3; ONO2; NO2; N3; NH2; heterocycloalkyl; heterocycloalkaryl; aminoalkylamino; polyalkylamino; substituted silyl; an RNA cleaving group; a reporter group; an intercalator; a group for improving the pharmacokinetic properties of an oligonucleotide; or a group for improving the pharmacodynamic properties of an oligonucleotide and other substituents having similar properties. A preferred modification includes 2'-methoxyethoxy [2'-0-CH$_2$CH$_2$OCH$_3$, also known as 2'-O-(2-methoxyethyl)] (Martin et al, Helv. Chim. Acta, 1995, 78, 486). Other preferred modifications include 2'-methoxy (2'-0-CH$_3$), 2'-propoxy (2'-OCH$_2$ CH$_2$CH$_3$) and 2'-fluoro (2'-F). Similar modifications may also be made at other positions on the oligonucleotide, particularly the 3' position of the sugar on the 3' terminal nucleotide and the 5' position of 5' terminal nucleotide. Oligonucleotides may also have sugar mimetics such as cyclobutyls in place of the pentofuranosyl group.

Inhibitory nucleic acids can also include, additionally or alternatively, nucleobase (often referred to in the art simply as "base") modifications or substitutions. As used herein, "unmodified" or "natural" nucleobases include adenine (A), guanine (G), thymine (T), cytosine (C) and uracil (U). <odified nucleobases include nucleobases found only infrequently or transiently in natural nucleic acids, e.g., hypoxanthine, 6-methyladenine, 5-Me pyrimidines, particularly 5-methylcytosine (also referred to as 5-methyl-2' deoxycytosine and often referred to in the art as 5-Me-C), 5-hydroxymethylcytosine (HMC), glycosyl HMC and gentobiosyl HMC, as well as synthetic nucleobases, e.g., 2-aminoadenine, 2-(methylamino)adenine, 2-(imidazolylalkyl)adenine, 2-(aminoalklyamino)adenine or other heterosubstituted alkyladenines, 2-thiouracil, 2-thiothymine, 5-bromouracil, 5-hydroxymethyluracil, 8-azaguanine, 7-deazaguanine, N6 (6-aminohexyl)adenine and 2,6-diaminopurine. Kornberg, A., DNA Replication, W. H. Freeman & Co., San Francisco, 1980, pp 75-77; Gebeyehu, G., et al. Nucl. Acids Res. 1987, 15:4513). A "universal" base known in the art, e.g., inosine, can also be included. 5-Me-C substitutions have been shown to increase nucleic acid duplex stability by 0.6-1.2<0>C. (Sanghvi, Y. S., in Crooke, S. T. and Lebleu, B., eds., Antisense Research and Applications, CRC Press, Boca Raton, 1993, pp. 276-278) and are presently preferred base substitutions.

It is not necessary for all positions in a given oligonucleotide to be uniformly modified, and in fact more than one of the aforementioned modifications may be incorporated in a single oligonucleotide or even at within a single nucleoside within an oligonucleotide.

In some embodiments, both a sugar and an internucleoside linkage, i.e., the backbone, of the nucleotide units are replaced with novel groups. The base units are maintained for hybridization with an appropriate nucleic acid target compound. One such oligomeric compound, an oligonucleotide mimetic that has been shown to have excellent hybridization properties, is referred to as a peptide nucleic acid (PNA). In PNA compounds, the sugar-backbone of an oligonucleotide is replaced with an amide containing backbone, for example, an aminoethylglycine backbone. The nucleobases are retained and are bound directly or indirectly to aza nitrogen atoms of the amide portion of the backbone. Representative United States patents that teach the preparation of PNA compounds comprise, but are not limited to, U.S. Pat. Nos. 5,539,082; 5,714,331; and 5,719,262, each of which is herein incorporated by reference. Further teaching of PNA compounds can be found in Nielsen et al, Science, 1991, 254, 1497-1500.

Inhibitory nucleic acids can also include one or more nucleobase (often referred to in the art simply as "base") modifications or substitutions. As used herein, "unmodified" or "natural" nucleobases comprise the purine bases adenine (A) and guanine (G), and the pyrimidine bases thymine (T), cytosine (C) and uracil (U). Modified nucleobases comprise other synthetic and natural nucleobases such as 5-methylcytosine (5-me-C), 5-hydroxymethyl cytosine, xanthine, hypoxanthine, 2-aminoadenine, 6-methyl and other alkyl derivatives of adenine and guanine, 2-propyl and other alkyl derivatives of adenine and guanine, 2-thiouracil, 2-thiothymine and 2-thiocytosine, 5-halouracil and cytosine, 5-propynyl uracil and cytosine, 6-azo uracil, cytosine and thymine, 5-uracil (pseudo-uracil), 4-thiouracil, 8-halo, 8-amino, 8-thiol, 8-thioalkyl, 8-hydroxyl and other 8-substituted adenines and guanines, 5-halo particularly 5-bromo, 5-trifluoromethyl and other 5-substituted uracils and cytosines, 7-methylquanine and 7-methyladenine, 8-azaguanine and 8-azaadenine, 7-deazaguanine and 7-deazaadenine and 3-deazaguanine and 3-deazaadenine.

Further, nucleobases comprise those disclosed in U.S. Pat. No. 3,687,808, those disclosed in 'The Concise Encyclopedia of Polymer Science And Engineering', pages 858-859, Kroschwitz, J. I., ed. John Wiley & Sons, 1990, those disclosed by Englisch et al., Angewandle Chemie, International Edition', 1991, 30, page 613, and those disclosed by Sanghvi, Y. S., Chapter 15, Antisense Research and Applications', pages 289-302, Crooke, S. T. and Lebleu, B. ea., CRC Press, 1993. Certain of these nucleobases are particularly useful for increasing the binding affinity of the oligomeric compounds of the invention. These include 5-substituted pyrimidines, 6-azapyrimidines and N-2, N-6 and 0-6 substituted purines, comprising 2-aminopropyladenine, 5-propynyluracil and 5-propynylcytosine. 5-methylcytosine substitutions have been shown to increase nucleic acid duplex stability by 0.6-1.2<0>C (Sanghvi, Y. S., Crooke, S. T. and Lebleu, B., eds, 'Antisense Research and Applications', CRC Press, Boca Raton, 1993, pp. 276-278) and are presently preferred base substitutions, even more particularly when combined with 2'-O-methoxyethyl sugar modifications. Modified nucleobases are described in U.S. Pat. No. 3,687,808, as well as U.S. Pat. Nos. 4,845,205; 5,130,302; 5,134,066; 5,175, 273; 5,367,066; 5,432,272; 5,457,187; 5,459,255; 5,484,908; 5,502,177; 5,525,711; 5,552,540; 5,587,469; 5,596,091; 5,614,617; 5,750,692, and 5,681,941, each of which is herein incorporated by reference.

In some embodiments, the inhibitory nucleic acids are chemically linked to one or more moieties or conjugates that enhance the activity, cellular distribution, or cellular uptake of the oligonucleotide. Such moieties comprise but are not limited to, lipid moieties such as a cholesterol moiety (Letsinger et al., Proc. Natl. Acad. Sci. USA, 1989, 86, 6553-6556), cholic acid (Manoharan et al., Bioorg. Med. Chem. Let., 1994, 4, 1053-1060), a thioether, e.g., hexyl-S-tritylthiol (Manoharan et al, Ann. N.Y. Acad. Sci., 1992, 660, 306-309; Manoharan et al., Bioorg. Med. Chem. Let., 1993, 3, 2765-2770), a thiocholesterol (Oberhauser et al., Nucl. Acids Res., 1992, 20, 533-538), an aliphatic chain, e.g., dodecandiol or undecyl residues (Kabanov et al., FEBS Lett., 1990, 259, 327-330; Svinarchuk et al., Biochimie, 1993, 75, 49-54), a phospholipid, e.g., di-hexadecyl-rac-glycerol or triethylammonium 1,2-di-O-hexadecyl-rac-glycero-3-H-phosphonate (Manoharan et al., Tetrahedron Lett., 1995, 36, 3651-3654; Shea et al., Nucl. Acids Res., 1990, 18, 3777-3783), a polyamine or a polyethylene glycol chain (Mancharan et al., Nucleosides & Nucleotides, 1995, 14, 969-973), or adamantane acetic acid (Manoharan et al., Tetrahedron Lett., 1995, 36, 3651-3654), a palmityl moiety (Mishra al., Biochim. Biophys. Acta, 1995, 1264, 229-237), or an octadecylamine or hexylamino-carbonyl-t oxycholesterol moiety (Crooke et al., J. Pharmacol. Exp. Ther., 1996, 277, 923-937). See also U.S. Pat. Nos. 4,828,979; 4,948,882; 5,218,105; 5,525,465; 5,541, 313; 5,545,730; 5,552, 538; 5,578,717, 5,580,731; 5,580, 731; 5,591,584; 5,109,124; 5,118,802; 5,138,045; 5,414,077; 5,486, 603; 5,512,439; 5,578,718; 5,608,046; 4,587,044; 4,605,735; 4,667,025; 4,762, 779; 4,789,737; 4,824,941; 4,835,263; 4,876,335; 4,904,582; 4,958,013; 5,082, 830; 5,112,963; 5,214,136; 5,082,830; 5,112,963; 5,214,136; 5,245,022; 5,254,469; 5,258,506; 5,262,536; 5,272,250; 5,292,873; 5,317,098; 5,371,241, 5,391,723; 5,416,203, 5,451,463; 5,510,475; 5,512,667; 5,514,785; 5,565,552; 5,567,810; 5,574,142; 5,585,481; 5,587,371; 5,595,726; 5,597,696; 5,599,923; 5,599, 928 and 5,688,941, each of which is herein incorporated by reference.

These moieties or conjugates can include conjugate groups covalently bound to functional groups such as primary or secondary hydroxyl groups. Conjugate groups of the invention include intercalators, reporter molecules, polyamines, polyamides, polyethylene glycols, polyethers, groups that enhance the pharmacodynamic properties of oligomers, and groups that enhance the pharmacokinetic properties of oligomers. Typical conjugate groups include cholesterols, lipids, phospholipids, biotin, phenazine, folate, phenanthridine, anthraquinone, acridine, fluoresceins, rhodamines, coumarins, and dyes. Groups that enhance the pharmacodynamic properties, in the context of this invention, include groups that improve uptake, enhance resistance to degradation, and/or strengthen sequence-specific hybridization with the target nucleic acid. Groups that enhance the pharmacokinetic properties, in the context of this invention, include groups that improve uptake, distribution, metabolism or excretion of the compounds of the present invention. Representative conjugate groups are disclosed in International Patent Application No. PCT/US92/09196, filed Oct. 23, 1992, and U.S. Pat. No. 6,287,860, which are incorporated herein by reference. Conjugate moieties include, but are not limited to, lipid moieties such as a cholesterol moiety, cholic acid, a thioether, e.g., hexyl-5-tritylthiol, a thiocholesterol, an aliphatic chain, e.g., dodecandiol or undecyl residues, a phospholipid, e.g., dihexadecyl-rac-glycerol or triethylammonium 1,2-di-O-hexadecyl-rac-glycero-3-H-phosphonate, a polyamine or a polyethylene glycol chain, or adamantane acetic acid, a palmityl moiety, or an octadecylamine or hexylamino-carbonyl-oxy cholesterol moiety. See, e.g., U.S. Pat. Nos. 4,828,979; 4,948, 882; 5,218,105; 5,525,465; 5,541,313; 5,545,730; 5,552,538; 5,578,717, 5,580,731; 5,580,731; 5,591,584; 5,109,124; 5,118,802; 5,138,045; 5,414,077; 5,486,603; 5,512,439; 5,578,718; 5,608,046; 4,587,044; 4,605,735; 4,667,025; 4,762,779; 4,789,737; 4,824,941; 4,835,263; 4,876,335; 4,904,582; 4,958,013; 5,082,830; 5,112,963; 5,214,136; 5,082,830; 5,112,963; 5,214,136; 5,245,022; 5,254,469; 5,258,506; 5,262,536; 5,272,250; 5,292,873; 5,317,098; 5,371,241, 5,391,723; 5,416,203, 5,451,463; 5,510,475; 5,512,667; 5,514,785; 5,565,552; 5,567,810; 5,574,142; 5,585,481; 5,587,371; 5,595,726; 5,597,696; 5,599,923; 5,599,928 and 5,688,941.

The inhibitory nucleic acids useful in the present methods are sufficiently complementary to the target sequence, i.e., hybridize sufficiently well and with sufficient specificity, to give the desired effect. "Complementary" refers to the capacity for pairing, through hydrogen bonding, between two sequences comprising naturally or non-naturally occurring bases or analogs thereof. For example, if a base at one position of an inhibitory nucleic acid is capable of hydrogen bonding with a base at the corresponding position of a target sequence, then the bases are considered to be complementary to each other at that position. 100% complementarity is not required.

In some embodiments, the location on a target sequence to which an inhibitory nucleic acids hybridizes is defined as a target region to which a protein binding partner binds. These regions can be identified by reviewing the data submitted herewith in Appendix I and identifying regions that are enriched in the dataset; these regions are likely to include the protein binding sequences. Routine methods can be used to design an inhibitory nucleic acid that binds to this sequence with sufficient specificity. In some embodiments, the methods include using bioinformatics methods known in the art to identify regions of secondary structure, e.g., one, two, or more stem-loop structures, or pseudoknots, and selecting those regions to target with an inhibitory nucleic acid.

While the specific sequences of certain exemplary target segments are set forth herein, one of skill in the art will recognize that these serve to illustrate and describe particular embodiments within the scope of the present invention. Additional target segments are readily identifiable by one having ordinary skill in the art in view of this disclosure. Target segments 5-500 nucleotides in length comprising a stretch of at least five (5) consecutive nucleotides within the protein binding region, or immediately adjacent thereto, are considered to be suitable for targeting as well. Target segments can include sequences that comprise at least the 5 consecutive nucleotides from the 5'-terminus of one of the protein binding regions (the remaining nucleotides being a consecutive stretch of the same RNA beginning immediately upstream of the 5'-terminus of the binding segment and continuing until the inhibitory nucleic acid contains about 5 to about 100 nucleotides). Similarly preferred target segments are represented by RNA sequences that comprise at least the 5 consecutive nucleotides from the 3'-terminus of one of the illustrative preferred target segments (the remaining nucleotides being a consecutive stretch of the same target sequence beginning immediately downstream of the 3'-terminus of the target segment and continuing until the inhibitory nucleic acid contains about 5 to about 100 nucleotides). One having skill in the art armed with the sequences provided herein will be able, without undue experimentation, to identify further preferred protein binding regions to target.

Once one or more target regions, segments or sites have been identified, inhibitory nucleic acid compounds are chosen that are sufficiently complementary to the target, i.e., that hybridize sufficiently well and with sufficient specificity (i.e., do not substantially bind to other non-target RNAs), to give the desired effect.

In the context of this invention, hybridization means hydrogen bonding, which may be Watson-Crick, Hoogsteen or reversed Hoogsteen hydrogen bonding, between complementary nucleoside or nucleotide bases. For example, adenine and thymine are complementary nucleobases which pair through the formation of hydrogen bonds. Complementary, as used herein, refers to the capacity for precise pairing between two nucleotides. For example, if a nucleotide at a certain position of an oligonucleotide is capable of hydrogen bonding with a nucleotide at the same position of a target sequence molecule, then the inhibitory nucleic acid and the target sequence are considered to be complementary to each other at that position. The inhibitory nucleic acids and the target sequence are complementary to each other when a sufficient number of corresponding positions in each molecule are occupied by nucleotides which can hydrogen bond with each other. Thus, "specifically hybridizable" and "complementary" are terms which are used to indicate a sufficient degree of complementarity or precise pairing such that stable and specific binding occurs between the inhibitory nucleic acid and the target sequence target. For example, if a base at one position of an inhibitory nucleic acid is capable of hydrogen bonding with a base at the corresponding position of a target sequence, then the bases are considered to be complementary to each other at that position. 100% complementarity is not required.

It is understood in the art that a complementary nucleic acid sequence need not be 100% complementary to that of its target nucleic acid to be specifically hybridisable. A complementary nucleic acid sequence for purposes of the present methods is specifically hybridisable when binding of the sequence to the target sequence molecule interferes with the normal function of the target sequence to cause a loss of activity, and there is a sufficient degree of complementarity to avoid non-specific binding of the sequence to non-target sequence sequences under conditions in which specific binding is desired, e.g., under physiological conditions in the case of in vivo assays or therapeutic treatment, and in the case of in vitro assays, under conditions in which the assays are performed under suitable conditions of stringency. For example, stringent salt concentration will ordinarily be less than about 750 mM NaCl and 75 mM trisodium citrate, preferably less than about 500 mM NaCl and 50 mM trisodium citrate, and more preferably less than about 250 mM NaCl and 25 mM trisodium citrate. Low stringency hybridization can be obtained in the absence of organic solvent, e.g., formamide, while high stringency hybridization can be obtained in the presence of at least about 35% formamide, and more preferably at least about 50% formamide. Stringent temperature conditions will ordinarily include temperatures of at least about 30° C., more preferably of at least about 37° C., and most preferably of at least about 42° C. Varying additional parameters, such as hybridization time, the concentration of detergent, e.g., sodium dodecyl sulfate (SDS), and the inclusion or exclusion of carrier DNA, are well known to those skilled in the art. Various levels of stringency are accomplished by combining these various conditions as needed. In a preferred embodiment, hybridization will occur at 30° C. in 750 mM NaCl, 75 mM trisodium citrate, and 1% SDS. In a more preferred embodiment, hybridization will occur at 37° C. in 500 mM NaCl, 50 mM trisodium citrate, 1% SDS, 35% formamide, and 100 µg/ml denatured salmon sperm DNA (ssDNA). In a most preferred embodiment, hybridization will occur at 42° C. in 250 mM NaCl, 25 mM trisodium citrate, 1% SDS, 50% formamide, and 200 µg/ml ssDNA. Useful variations on these conditions will be readily apparent to those skilled in the art.

For most applications, washing steps that follow hybridization will also vary in stringency. Wash stringency conditions can be defined by salt concentration and by temperature. As above, wash stringency can be increased by decreasing salt concentration or by increasing temperature. For example, stringent salt concentration for the wash steps will preferably be less than about 30 mM NaCl and 3 mM trisodium citrate, and most preferably less than about 15 mM NaCl and 1.5 mM trisodium citrate. Stringent temperature conditions for the wash steps will ordinarily include a temperature of at least about 25° C., more preferably of at least about 42° C., and even more preferably of at least about 68° C. In a preferred embodiment, wash steps will occur at 25° C. in 30 mM NaCl, 3 mM trisodium citrate, and 0.1% SDS. In a more preferred embodiment, wash steps will occur at 42° C. in 15 mM NaCl, 1.5 mM trisodium citrate, and 0.1% SDS. In a more preferred embodiment, wash steps will occur at 68° C. in 15 mM NaCl, 1.5 mM trisodium citrate, and 0.1% SDS. Additional variations on these conditions will be readily apparent to those skilled in the art. Hybridization techniques are well known to those skilled in the art and are described, for example, in Benton and Davis (Science 196:180, 1977); Grunstein and Hogness (Proc. Natl. Acad. Sci., USA 72:3961, 1975); Ausubel et al. (Current Protocols in Molecular Biology, Wiley Interscience, New York, 2001); Berger and Kimmel (Guide to Molecular Cloning Techniques, 1987, Academic Press, New York); and Sambrook et al., *Molecular Cloning: A Laboratory Manual*, Cold Spring Harbor Laboratory Press, New York.

In general, the inhibitory nucleic acids useful in the methods described herein have at least 80% sequence complementarity to a target region within the target nucleic acid, e.g., 90%, 95%, or 100% sequence complementarity to the target region within an target sequence. For example, an antisense compound in which 18 of 20 nucleobases of the antisense oligonucleotide are complementary, and would therefore specifically hybridize, to a target region would represent 90 percent complementarity. Percent complementarity of an inhibitory nucleic acid with a region of a target nucleic acid can be determined routinely using basic local alignment search tools (BLAST programs) (Altschul et al., J. Mol. Biol., 1990, 215, 403-410; Zhang and Madden, Genome Res., 1997, 7, 649-656). Antisense and other compounds of the invention that hybridize to an target sequence are identified through routine experimentation. In general the inhibitory nucleic acids must retain specificity for their target, i.e., must not directly bind to, or directly significantly affect expression levels of, transcripts other than the intended target.

For further disclosure regarding inhibitory nucleic acids, please see US2010/0317718 (antisense oligos); US2010/0249052 (double-stranded ribonucleic acid (dsRNA)); US2009/0181914 and US2010/0234451 (LNAs); US2007/0191294 (siRNA analogues); US2008/0249039 (modified siRNA); and WO2010/129746 and WO2010/040112 (inhibitory nucleic acids).

Antisense

In some embodiments, the inhibitory nucleic acids are antisense oligonucleotides. Antisense oligonucleotides are typically designed to block expression of a DNA or RNA target by binding to the target and halting expression at the level of transcription, translation, or splicing. Antisense oligonucleotides of the present invention are complementary nucleic acid sequences designed to hybridize under stringent conditions to an target sequence. Thus, oligonucleotides are chosen that are sufficiently complementary to the target, i.e., that hybridize sufficiently well and with sufficient specificity, to give the desired effect.

Modified Bases/Locked Nucleic Acids (LNAs)

In some embodiments, the inhibitory nucleic acids used in the methods described herein comprise one or more modified bonds or bases. Modified bases include phosphorothioate, methylphosphonate, peptide nucleic acids, or locked nucleic acid (LNA) molecules. Preferably, the modified nucleotides are locked nucleic acid molecules, including [alpha]-LNAs. LNAs comprise ribonucleic acid analogues wherein the ribose ring is "locked" by a methylene bridge between the 2'-oxgygen and the 4'-carbon—i.e., oligonucleotides containing at least one LNA monomer, that is, one 2'-O,4'-C-methylene-β-D-ribofuranosyl nucleotide. LNA bases form standard Watson-Crick base pairs but the locked configuration increases the rate and stability of the basepairing reaction (Jepsen et al., Oligonucleotides, 14, 130-146 (2004)). LNAs also have increased affinity to base pair with RNA as compared to DNA. These properties render LNAs especially useful as probes for fluorescence in situ hybridization (FISH) and comparative genomic hybridization, as knockdown tools for miRNAs, and as antisense oligonucleotides to target mRNAs or other RNAs, e.g., target sequences as described herien.

The LNA molecules can include molecules comprising 10-30, e.g., 12-24, e.g., 12, 13, 14, 15, 16, 17, 18, 19, 20, 21, 22, 23, 24, 25, 26, 27, 28, 29, or 30 nucleotides in each strand, wherein one of the strands is substantially identical, e.g., at least 80% (or more, e.g., 85%, 90%, 95%, or 100%) identical, e.g., having 3, 2, 1, or 0 mismatched nucleotide(s), to a target region in the target sequence. The LNA molecules can be chemically synthesized using methods known in the art.

The LNA molecules can be designed using any method known in the art; a number of algorithms are known, and are commercially available (e.g., on the internet, for example at exiqon.com). See, e.g., You et al., Nuc. Acids. Res. 34:e60 (2006); McTigue et al., Biochemistry 43:5388-405 (2004); and Levin et al., Nuc. Acids. Res. 34:e142 (2006). For example, "gene walk" methods, similar to those used to design antisense oligos, can be used to optimize the inhibitory activity of the LNA; for example, a series of oligonucleotides of 10-30 nucleotides spanning the length of a target sequence can be prepared, followed by testing for activity. Optionally, gaps, e.g., of 5-10 nucleotides or more, can be left between the LNAs to reduce the number of oligonucleotides synthesized and tested. GC content is preferably between about 30-60%. General guidelines for designing LNAs are known in the art; for example, LNA sequences will bind very tightly to other LNA sequences, so it is preferable to avoid significant complementarity within an LNA. Contiguous runs of three or more Gs or Cs, or more than four LNA residues, should be avoided where possible (for example, it may not be possible with very short (e.g., about 9-10 nt) oligonucleotides). In some embodiments, the LNAs are xylo-LNAs.

In some embodiments, the LNA molecules can be designed to target a specific region of the target sequence. For example, a specific functional region can be targeted, e.g., a region comprising a known RNA localization motif (i.e., a region complementary to the target nucleic acid on which the target sequence acts), or a region comprising a known protein binding region, e.g., a Polycomb (e.g., Polycomb Repressive Complex 2 (PRC2), comprised of H3K27 methylase EZH2, SUZ12, and EED)) or LSD1/CoREST/REST complex binding region (see, e.g., Tsai et al., Science. 2010 Aug. 6; 329 (5992):689-93. Epub 2010 Jul. 8; and Zhao et al., Science. 2008 Oct. 31; 322(5902):750-6). Sarma et al., "Locked nucleic acids (LNAs) reveal sequence requirements and kinetics of Xist RNA localization to the X chromosome." PNAS published ahead of print Dec. 6, 2010, doi:10.1073/pnas.1009785107. Alternatively or in addition, highly conserved regions can be targeted, e.g., regions identified by aligning sequences from disparate species such as primate (e.g., human) and rodent (e.g., mouse) and looking for regions with high degrees of identity. Percent identity can be determined routinely using basic local alignment search tools (BLAST programs) (Altschul et al., J. Mol. Biol., 1990, 215, 403-410; Zhang and Madden, Genome Res., 1997, 7, 649-656), e.g., using the default parameters.

For additional information regarding LNAs see U.S. Pat. Nos. 6,268,490; 6,734,291; 6,770,748; 6,794,499; 7,034,133; 7,053,207; 7,060,809; 7,084,125; and 7,572,582; and U.S. Pre-Grant Pub. Nos. 20100267018; 20100261175; and 20100035968; Koshkin et al. Tetrahedron 54, 3607-3630 (1998); Obika et al. Tetrahedron Lett. 39, 5401-5404 (1998); Jepsen et al., Oligonucleotides 14:130-146 (2004); Kauppinen et al., Drug Disc. Today 2(3):287-290 (2005); and Ponting et al., Cell 136(4):629-641 (2009), and references cited therein.

See also U.S. Ser. No. 61/412,862, which is incorporated by reference herein in its entirety.

Antagomirs

In some embodiments, the antisense is an antagomir. Antagomirs are chemically modified antisense oligonucleotides that target an target sequence. For example, an antagomir for use in the methods described herein can include a nucleotide sequence sufficiently complementary to hybridize to an target sequence target sequence of about 12 to 25 nucleotides, preferably about 15 to 23 nucleotides.

In general, antagomirs include a cholesterol moiety, e.g., at the 3'-end. In some embodiments, antagomirs have various modifications for RNase protection and pharmacologic properties such as enhanced tissue and cellular uptake. For example, In addition to the modifications discussed above for antisense oligos, an antagomir can have one or more of complete or partial 2'-O-methylation of sugar and/or a phosphorothioate backbone. Phosphorothioate modifications provide protection against RNase activity and their lipophilicity contributes to enhanced tissue uptake. In some embodiments, the antagomir can include six phosphorothioate backbone modifications; two phosphorothioates are located at the 5'-end and four at the 3'-end. See, e.g., Krutzfeldt et al., Nature 438, 685-689 (2005); Czech, N Engl J Med 2006; 354:1194-1195 (2006); Robertson et al., Silence. 1:10 (2010); Marquez and McCaffrey, Hum Gene Ther. 19(1):27-38 (2008); van Rooij et al., Circ Res. 103(9):919-928 (2008); and Liu et al., Int. J. Mol. Sci. 9:978-999 (2008). Antagomirs useful in the present methods can also be modified with respect to their length or otherwise the number of nucleotides making up the antagomir. The antagomirs must retain specificity for their target, i.e., must not directly bind to, or directly significantly affect expression levels of, transcripts other than the intended target.

In some embodiments, the inhibitory nucleic acid is locked and includes a cholesterol moiety (e.g., a locked antagomir).

siRNA/shRNA

In some embodiments, the nucleic acid sequence that is complementary to an target sequence can be an interfering RNA, including but not limited to a small interfering RNA ("siRNA") or a small hairpin RNA ("shRNA"). Methods for constructing interfering RNAs are well known in the art. For example, the interfering RNA can be assembled from two separate oligonucleotides, where one strand is the sense strand and the other is the antisense strand, wherein the antisense and sense strands are self-complementary (i.e., each strand comprises nucleotide sequence that is complementary to nucleotide sequence in the other strand; such as where the antisense strand and sense strand form a duplex or double stranded structure); the antisense strand comprises nucleotide sequence that is complementary to a nucleotide sequence in a target nucleic acid molecule or a portion thereof (i.e., an undesired gene) and the sense strand comprises nucleotide sequence corresponding to the target nucleic acid sequence or a portion thereof. Alternatively, interfering RNA is assembled from a single oligonucleotide, where the self-complementary sense and antisense regions are linked by means of nucleic acid based or non-nucleic acid-based linker(s). The interfering RNA can be a polynucleotide with a duplex, asymmetric duplex, hairpin or asymmetric hairpin secondary structure, having self-complementary sense and antisense regions, wherein the antisense region comprises a nucleotide sequence that is complementary to nucleotide sequence in a separate target nucleic acid molecule or a portion thereof and the sense region having nucleotide sequence corresponding to the target nucleic acid sequence or a portion thereof. The interfering can be a circular single-stranded polynucleotide having two or more loop structures and a stem comprising self-complementary sense and antisense regions, wherein the antisense region comprises nucleotide sequence that is complementary to nucleotide sequence in a target nucleic acid molecule or a portion thereof and the sense region having nucleotide sequence corresponding to the target nucleic acid sequence or a portion thereof, and wherein the circular polynucleotide can be processed either in vivo or in vitro to generate an active siRNA molecule capable of mediating RNA interference.

In some embodiments, the interfering RNA coding region encodes a self-complementary RNA molecule having a sense region, an antisense region and a loop region. Such an RNA molecule when expressed desirably forms a "hairpin" structure, and is referred to herein as an "shRNA." The loop region is generally between about 2 and about 10 nucleotides in length. In some embodiments, the loop region is from about 6 to about 9 nucleotides in length. In some embodiments, the sense region and the antisense region are between about 15 and about 20 nucleotides in length. Following post-transcriptional processing, the small hairpin RNA is converted into a siRNA by a cleavage event mediated by the enzyme Dicer, which is a member of the RNase III family. The siRNA is then capable of inhibiting the expression of a gene with which it shares homology. For details, see Brummelkamp et al., Science 296:550-553, (2002); Lee et al, Nature Biotechnol., 20, 500-505, (2002); Miyagishi and Taira, Nature Biotechnol 20:497-500, (2002); Paddison et al. Genes & Dev. 16:948-958, (2002); Paul, Nature Biotechnol, 20, 505-508, (2002); Sui, Proc. Natl. Acad. Sd. USA, 99(6), 5515-5520, (2002); Yu et al. Proc Natl Acad Sci USA 99:6047-6052, (2002).

The target RNA cleavage reaction guided by siRNAs is highly sequence specific. In general, siRNA containing a nucleotide sequences identical to a portion of the target nucleic acid are preferred for inhibition. However, 100% sequence identity between the siRNA and the target gene is not required to practice the present invention. Thus the invention has the advantage of being able to tolerate sequence variations that might be expected due to genetic mutation, strain polymorphism, or evolutionary divergence. For example, siRNA sequences with insertions, deletions, and single point mutations relative to the target sequence have also been found to be effective for inhibition. Alternatively, siRNA sequences with nucleotide analog substitutions or insertions can be effective for inhibition. In general the siRNAs must retain specificity for their target, i.e., must not directly bind to, or directly significantly affect expression levels of, transcripts other than the intended target.

Ribozymes

Trans-cleaving enzymatic nucleic acid molecules can also be used; they have shown promise as therapeutic agents for human disease (Usman & McSwiggen, 1995 Ann. Rep. Med. Chem. 30, 285-294; Christoffersen and Marr, 1995 J. Med. Chem. 38, 2023-2037). Enzymatic nucleic acid molecules can be designed to cleave specific target sequences within the background of cellular RNA. Such a cleavage event renders the target sequence non-functional.

In general, enzymatic nucleic acids with RNA cleaving activity act by first binding to a target RNA. Such binding occurs through the target binding portion of a enzymatic nucleic acid which is held in close proximity to an enzymatic portion of the molecule that acts to cleave the target RNA. Thus, the enzymatic nucleic acid first recognizes and then binds a target RNA through complementary base pairing, and once bound to the correct site, acts enzymatically to cut the target RNA. Strategic cleavage of such a target RNA will destroy its ability to direct synthesis of an encoded protein. After an enzymatic nucleic acid has bound and cleaved its RNA target, it is released from that RNA to search for another target and can repeatedly bind and cleave new targets.

Several approaches such as in vitro selection (evolution) strategies (Orgel, 1979, Proc. R. Soc. London, B 205, 435) have been used to evolve new nucleic acid catalysts capable of catalyzing a variety of reactions, such as cleavage and ligation of phosphodiester linkages and amide linkages, (Joyce, 1989, Gene, 82, 83-87; Beaudry et al., 1992, Science 257, 635-641; Joyce, 1992, Scientific American 267, 90-97; Breaker et al, 1994, TIBTECH 12, 268; Bartel et al, 1993, Science 261: 1411-1418; Szostak, 1993, TIBS 17, 89-93; Kumar et al, 1995, FASEB J., 9, 1183; Breaker, 1996, Curr. Op. Biotech., 1, 442). The development of ribozymes that are optimal for catalytic activity would contribute significantly to any strategy that employs RNA-cleaving ribozymes for the purpose of regulating gene expression. The hammerhead ribozyme, for example, functions with a catalytic rate (kcat) of about 1 $min^{-1}$ in the presence of saturating (10 mM) concentrations of $Mg^{2+}$ cofactor. An artificial "RNA ligase" ribozyme has been shown to catalyze the corresponding self-modification reaction with a rate of about 100 $min^{-1}$. In addition, it is known that certain modified hammerhead ribozymes that have substrate binding arms made of DNA catalyze RNA cleavage with multiple turn-over rates that approach 100 $min^{-1}$.

Making and Using Inhibitory Nucleic Acids

The nucleic acid sequences used to practice the methods described herein, whether RNA, cDNA, genomic DNA, vectors, viruses or hybrids thereof, can be isolated from a variety of sources, genetically engineered, amplified, and/or expressed/generated recombinantly. Recombinant nucleic acid sequences can be individually isolated or cloned and tested for a desired activity. Any recombinant expression system can be used, including e.g. in vitro, bacterial, fungal, mammalian, yeast, insect or plant cell expression systems.

Nucleic acid sequences of the invention can be inserted into delivery vectors and expressed from transcription units within the vectors. The recombinant vectors can be DNA plasmids or viral vectors. Generation of the vector construct can be accomplished using any suitable genetic engineering techniques well known in the art, including, without limitation, the standard techniques of PCR, oligonucleotide synthesis, restriction endonuclease digestion, ligation, transformation, plasmid purification, and DNA sequencing, for example as described in Sambrook et al. Molecular Cloning: A Laboratory Manual. (1989)), Coffin et al. (Retroviruses. (1997)) and "RNA Viruses: A Practical Approach" (Alan J. Cann, Ed., Oxford University Press, (2000)). As will be apparent to one of ordinary skill in the art, a variety of suitable vectors are available for transferring nucleic acids of the invention into cells. The selection of an appropriate vector to deliver nucleic acids and optimization of the conditions for insertion of the selected expression vector into the cell, are within the scope of one of ordinary skill in the art without the need for undue experimentation. Viral vectors comprise a nucleotide sequence having sequences for the production of recombinant virus in a packaging cell. Viral vectors expressing nucleic acids of the invention can be constructed based on viral backbones including, but not limited to, a retrovirus, lentivirus, adenovirus, adeno-associated virus, pox virus or alphavirus. The recombinant vectors capable of expressing the nucleic acids of the invention can be delivered as described herein, and persist in target cells (e.g., stable transformants).

Nucleic acid sequences used to practice this invention can be synthesized in vitro by well-known chemical synthesis techniques, as described in, e.g., Adams (1983) J. Am. Chem. Soc. 105:661; Belousov (1997) Nucleic Acids Res. 25:3440-3444; Frenkel (1995) Free Radic. Biol. Med. 19:373-380; Blommers (1994) Biochemistry 33:7886-7896; Narang (1979) Meth. Enzymol. 68:90; Brown (1979) Meth. Enzymol. 68:109; Beaucage (1981) Tetra. Lett. 22:1859; U.S. Pat. No. 4,458,066.

Nucleic acid sequences of the invention can be stabilized against nucleolytic degradation such as by the incorporation of a modification, e.g., a nucleotide modification. For example, nucleic acid sequences of the invention includes a phosphorothioate at least the first, second, or third internucleotide linkage at the 5' or 3' end of the nucleotide sequence. As another example, the nucleic acid sequence can include a 2'-modified nucleotide, e.g., a 2'-deoxy, 2'-deoxy-2'-fluoro, 2'-O-methyl, 2'-O-methoxyethyl (2'-O-MOE), 2'-O-aminopropyl (2'-O-AP), 2'-O-dimethylaminoethyl (2'-O-DMAOE), 2'-O-dimethylaminopropyl (2'-O-DMAP), 2'-O-dimethylaminoethyloxyethyl (2'-O-DMAEOE), or 2'-O—N-methylacetamido (2'-O-NMA). As another example, the nucleic acid sequence can include at least one 2'-O-methyl-modified nucleotide, and in some embodiments, all of the nucleotides include a 2'-O-methyl modification. In some embodiments, the nucleic acids are "locked," i.e., comprise nucleic acid analogues in which the ribose ring is "locked" by a methylene bridge connecting the 2'-O atom and the 4'-C atom (see, e.g., Kaupinnen et al., Drug Disc. Today 2(3):287-290 (2005); Koshkin et al., J. Am. Chem. Soc., 120(50): 13252-13253 (1998)). For additional modifications see US 20100004320, US 20090298916, and US 20090143326.

Techniques for the manipulation of nucleic acids used to practice this invention, such as, e.g., subcloning, labeling probes (e.g., random-primer labeling using Klenow polymerase, nick translation, amplification), sequencing, hybridization and the like are well described in the scientific and patent literature, see, e.g., Sambrook et al., *Molecular Cloning; A Laboratory Manual* 3d ed. (2001); *Current Protocols in Molecular Biology*, Ausubel et al., eds. (John Wiley & Sons, Inc., New York 2010); Kriegler, *Gene Transfer and Expression: A Laboratory Manual* (1990); *Laboratory Techniques In Biochemistry And Molecular Biology: Hybridization With Nucleic Acid Probes, Part I. Theory and Nucleic Acid Preparation*, Tijssen, ed. Elsevier, N.Y. (1993).

Pharmaceutical Compositions

The methods described herein can include the administration of pharmaceutical compositions and formulations comprising inhibitors of TLR3 and/or TLR7, including inhibitory nucleic acid sequences designed to target a target sequence (i.e., TLR3 or TLR7).

In some embodiments, the compositions are formulated with a pharmaceutically acceptable carrier. The pharmaceutical compositions and formulations can be administered parenterally, topically, orally or by local administration, such as by aerosol or transdermally. The pharmaceutical compositions can be formulated in any way and can be administered in a variety of unit dosage forms depending upon the condition or disease and the degree of illness, the general medical condition of each patient, the resulting preferred method of administration and the like. Details on techniques for formulation and administration of pharmaceuticals are well described in the scientific and patent literature, see, e.g., *Remington: The Science and Practice of Pharmacy*, 21st ed., 2005.

The TLR3/7 inhibitors, e.g., inhibitory nucleic acids, can be administered alone or as a component of a pharmaceutical formulation (composition). The compounds may be formulated for administration, in any convenient way for use in human or veterinary medicine. Wetting agents, emulsifiers and lubricants, such as sodium lauryl sulfate and magnesium stearate, as well as coloring agents, release agents, coating agents, sweetening, flavoring and perfuming agents, preservatives and antioxidants can also be present in the compositions.

Formulations of the compositions of the invention include those suitable for intradermal, inhalation, oral/nasal, topical, parenteral, rectal, and/or intravaginal administration. The formulations may conveniently be presented in unit dosage form and may be prepared by any methods well known in the art of pharmacy. The amount of active ingredient (e.g., nucleic acid sequences of this invention) which can be combined with a carrier material to produce a single dosage form will vary depending upon the host being treated, the particular mode of administration, e.g., intradermal or inhalation. The amount of active ingredient which can be combined with a carrier material to produce a single dosage form will generally be that amount of the compound which produces a therapeutic effect, e.g., an antigen specific T cell or humoral response.

Pharmaceutical formulations useful in the methods described herein can be prepared according to any method known to the art for the manufacture of pharmaceuticals. Such drugs can contain sweetening agents, flavoring agents, coloring agents and preserving agents. A formulation can be admixtured with nontoxic pharmaceutically acceptable excipients which are suitable for manufacture. Formulations may comprise one or more diluents, emulsifiers, preservatives, buffers, excipients, etc. and may be provided in such forms as liquids, powders, emulsions, lyophilized powders, sprays, creams, lotions, controlled release formulations, tablets, pills, gels, on patches, in implants, etc.

Pharmaceutical formulations for oral administration can be formulated using pharmaceutically acceptable carriers well known in the art in appropriate and suitable dosages. Such carriers enable the pharmaceuticals to be formulated in unit dosage forms as tablets, pills, powder, dragees, capsules, liquids, lozenges, gels, syrups, slurries, suspensions, etc., suitable for ingestion by the patient. Pharmaceutical preparations for oral use can be formulated as a solid excipient, optionally grinding a resulting mixture, and processing the mixture of granules, after adding suitable additional compounds, if desired, to obtain tablets or dragee cores. Suitable solid excipients are carbohydrate or protein fillers include, e.g., sugars, including lactose, sucrose, mannitol, or sorbitol; starch from corn, wheat, rice, potato, or other plants; cellulose such as methyl cellulose, hydroxypropylmethyl-cellulose, or sodium carboxy-methylcellulose; and gums including arabic and tragacanth; and proteins, e.g., gelatin and collagen. Disintegrating or solubilizing agents may be added, such as the cross-linked polyvinyl pyrrolidone, agar, alginic acid, or a salt thereof, such as sodium alginate. Push-fit capsules can contain active agents mixed with a filler or binders such as lactose or starches, lubricants such as talc or magnesium stearate, and, optionally, stabilizers. In soft capsules, the active agents can be dissolved or suspended in suitable liquids, such as fatty oils, liquid paraffin, or liquid polyethylene glycol with or without stabilizers.

Aqueous suspensions can contain an active agent (e.g., nucleic acid sequences of the invention) in admixture with excipients suitable for the manufacture of aqueous suspensions, e.g., for aqueous intradermal injections. Such excipients include a suspending agent, such as sodium carboxymethylcellulose, methylcellulose, hydroxypropylmethylcellulose, sodium alginate, polyvinylpyrrolidone, gum tragacanth and gum acacia, and dispersing or wetting agents such as a naturally occurring phosphatide (e.g., lecithin), a condensation product of an alkylene oxide with a fatty acid (e.g., polyoxyethylene stearate), a condensation product of ethylene oxide with a long chain aliphatic alcohol (e.g., heptadecaethylene oxycetanol), a condensation product of ethylene oxide with a partial ester derived from a fatty acid and a hexitol (e.g., polyoxyethylene sorbitol mono-oleate), or a condensation product of ethylene oxide with a partial ester derived from fatty acid and a hexitol anhydride (e.g., polyoxyethylene sorbitan mono-oleate). The aqueous suspension can also contain one or more preservatives such as ethyl or n-propyl p-hydroxybenzoate, one or more coloring agents, one or more flavoring agents and one or more sweetening agents, such as sucrose, aspartame or saccharin. Formulations can be adjusted for osmolarity.

In some embodiments, oil-based pharmaceuticals are used for administration of nucleic acid sequences of the invention. Oil-based suspensions can be formulated by suspending an active agent in a vegetable oil, such as arachis oil, olive oil, sesame oil or coconut oil, or in a mineral oil such as liquid paraffin; or a mixture of these. See e.g., U.S. Pat. No. 5,716,928 describing using essential oils or essential oil components for increasing bioavailability and reducing inter- and intra-individual variability of orally administered hydrophobic pharmaceutical compounds (see also U.S. Pat. No. 5,858,401). The oil suspensions can contain a thickening agent, such as beeswax, hard paraffin or cetyl alcohol. Sweetening agents can be added to provide a palatable oral preparation, such as glycerol, sorbitol or sucrose. These formulations can be preserved by the addition of an antioxidant such as ascorbic acid. As an example of an injectable oil vehicle, see Minto (1997) J. Pharmacol. Exp. Ther. 281:93-102.

Pharmaceutical formulations can also be in the form of oil-in-water emulsions. The oily phase can be a vegetable oil or a mineral oil, described above, or a mixture of these. Suitable emulsifying agents include naturally-occurring gums, such as gum acacia and gum tragacanth, naturally occurring phosphatides, such as soybean lecithin, esters or partial esters derived from fatty acids and hexitol anhydrides, such as sorbitan mono-oleate, and condensation products of these partial esters with ethylene oxide, such as polyoxyethylene sorbitan mono-oleate. The emulsion can also contain sweetening agents and flavoring agents, as in the formulation of syrups and elixirs. Such formulations can also contain a demulcent, a preservative, or a coloring agent. In alternative embodiments, these injectable oil-in-water emulsions of the invention comprise a paraffin oil, a sorbitan monooleate, an ethoxylated sorbitan monooleate and/or an ethoxylated sorbitan trioleate.

The pharmaceutical compounds can also be administered by in intranasal, intraocular and intravaginal routes including suppositories, insufflation, powders and aerosol formulations (for examples of steroid inhalants, see e.g., Rohatagi (1995) J. Clin. Pharmacol. 35:1187-1193; Tjwa (1995) Ann. Allergy Asthma Immunol. 75:107-111). Suppositories formulations can be prepared by mixing the drug with a suitable non-irritating excipient which is solid at ordinary temperatures but liquid at body temperatures and will therefore melt in the body to release the drug. Such materials inlcude cocoa butter and polyethylene glycols.

In some embodiments, the pharmaceutical compounds can be delivered transdermally, by a topical route, formulated as applicator sticks, solutions, suspensions, emulsions, gels, creams, ointments, pastes, jellies, paints, powders, and aerosols.

In some embodiments, compositions comprising an inhibitor of TLR3/7 for transdermal/topical application can further comprise cosmetically-acceptable carriers or vehicles and any optional components. A number of such cosmetically acceptable carriers, vehicles and optional components are known in the art and include carriers and vehicles suitable for application to skin (e.g., sunscreens, creams, milks, lotions, masks, serums, etc.), see, e.g., U.S. Pat. Nos. 6,645,512 and 6,641,824. In particular, optional components that may be desirable include, but are not limited to absorbents, anti-acne actives, anti-caking agents, anti-cellulite agents, anti-foaming agents, anti-fungal actives, anti-inflammatory actives, anti-microbial actives, anti-oxidants, antiperspirant/deodorant actives, anti-skin atrophy actives, anti-viral agents, anti-wrinkle actives, artificial tanning agents and accelerators, astringents, barrier repair agents, binders, buffering agents, bulking agents, chelating agents, colorants, dyes, enzymes, essential oils, film formers, flavors, fragrances, humectants, hydrocolloids, light diffusers, nail enamels, opacifying agents, optical brighteners, optical modifiers, particulates, perfumes, pH adjusters, sequestering agents, skin conditioners/moisturizers, skin feel modifiers, skin protectants, skin sensates, skin treating agents, skin exfoliating agents, skin lightening agents, skin soothing and/or healing agents, skin thickeners, sunscreen actives, topical anesthetics, vitamin compounds, and combinations thereof.

In some embodiments, the pharmaceutical compounds can also be delivered as microspheres for slow release in the body. For example, microspheres can be administered via intradermal injection of drug which slowly release subcutaneously; see Rao (1995) J. Biomater Sci. Polym. Ed. 7:623-645; as biodegradable and injectable gel formulations, see, e.g., Gao (1995) Pharm. Res. 12:857-863 (1995); or, as microspheres for oral administration, see, e.g., Eyles (1997) J. Pharm. Pharmacol. 49:669-674.

In some embodiments, the pharmaceutical compounds can be parenterally administered, such as by intravenous (IV) administration or administration into a body cavity or lumen of an organ. These formulations can comprise a solution of active agent dissolved in a pharmaceutically acceptable carrier. Acceptable vehicles and solvents that can be employed are water and Ringer's solution, an isotonic sodium chloride. In addition, sterile fixed oils can be employed as a solvent or suspending medium. For this purpose any bland fixed oil can be employed including synthetic mono- or diglycerides. In addition, fatty acids such as oleic acid can likewise be used in the preparation of injectables. These solutions are sterile and generally free of undesirable matter. These formulations may be sterilized by conventional, well known sterilization techniques. The formulations may contain pharmaceutically acceptable auxiliary substances as required to approximate physiological conditions such as pH adjusting and buffering agents, toxicity adjusting agents, e.g., sodium acetate, sodium chloride, potassium chloride, calcium chloride, sodium lactate and the like. The concentration of active agent in these formulations can vary widely, and will be selected primarily based on fluid volumes, viscosities, body weight, and the like, in accordance with the particular mode of administration selected and the patient's needs. For IV administration, the formulation can be a sterile injectable preparation, such as a sterile injectable aqueous or oleaginous suspension. This suspension can be formulated using those suitable dispersing or wetting agents and suspending agents. The sterile injectable preparation can also be a suspension in a nontoxic parenterally-acceptable diluent or solvent, such as a solution of 1,3-butanediol. The administration can be by bolus or continuous infusion (e.g., substantially uninterrupted introduction into a blood vessel for a specified period of time).

In some embodiments, the pharmaceutical compounds and formulations can be lyophilized. Stable lyophilized formulations comprising an inhibitory nucleic acid can be made by lyophilizing a solution comprising a pharmaceutical of the invention and a bulking agent, e.g., mannitol, trehalose, raffinose, and sucrose or mixtures thereof. A process for preparing a stable lyophilized formulation can include lyophilizing a solution about 2.5 mg/mL protein, about 15 mg/mL sucrose, about 19 mg/mL NaCl, and a sodium citrate buffer having a pH greater than 5.5 but less than 6.5. See, e.g., U.S. 20040028670.

The compositions and formulations can be delivered by the use of liposomes. By using liposomes, particularly where the liposome surface carries ligands specific for target cells, or are otherwise preferentially directed to a specific organ, one can focus the delivery of the active agent into target cells in vivo. See, e.g., U.S. Pat. Nos. 6,063,400; 6,007,839; Al-Muhammed (1996) J. Microencapsul. 13:293-306; Chonn (1995) Curr. Opin. Biotechnol. 6:698-708; Ostro (1989) Am. J. Hosp. Pharm. 46:1576-1587. As used in the present invention, the term "liposome" means a vesicle composed of amphiphilic lipids arranged in a bilayer or bilayers. Liposomes are unilamellar or multilamellar vesicles that have a membrane formed from a lipophilic material and an aqueous interior that contains the composition to be delivered. Cationic liposomes are positively charged liposomes that are believed to interact with negatively charged DNA molecules to form a stable complex. Liposomes that are pH-sensitive or negatively-charged are believed to entrap DNA rather than complex with it. Both cationic and noncationic liposomes have been used to deliver DNA to cells.

Liposomes can also include "sterically stabilized" liposomes, i.e., liposomes comprising one or more specialized lipids. When incorporated into liposomes, these specialized lipids result in liposomes with enhanced circulation lifetimes relative to liposomes lacking such specialized lipids. Examples of sterically stabilized liposomes are those in which part of the vesicle-forming lipid portion of the liposome comprises one or more glycolipids or is derivatized with one or more hydrophilic polymers, such as a polyethylene glycol (PEG) moiety. Liposomes and their uses are further described in U.S. Pat. No. 6,287,860.

The formulations of the invention can be administered for prophylactic and/or therapeutic treatments. In some embodiments, for therapeutic applications, compositions are administered to a subject who is in need of reduced triglyceride levels, or who is at risk of or has a disorder described herein, in an amount sufficient to cure, alleviate or partially arrest the clinical manifestations of the disorder or its complications; this can be called a therapeutically effective amount. For example, in some embodiments, pharmaceutical compositions of the invention are administered in an amount sufficient to decrease serum levels of triglycerides in the subject.

The amount of pharmaceutical composition adequate to accomplish this is a therapeutically effective dose. The dosage schedule and amounts effective for this use, i.e., the dosing regimen, will depend upon a variety of factors, including the stage of the disease or condition, the severity of the disease or condition, the general state of the patient's health, the patient's physical status, age and the like. In calculating the dosage regimen for a patient, the mode of administration also is taken into consideration.

The dosage regimen also takes into consideration pharmacokinetics parameters well known in the art, i.e., the active agents' rate of absorption, bioavailability, metabolism, clearance, and the like (see, e.g., Hidalgo-Aragones (1996) J. Steroid Biochem. Mol. Biol. 58:611-617; Groning (1996) Pharmazie 51:337-341; Fotherby (1996) Contraception 54:59-69; Johnson (1995) J. Pharm. Sci. 84:1144-1146; Rohatagi (1995) Pharmazie 50:610-613; Brophy (1983) Eur. J. Clin. Pharmacol. 24:103-108; *Remington: The Science and Practice of Pharmacy,* 21st ed., 2005). The state of the art allows the clinician to determine the dosage regimen for each individual patient, active agent and disease or condition treated. Guidelines provided for similar compositions used as pharmaceuticals can be used as guidance to determine the dosage regiment, i.e., dose schedule and dosage levels, administered practicing the methods of the invention are correct and appropriate.

Single or multiple administrations of formulations can be given depending on for example: the dosage and frequency as required and tolerated by the patient, the degree and amount of therapeutic effect generated after each administration (e.g., effect on tumor size or growth), and the like. The formulations should provide a sufficient quantity of active agent to effectively treat, prevent or ameliorate conditions, diseases or symptoms.

In alternative embodiments, pharmaceutical formulations for oral administration are in a daily amount of between about 1 to 100 or more mg per kilogram of body weight per day. Lower dosages can be used, in contrast to administration orally, into the blood stream, into a body cavity or into a lumen of an organ. Substantially higher dosages can be used in topical or oral administration or administering by powders, spray or inhalation. Actual methods for preparing parenterally or non-parenterally administrable formulations will be known or apparent to those skilled in the art and are described in more detail in such publications as *Remington: The Science and Practice of Pharmacy,* 21st ed., 2005.

Various studies have reported successful mammalian dosing using complementary nucleic acid sequences. For example, Esau C. et al., (2006) Cell Metabolism, 3(2):87-98 reported dosing of normal mice with intraperitoneal doses of miR-122 antisense oligonucleotide ranging from 12.5 to 75 mg/kg twice weekly for 4 weeks. The mice appeared healthy and normal at the end of treatment, with no loss of body weight or reduced food intake. Plasma transaminase levels were in the normal range (AST ¾ 45, ALT ¾ 35) for all doses with the exception of the 75 mg/kg dose of miR-122 ASO, which showed a very mild increase in ALT and AST levels. They concluded that 50 mg/kg was an effective, non-toxic dose. Another study by Kriitzfeldt J., et al., (2005) Nature 438, 685-689, injected anatgomirs to silence miR-122 in mice using a total dose of 80, 160 or 240 mg per kg body weight. The highest dose resulted in a complete loss of miR-122 signal. In yet another study, locked nucleic acids ("LNAs") were successfully applied in primates to silence miR-122. Elmen J., et al., (2008) Nature 452, 896-899, report that efficient silencing of miR-122 was achieved in primates by three doses of 10 mg kg-1 LNA-antimiR, leading to a long-lasting and reversible decrease in total plasma cholesterol without any evidence for LNA-associated toxicities or histo-pathological changes in the study animals.

In some embodiments, the methods described herein can include co-administration with other drugs or pharmaceuticals, e.g., compositions for providing itch relief or for soothing or healing irritated or damaged skin. For example, the TLR3/7 inhibitors can be co-administered with one or more anti-histaminics (e.g., promethazine or chloropromazine); μ-receptor antagonists (e.g., naloxone or naltrexone); gabapentin, paroxetine; amitryptiline; or anti-oxidative stress compounds (such as vitamin E), e.g., as a topical preparation. In the case of chloroquine-induced pruritus, the TLR3/7 inhibitors can be administered with one or more antihistamines (e.g., promethazine or chloropromazine); μ-receptor antagonists (e.g., naltrexone); prednisolone; or Niacin. In the case of opioid-induced pruritus, the inhibitors may be co-administered with an opioid antagonist, e.g., naloxone, naltrexone or nalbuphine; dopamine (D2) receptor antagonist (e.g., droperidol, alizapride); serotonin (5-HT3) receptor antagonists (e.g., ondansetron, dolasetron); sedating antihistaminics (e.g., promethazine, diphenhydramine); or cyclooxygenase-1 inhibitors (e.g., tenoxicam, diclofenac). In the case of Hydroxyethyl starch-induced pruritus, the inhibitors may be co-administered with one or more of naloxone or naltrexone; phototherapy; or topical capsaicin. In the case of pruritus secondary to cholestatic liver disease, the inhibitors may be co-administered with one or more of ursodeoxycholic acid; rifampicin; cholestyramine; μ-receptor antagonists (e.g., naloxone, naltrexone); or sertraline.

EXAMPLES

The invention is further described in the following examples, which do not limit the scope of the invention described in the claims.

The following materials and methods were used in Examples 1-9.

Mice

We used adult mice (25-32 g) for behavioral and histochemical studies. Tlr3 knockout mice (B6; 129S1-Tlr3tm1Flv/J) and wild-type mice of the same genetic background (B6129SF1/J) were purchased from the Jackson Laboratories and bred at Harvard Thorn Building Animal Facility with water and food available ad libitum. A targeting vector containing a loxP site flanked neomycin resistance cassette and a herpes simplex virus thymidine kinase gene was used to disrupt exon 1. The construct was electroporated into 129S1/Sv-p$^+$ Tyr$^+$ Kitl$^{Sl-J}$ derived W9.5 embryonic stem (ES) cells. Correctly targeted ES cells were injected into C57BL/6 blastocysts, and the resulting chimeric male mice were crossed to female C57BL/6 mice. Heterozygotes were intercrossed to generate homozygotes. Homozygous mice are viable, fertile, have normal in size and, and do not display any gross physical or behavioral abnormalities (1). We also obtained Tlr2$^{-/-}$ mice (B6; 129-Tlr2tm1Kir/J), Tlr4$^{-/-}$ (B6.B10ScN-Tlr4lps-del/JthJ) mice, Tlr7$^{-/-}$ (B6.129S1-Tlr7tm1Flv/J) mice, and wild-type (C57BL/6J) control mice, from Jackson Laboratories. CD1 mice, purchased from Charles River, were also used for some behavioral and pharmacological studies. All animal protocols performed in this study were reviewed and approved by the Harvard Medical Area Standing Committee on Animals.

Drugs and Administration

We injected pruritic agents intradermally in the nape of the neck (50 μl) or cheek (10 μl), respectively. We purchased histamine, compound 48/80, trypsin, chloroquine, serotonin, TLR3 agonist polyribo-inosinic/cytidylic acid (PIC), and complete Freund's adjuvant (CFA) from Sigma-Aldrich, histamine H1 receptor agonist histamine-trifluoromethyl-toluidine (HTMT), capsaicin, and the H4R-selective agonist 4-methylhistamine (4-MeHA) from Tocris, and endothelin-1 (ET-1) from ALEXIS Biochemicals. We also purchased the PAR2 agonist H-Ser-Leu-Ile-Gly-Arg-Leu-NH2 (SLIGRL-NH2) and gastrin-releasing peptide fragment (GRP$_{18-27}$) from Bachem, and TRIF peptide inhibitor and control peptide from Invivogen. Antisense oligodeoxynucleotides (AS-ODN; 5'-AACAATTGCTTCAAGTCC-3'; SEQ ID NO:1) targeting TLR3 and mismatch ODN (MM-ODN; 5'-ACTAC-TACACTAGACTAC-3'; SEQ ID NO:2) were synthesized by Invitrogen according to the published sequences (2). AS-ODN (10 μg) or MM-ODN were intrathecally injected once a day for 5 days. To target DRG and spinal cord cells, TRIF inhibitor (10 μl) were delivered intrathecally into cerebral spinal fluid via a lumbar puncture. A successful spinal puncture was evidenced by a brisk tail-flick after the needle entry into subarachnoid space (3). Most reagents were dissolved in sterile saline. Capsaicin was dissolved in 10% DMSO.

Behavioral Analysis

All of the behavioral tests were done in strict sex- and age-matched adult mice by the observers blinded to the treatment or genotype of the animals. Mice were habituated to the testing environment daily for at least two days before analysis. The experiments were performed in accordance with the guidelines of the National Institutes of Health and the International Association for the Study of Pain. The animal room was artificially illuminated from 7:00 am to 7:00 pm. Itch and pain behavioral testing in mice models was performed as previously described (34).

Itch Behavioral Testing

Mice were habituated to the testing environment daily for at least two days before analysis. <ice were shaved at the back of the neck the day before injection. We put mice in small plastic chambers (14×18×12 cm) on an elevated metal mesh floor and allowed 30 min for habituation before examination. We injected 50 μl of pruritic agent intradermally in the nape of the neck and counted the number of scratches every 5 min for 30 min after the injection. A scratch was counted when a mouse lifted its hindpaw to scratch the shaved region and returned the paw to the floor or to the mouth for licking. On the basis of previous reports (4; 5) and our preliminary studies (6), we chose the following doses for pruritic agents: 25 ng for ET-1, 20 μg for 5-HT, 100 μg for HTMT, compound 48/80, and SLIGRL-NH2, 200 μg for chloroquine, 300 μg for trypsin, and 500 μg for histamine and 4-MeHA. We also injected diluted formalin (0.6%, 50 μl) in the nape to induce scratching behaviors. The experimenters were blinded to the genotypes of the animals. We also produced a dry skin model for chronic itch as described in detail previously (7), by painting neck skin with acetone and diethyether (1:1) following by water (AEW) twice a day for 7 days, and examined spontaneous itch by counting the number of scratches for 60 minutes on day 8 and 9.

Cheek Model

To distinguish itch and pain responses simultaneously, we used the cheek model by injection of chemical into cheek of mice (8). After brief anesthesia with isoflurane, we shaved mice on cheeks (approx. 5×8 mm area) two days before experiments. On the day of experiment, we injected 10 μl of reagent (50 μg compound 48/80 or 100 μg chloroquine) into the cheek and counted the number of wipes and the number of scratches for 30 min. We only counted those unilateral wipes with the forelimb that were not part of grooming behavior. One scratch was defined as a lifting of the hind paw toward the injection site on the cheek and then returning the paw to the floor or to the mouth.

Pain Behavioral Testing

We habituate animals to the testing environment daily for at least two days before baseline testing. The all behavioral experimenters were done by individuals that were blinded to the treatment or genotypes of the mice.

Randall-Selitto Test.

We used Randall-Selitto Analgesy-meter to examine mechanical sensitivity by applying ascending pressure to the tail of a mouse and determined the mechanical pain threshold when animal showed a clear sign of discomfort or escape, with a cutoff threshold of 250 g to avoid tissue damage (9).

Hot Water Immersion Test.

We used hot water immersion test to assess heat pain sensitivity by keeping the tail of a mouse in hot water at 48, 50, or 52° C. and recorded the tail flick latency with a cutoff time of 10 seconds.

Capsaicin Test.

Capsaicin (1 and 10 μg in 20 μl 2.5% DMSO) was intraplantarly injected into one hindpaw, and the number of flinches was counted for the first 5 min.

Mustard Oil Test.

Mustard oil (1 and 10 μg in 20 μl saline) was injected into the plantar surface of one hindpaw, and the duration of licking and flinching of the injected paw for the first 5 minutes.

Formalin Test.

Formalin (5% in 20 μl saline) was injected into the plantar surface of the left hind paw and the duration of licking and flinching was measured in 5 minute bins for 45 minutes after formalin injection (10).

Complete Freund Adjuvant (CFA) Model.

To produce persistent inflammatory pain, 20 μl CFA was injected unilaterally into the plantar surface of the hindpaw in mice (11).

Mechanical hypersensitivity (mechanical allodynia) was assessed via manual application of a set of calibrated von Frey filaments to the plantar surface and thermal hypersensitivity (heat hyperalgesia) was assessed by determining the latency of paw withdrawal in response to radiant heat as described previously (12). Briefly, for von Frey testing, we put mice in boxes on an elevated metal mesh floor and stimulated hindpaw with a series of von Frey hairs with logarithmically incrementing stiffness (0.02-2.56 grams, Stoelting), presented perpendicular to the plantar surface, and determined the 50% paw withdrawal threshold using up-down method (13).

Primary and Secondary Mechanical Hypersensitivity Induced by Capsaicin.

Capsaicin (5 μg in 10 μl 2.5% DMSO) was intraplantarly injected into one hindpaw, and primary and secondary mechanical hypersensitivity was assessed via manual application of a set of calibrated von Frey filaments to the injected site (primary) or surrounding area (secondary) (14).

Motor Function Testing

A rotarod system was used to assess the coordinate motor function. Mice were tested for three trails separated by 10 min intervals and during the tests, the speed of rotation was accelerated from 2 to 20 r.p.m. in 3 min. the falling latency was recorded and averaged (15).

RT-PCR

Total RNAs were isolated from spleen, DRGs, brain and spinal cord of WT and Tlr3$^{-/-}$ mice with the RNeasy Mini Kit (QIAGEN) and quantified using A260/A280 absorption. The first-strand cDNA were synthesized with Oligo(dT)$_{12-18}$ primer using SuperScript™ II Reverse Transcriptase (Invitrogen). Mouse PCR primers were designed as follows:

```
TLR3:
sense
                                            (SEQ ID NO: 3)
5'-CTCTGATGGCTTTGGCTACT-3' antisense
                                            (SEQ ID NO: 4)
5'-GATGTTGAACAGGAAGTCGG-3'

GAPDH:
sense
                                            (SEQ ID NO: 5)
5'-GAAGGGTGGAGCCAAAAGG-3' antisense
                                            (SEQ ID NO: 6)
5'-AAGGTGGAAGAGTGGGAGTT-3'
```

GAPDH were used as an internal control. cDNA samples were amplified for 25-35 cycles by Taq DNA Polymerase (Invitrogen), and PCR products were separated on agarose gel. Gel image were captured in Gel Document System (Bio-Rad).

Single-Cell RT-PCR

Single-cell RT-PCR was performed as previously described (17). Briefly, a single cell was aspirated into a patch pipette with a tip diameter of about 25 μm, gently put into a reaction tube containing reverse transcription reagents, and incubated for 1 hour at 50° C. (superscript III, Invitrogen, Carlsbad, Calif., USA). The cDNA product was used in separate PCR. The sequences of all the primers used for single-cell PCR are described in Table 1 below. The first round of PCR was performed in 50 μl of PCR buffer containing 0.2 mM dNTPs, 0.2 μM "outer" primers, 5 μl RT product and 0.2 μl platinum Taq DNA polymerase (Invitrogen). The protocol included a 5 min initial denaturation step at 95° C. followed by 40 cycles of 40 s denaturation at 95° C., 40 s annealing at 55° C., 40 s elongation at 72° C. The reaction was completed with 7 minutes of final elongation. For the second round of amplification, the reaction buffer (20 μl) contained 0.2 mM dNTPs, 0.2 μM "inner" primers, 5 μl of the first round PCR products and 0.1 μl platinum Taq DNA polymerase. The reaction procedure for these primers was the same as the first round. A negative control was obtained from pipettes that did not harvest any cell contents, but were submerged in the bath solution. The PCR products were displayed on ethidium bromide-stained 1% agarose gels. See Table 1 for the sequences of the primers.

TABLE 1

Target Gene - Genbank No.

| Product Length (bp) Outer Primers | SEQ ID NO: | Product Length (bp) Inner Primers | SEQ ID NO: |
|---|---|---|---|
| TRPV1 - Genbank No. NM_001001445.1 | | | |
| 273 TGATCATCTTCACCACGGCTG CCTTGCGATGGCTGAAGTACA | 10 11 | 203 AAGGCTTGCCCCCCTATAA CACCAGCATGAACAGTGACT GT | 24 25 |
| GRP - Genbank No. NM_175012.2 | | | |
| 258 CCAAGGAGCAAAACAAAACCC GCAAATTGGAGCCCTGAATCT | 12 13 | 201 AGACTGCCTTCTGCAAACGTC AAGCCTAGCTGGAAAAAGCG | 26 27 |
| GAPDH - Genbank No. XM_001473623.1 | | | |
| 367 AGCCTCGTCCCGTAGACAAAA TTTTGGCTCCACCCCTTCA | 14 15 | 313 TGAAGGTCGGTGTGAACGAA TT GCTTTCTCCATGGTGGTGAA GA | 28 29 |
| TLR2 - Genbank No. NM_011905.3 | | | |
| 388 TCTTGGAATGTCACCAGGCTG TCGCTCCGTACGAAGTTCTCA | 16 17 | 311 TGTGCCCTTCTCCTGTTGAT CT GTTTTGTGGCTCTTTTCGAT GG | 30 31 |
| TLR3 - Genbank No. NM_126166.4 | | | |
| 477 CCAGTTCCTTTGCATTGGTCC GCCCGAAAACATCCTTCTCAA | 18 19 | 269 CAGCCTTCAAAGACTGATGC TC GATTTCATCTAAGCCGTTGG AC | 32 33 |
| TLR4 - Genbank No. NM_021297.2 | | | |
| 368 GTGTAGCCATTGCTGCCAACA GGTCCAAGTTGCCGTTTCTTG | 20 21 | 301 TCATCCAGGAAGGCTTCCA TTCGAGGCTTTTCCATCCA | 34 35 |
| TLR7 - Genbank No. NM_133211.3 | | | |
| 421 CAGTGAACTCTGGCCGTTGAGA TGGCGGCATACCCTCAAAA | 22 23 | 359 TTCTCCAACAACCGGCTTGAT TCAGGAGGCAAGGAATTCAGG | 36 37 |

Primary Culture of DRG Neurons

DRGs were removed aseptically from 4-week old mice and first incubated with collagenase (1.25 mg/ml, Roche)/dispase-II (2.4 units/ml, Roche) at 37° C. for 90 min, then digested with 0.25% trypsin (Cellgro) for 8 min at 37° C., followed by 0.25% trypsin inhibitor (Sigma). Cells were then mechanically dissociated with a flame polished Pasteur pipette in the presence of 0.05% DNAse I (Sigma). DRG cells were plated onto poly-D-lysine and laminin-coated slide chambers (for immunocytochemistry) or glass cover slips (for electrophysiology) and grown in a neurobasal defined medium (with 2% B27 supplement, Invitrogen) in the presence of 5 μM AraC, at 36.5° C., with 5% carbon dioxide.

Real-Time Quantitative RT-PCR

We collected back hairy skin and cervical DRGs from 4 pairs of WT and Tlr3$^{-/-}$ mice and isolated total RNAs using RNeasy Plus Mini kit (Qiagen, Valencia, Calif.). One microgram of RNA was reverse transcribed for each sample using Omniscript reverse transcriptase according to the protocol of the manufacturer (Qiagen). Sequences for the forward and reverse primers for TLR2, TLR3, TLR4, TLR7, Tryptase, Chymases, CD117 and NGF are described in Table 2. Triplicate qPCR analyses were performed using the Opticon real-time PCR Detection System (Bio-Rad, Hercules, Calif.) as described previously (16).

TABLE 2

List of primer sequences designed for quantitative real-time RT-PCR
Target Gene - Genbank No.

| Forward Primer | SEQ ID NO: | Reverse Primer | SEQ ID NO: |
|---|---|---|---|
| GAPDH - XM_001473623.1 | | | |
| TCC ATG ACA ACT TTG GCA TTG | 38 | CAG TCT TCT GGG TGG CAG TGA | 50 |
| TLR2 - NM_011905.3 | | | |
| ACA ACT TAC CGA AAC CTC AGA | 39 | ACC CCA GAA GCA TCA CAT G | 51 |
| TLR3 - NM_126166.4 | | | |
| GCG TTG CGA AGT GAA GAA CT | 40 | TTC AAG AGG AGG GCG AAT AA | 52 |
| TLR4 - NM_021297.2 | | | |
| TTC AGA ACT TCA GTG GCT GG | 41 | TGT TAG TCC AGA GAA ACT TCC TG | 53 |
| TLR7 -. NM_133211.3 | | | |
| TTT GTC TCT TCC GTG TCC AC | 42 | GAT GTC CTT GGC TCC CTTT C | 54 |

TABLE 2-continued

List of primer sequences designed for quantitative real-time RT-PCR
Target Gene - Genbank No.

| Forward Primer | SEQ ID NO: | Reverse Primer | SEQ ID NO: |
|---|---|---|---|
| TRPV1 -. NM_001001445.1 | | | |
| ATG TTC GTC TAC CTC GTG TTC TTG | 43 | AGG CAG TGA GTT ATT CTT CCC ATC C | 55 |
| TAC1 (SP) - NM_009311 | | | |
| AGG CTC TTT ATG GAC ATG GC | 44 | TCT TTC GTA GTT CTG CAT CGC | 56 |
| TNF alpha - NM_013693 | | | |
| CCC CAA AGG GAT GAG AAG TT | 45 | CAC TTG GTG GTT TGC TAC GA | 57 |
| NGF - NM_013609 | | | |
| CCC AAT AAA GGT TTT GCC AAG G | 46 | TTG CTA TCT GTG TAC GGT TCT G | 58 |
| TPSAB1 - NM_031187 | | | |
| ATT TCT GAC TAT GTC CAC CCT G | 47 | AAT GGG AAC TTG CAC CTC C | 59 |
| CMA1 - NM_010780 | | | |
| CAC TTC TGA GAA CTA CCT GTC G | 48 | TGT TTT GTT A TG GGC TCC TAG G | 60 |
| KIT (CD117) - NM_021099 | | | |
| TGT GGC TAA AGA TGA ACC CTC | 49 | ACA CTC CAG AAT CGT CAA CTC | 61 |

Triplicate qPCR analyses were performed using the Opticon real-time PCR Detection System (Bio-Rad, Hercules, Calif.) as described previously (56). Following treatment of AEW 7 day in WT and Tlr3 knockout mice, the treated skin and cervical DRGs were collected for Real-time quantitative PCR analysis for TLR3, NGF and TNF-α.

Patch-Clamp Recordings in Dissociated DRG Neurons

Single-cell RT-PCR was performed as previously described (6). DRG cultures were prepared as above described and grown on glass cover slips coated with poly-D-lysine and laminin. Whole-cell patch clamp recordings were performed at room temperature to measure currents in dissociated DRG neurons with small-sizes using Axopatch-200B amplifier (Axon Instruments, Union City, USA). The patch pipettes were pulled from borosilicate capillaries (Chase Scientific Glass Inc., Rockwood, Calif., USA). When filled with the pipette solution, the resistance of the pipettes was 4~5 MΩ. The recording chamber (volume 300 μl) was continuously superfused (3-4 ml/min). Series resistance was compensated for (>80%), and leak subtraction was performed. Data were low-pass-filtered at 2 KHz, sampled at 10 KHz. The pClamp8 (Axon Instruments) software was used during experiments and analysis. The pipette solution was composed of (in mM): 126 K-gluconate, 10 NaCl, 1 MgCl$_2$, 10 EGTA, 2 NaATP, 0.1 MgGTP, pH 7.3 with KOH, 295-300 mOsm. Extracellular solution contained (in mM): 140 NaCl, 5 KCl, 2 CaCl$_2$, 1 MgCl$_2$, 10 HEPES, 10 glucose adjusted to pH 7.4 with NaOH, osmolarity 310 mOsm. Inward currents were recorded at a holding potential of −60 mV. In some experiments, following parch-clamp recording, the recorded DRG neurons were collected for single-cell RT-PCR analysis.

Spinal Cord Slice Preparation and Patch Clamp Recordings

As we previously reported (18), a portion of the lumbar spinal cord (L4-L5) was removed from mice (4-6 week old) under urethane anesthesia (1.5-2.0 g/kg, i.p.) and kept in pre-oxygenated ice-cold Krebs solution. Transverse slices (600 μm) were cut on a vibrating microslicer. The slices were perfused with Kreb's solution (8-10 ml/min) that was saturated with 95% O$_2$ and 5% CO$_2$ at 36±1° C. for at least 1-3 hours prior to experiment. The Kreb's solution contains (in mM): NaCl 117, KCl 3.6, CaCl$_2$ 2.5, MgCl$_2$ 1.2, NaH$_2$PO$_4$ 1.2, NaHCO$_3$ 25, and glucose 11.

The whole cell patch-clamp recordings were made from lamina IIo neurons in voltage clamp mode. Patch pipettes were fabricated from thin-walled, borosilicate, glass-capillary tubing (1.5 mm o.d., World Precision Instruments). After establishing the whole-cell configuration, neurons were held at the potential of −70 mV to record sEPSCs. The resistance of a typical patch pipette is 5-10 M. The internal solution contains (in mM): potassium gluconate 135, KCl 5, CaCl$_2$ 0.5, MgCl$_2$ 2, EGTA 5, HEPES 5, ATP-Mg 5. Membrane currents were amplified with an Axopatch 200B amplifier (Axon Instruments) in voltage-clamp mode. Signals were filtered at 2 kHz and digitized at 5 kHz. Data were stored with a personal computer using pCLAMP 10 software and analyzed with Mini Analysis (Synaptosoft Inc.).

Spinal Cord LTP Recordings in Anesthetized Mice

Mice were anesthetized with urethane (1.5 g/kg, IP). The trachea was cannulated to allow mechanical ventilation, if necessary. PBS (0.5-1 ml, i.p.) was injected prior to surgery and every 2 hours after surgery to maintain electrolyte balance. A laminectomy was performed at vertebrae T13-L1 to expose the lumbar enlargement, and the left sciatic nerve was exposed for bipolar electrical stimulation. The vertebral column was firmly suspended by rostral and caudal clamps on the stereotaxic frame. The exposed spinal cord and the sciatic nerve were covered with paraffin oil. Colorectal temperature was kept constant at 37-38° C. by a feedback-controlled heating blanket. Following electrical stimulation of the sciatic nerve, the field potentials were recorded in the ipsilateral L4-5 spinal cord segments with glass microelectrodes, 100-300 μm from the surface of the cord. In vivo LTP was recorded as previously reported (19) with some modifications for mice. After recording stable responses following test stimuli (2× C-fiber threshold, 0.5 ms, 1 min interval, every 5 min) for >40 min, conditioning tetanic stimulation (5 times of C-fiber threshold, 100 Hz, 1 s, 10 s interval) was delivered to the sciatic nerve for inducing LTP of C-fiber-evoked field potentials. For intrathecal drug delivery, a PE5 catheter was inserted at L5-L6 level via lumbar puncture.

In Situ Hybridization

Mice were terminally anesthetized with isoflurane and transcardially perfused with PBS and 4% paraformaldehyde. DRGs were collected and post-fixed overnight. DRG tissues were sectioned in a cryostat at a thickness of 12 μm and mounted on Superfrost plus slides. Two separate TLR3 riboprobes (0.34 and 0.76 kb) and a riboprobe for pan-neuronal marker SCG10 were generated by PCR. The reverse primer contains T7 RNA polymerase binding sequence (TG-TAATACGACTCACTATAGGGCG (SEQ ID NO:7)) for the generation of the antisense riboprobe. DNA sequences were transcribed in vitro with T7 RNA polymerase (Promega) in the presence of digoxigenin-labeling mix. In situ hybridization was performed as we previously described (20; 21). Briefly, sections were hybridized with TLR3 riboprobe (1 μg/ml) or SCG10 riboprobe (1 μg/ml) overnight at 65° C. After washing, sections were blocked with 20% serum for 1 h at room temperature followed by incubation with alkaline phosphatase-conjugated anti-digoxigen antibody (1:2000; Roche Diagnostics) overnight at 4° C. Sections were then incubated with a mixture of nitro-blue tetrazolium (NBT) and 5-bromo-4-chloro-3-indolyl-phosphate (BCIP) in alkaline phosphatase buffer for 24-48 h for color development. In situ hybridization images were captured with a Nikon microscope under bright-field.

Immunohistochemistry

Mice were terminally anesthetized with isoflurane and perfused through the ascending aorta with saline followed by 4% paraformaldehyde. We collected DRG, dorsal root, sciatic nerve and spinal cord tissues and postfixed these tissues in the same fixative overnight. Tissue sections were cut in a cryostat and processed for immunofluorescence. Tissue sections were blocked with 2% goat serum, and incubated over night at 4° C. with the following primary antibodies against TLR3 (rabbit, 1:500, Santa Cruz), TRPV1 (Guinea pig, 1:1000, Neuromics), GRP (rabbit, 1:300, Immunostar), and Substance P (guinea pig, 1:1000, Neuromics). The sections were then incubated for 1 h at room temperature with Cy3- or FITC-conjugated secondary antibodies. For double immunofluorescence, sections were incubated with a mixture of polyclonal and monoclonal primary antibodies followed by a mixture of FITC- and CY3-congugated secondary antibodies (22). Immunostained tissue sections were examined under a Nikon fluorescence microscope, and images were captured with a high resolution CCD Spot camera (Diagnostic Instruments Inc.) and analyzed with NIH Image software or Adobe PhotoShop.

To enhance the signal of GRP immunostaining, TSA (Tyramide Signal Amplification) kit (Perkin Elmer, Mass.) was used for some tissue sections. In brief, after the primary antibody incubation, the sections were incubated with a biotinylated-secondary antibody (1:400, 1 h at room temperature), followed by avidin-streptin incubation (1:100, 1 hour at room temperature), and finally by tyramide incubation (1:50, 5 min at room temperature).

We also performed immunostaining on cultured DRG neurons. DRG cultures were prepared as above described and were grown in slide chambers for 24 hours and fixed with 4% paraformaldehyde for 30 min. Cells were then incubated with a mixture of primary antibodies of TLR3 (rabbit, Santa Cruz, 1:500) and TRPV1 (guinea pig, 1:500, Chemicon), or EEA1 (mouse, Abcam, 1:100) or RAB7 (rabbit, Santa Cruz, 1:200) overnight, following by a mixture of Cy3- and FITC-conjugated secondary antibodies. Images were visualized and analysis using fluorescence microscope (Nikon) or confocal microscope (LSM 510 META, Carl Zeiss MicroImaging Inc.).

To determine pruritogen-induced Fos expression in spinal cord, 2 hours after intradermal injection of pruritogens (compound 48/80 or chloroquine), the mice were terminally anesthetized with isoflurane and perfused through the ascending aorta with saline followed by 4% paraformaldehyde. Cervical spinal cord was collected and postfixed these tissues in the same fixative overnight. Tissue sections were cut in a cryostat at 30 μm and blocked with 2% goat serum, and incubated over night at 4° C. with the following primary antibodies against Fos (rabbit, 1:500, Santa Cruz). The sections were then incubated for 1 hour at room temperature with Cy3-conjugated secondary antibodies. Immunostained tissue sections were examined under a Nikon fluorescence microscope, and images were captured with a high resolution CCD Spot camera (Diagnostic Instruments Inc.) and analyzed with NIH Image software or Adobe PhotoShop.

Calcium Imaging from Cultured DRG Neurons

DRGs from all spinal levels of 4-week old mice were collected in cold DH10 (90% DMEM/F-12, 10% FBS, 100 U/ml penicillin, and 100 μg/ml Streptomycin, Gibco) and treated with enzyme solution (5 mg/ml Dispase, 1 mg/ml Collagenase Type I in HPBS without $Ca^{++}$ and $Mg^{++}$, Gibco) at 37° C. Following trituration and centrifugation, cells were resuspended in DH10, plated on glass cover slips coated with poly-D-lysine (0.5 mg/ml, Stoughton, Mass.) and laminin (10 μg/ml, Invitrogen), cultured in an incubator (95% $O_2$ and 5% $CO_2$) at 37° C. and used within 24 hours. Neurons were loaded with Fura 2-acetomethoxy ester (Molecular Probes) for 30 min in the dark at room temperature. After washing, cells were imaged at 340 and 380 nm excitation to detect intracellular free calcium. To compare the response to histamine, chloroquine, and capsaicin between WT and Tlr3-deficient DRG neurons, calcium imaging assays were performed with an experimenter blind to genotype (n=3 per genotype), and the percentages of DRG neurons showing calcium responses were determined as we previously described (23).

Histology

Mice were terminally anesthetized with isoflurane and the back hairy skin and hindpaw skin was collected from 4 pairs of wild-type and Tlr3 knockout to perform histological examination. Tissues were postfixed in 4% paraformaldehyde overnight and were cut in a cryostat at 14 μm. The sections were stained with toluidine blue (TB) for mast cells staining and hematoxylin & eosin (H&E) staining for hair follicle examine, and then dried, cleared and covered for observation and photomicrography. The number of mast cells and hair follicles was quantified by individuals that are blinded for the genotype using ten sections per mouse from four mice.

Quantification

To quantify if there are changes in neurochemical markers and loss of neurons in the DRGs of Tlr3 deficient mice, L4/L5 lumbar DRGs were dissected from 4 pairs of mutant and control mice, and eight adjacent sections at 12-μm thickness were prepared from each DRG. Each set was processed for immunostaining (CGRP, NF-200, and P2×3). Only those neurons showing nuclei and distinct staining above the background were counted. This semiquantification does not determine the total number of neurons, but rather a percentage.

Histamine Measurement

Mice were terminally anesthetized with isoflurane and the back hairy skin was collected from 4 pairs of WT and Tlr3$^{-/-}$ mice to measure the histamine content. Histamine was quantified using a histamine Enzyme Immunoassay kit (Oxford Biomedical Research) according to the manufacture's manual. Histamine was also measured in skins after AEW treatment in WT and Tlr3$^{-/-}$ mice. We also measured histamine release in skin organ cultures after treatment of compound 48/80.

Western Blotting

Mice were terminally anesthetized with isoflurane and transcardially perfused with PBS, and the DRGs were rapidly removed and homogenized in a lysis buffer containing a cocktail of protease inhibitors and phosphatase inhibitors. The protein concentrations were determined by BCA Protein Assay (Pierce), and 30 μg of proteins were loaded for each lane and separated on SDS-PAGE gel (4-15%, Bio-Rad). After the transfer, the blots were incubated overnight at 4° C. with polyclonal antibody against TLR-3 (rabbit, 1:500, Imgenex). For loading control, the blots were probed with GAPDH antibody (rabbit, 1:10000, Sigma).

Statistics

All the data are expressed as mean±SEM. Most data were analyzed with Student's t-test (two groups between WT and KO mice) to determine statistically significant differences. Two-Way repeated measured ANOVA were also used to analyze the data with multiple time points (e.g., data of LTP and time course of itch behavior). The criterion for statistical significance was P<0.05.

Example 1

Tlr3$^{-/-}$ Mice have Intact Acute Nociceptive Pain but Impaired Central Sensitization-Driven Pain To determine the role of TLR3 in pain sensation, multiple behavioral tests of pain were performed in mice lacking TLR3 (Tlr3$^{-/-}$) (39).

Consistent with previous reports (39), we did not observe any gross anatomical defects in Tlr3$^{-/-}$ mice, as compared with wild-type (WT) control mice (Supplemental FIG. 1A). Tail immersion test in hot water at 48, 50, and 52° C. showed that Tlr3$^{-/-}$ and WT mice had similar response latency, suggesting intact thermal sensitivity in Tlr3$^{-/-}$ mice (FIG. 1A). Randall-Selitto test demonstrated that Tlr3$^{-/-}$ and WT mice also had comparable tail withdrawal threshold (FIG. 1B). To evaluate chemical algesic-induced pain, we made intraplantar injection of capsaicin (TRPV1 agonist), or mustard oil (TRPA1 agonist). Tlr3$^{-/-}$ mice showed indistinguishable spontaneous flinching/licking behaviors in response to capsaicin (FIG. 1C) and mustard oil (FIG. 1D). To evaluate motor function in Tlr3$^{-/-}$ mice, mice were submitted to Rotarod test. The falling latency of Tlr3$^{-/-}$ mice was similar to that of WT mice, indicating there is no motor coordinating deficiency in Tlr3$^{-/-}$ mice (FIG. 1E). We also assessed persistent inflammatory pain by intraplantar injection of complete Freund's adjuvant (CFA). CFA induced comparable heat hyperalgesia and mechanical allodynia in WT and Tlr3$^{-/-}$ mice (P>0.05) (Supplemental FIG. 1B).

Next, we examined formalin (5%)-induced biphasic spontaneous pain in Tlr3$^{-/-}$ and WT mice. While the $1^{st}$ phase response is due to acute activation of peripheral nociceptors, the $2^{nd}$ phase response is attributed to activity-dependent central sensitization and ongoing afferent input (35). Notably, the $2^{nd}$-phase but not the $1^{st}$-phase responses were significantly decreased in Tlr3$^{-/-}$ mice (P<0.05, compared with WT mice, Student's t test) (FIG. 1F). We also tested capsaicin-induced primary and secondary mechanical hyperalgesia, which is caused by peripheral and central sensitization, respectively (38). Capsaicin-induced secondary but not primary mechanical hyperalgesia was reduced in Tlr3$^{-/-}$ mice (P<0.05, compared with WT mice, Student's t test) (FIG. 1G). Together, our data suggest that TLR3 is required for central sensitization-driven pain hypersensitivity but not required for acute nociceptive pain and peripheral sensitization.

Tlr3$^{-/-}$ Mice Display Impaired Histamine-Dependent and Independent Itch.

Figures 2A, 2B:
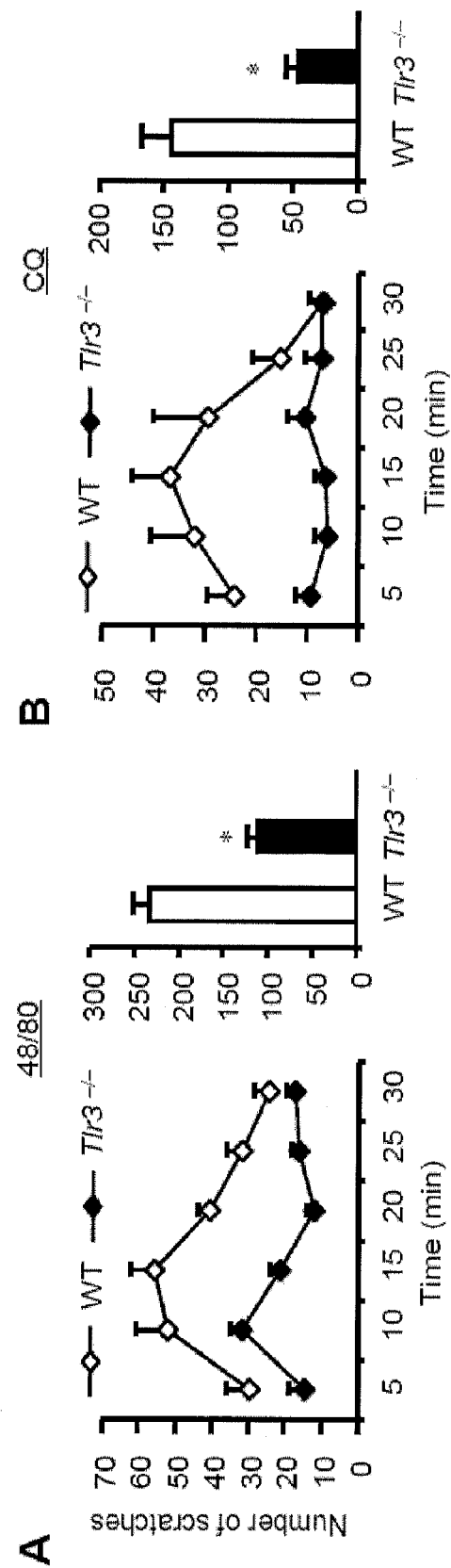
FIGS. 2A-C are a series of graphs and photomicrographs showing impaired scratching behaviors and reduced c-Fos expression in the spinal cord in Tlr3$^{-/-}$ mice.

Increasing evidence suggests distinct molecular mechanisms of pain and itch (1). To determine whether TLR3 is involved in itch sensation, we examined scratching behaviors in Tlr3$^{-/-}$ and WT mice following intradermal injection of histamine-dependent and independent pruritic agents into the nape of the neck of mice. While compound 48/80 induces histamine-dependent itch, via releasing histamine from mast cells, chloroquine induces histamine-independent itch via activation of MrgprA3 (11). Compared to WT mice, Tlr3$^{-/-}$ mice exhibited a dramatic reduction in scratching behaviors evoked by compound 48/80 (P<0.05, Two-way repeated measures ANOVA) (FIG. 2A) and chloroquine (P<0.05, Two-way repeated measures ANOVA) (FIG. 2B). Compound 48/80-induced scratches were reduced in both male and female Tlr3$^{-/-}$ mice.

Figure 2C:
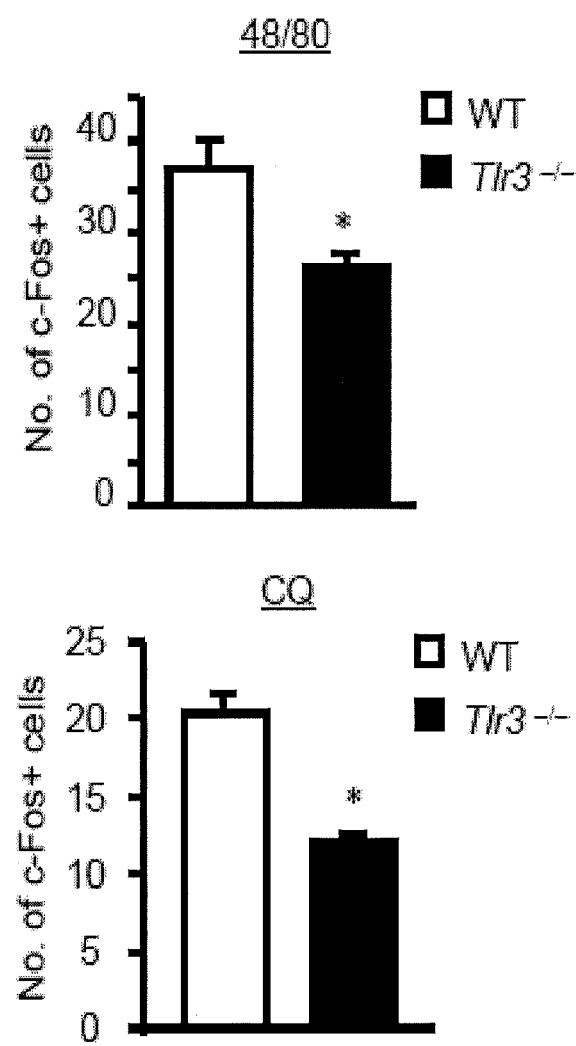

Spinal c-Fos expression was widely used as a functional marker of neuronal activation after pruritic stimuli (40). C-Fos expression in dorsal horn neurons, induced by both compound 48/80 and chloroquine, was significantly decreased in Tlr3$^{-/-}$ mice (P<0.05, compared to WT mice, Student's t test) (FIG. 2C). These data suggest that both itch behaviors and pruritogens-induced spinal neuronal activation were impaired in Tlr3$^{-/-}$ mice.

We also tested other histaminergic pruritogens-induced itch behaviors in Tlr3$^{-/-}$ mice, including histamine, HTMT (histamine H1 receptor agonist), and 4-MeHA (histamine H4 receptor agonist). Scratching elicited by these pruritogens was also significantly reduced in Tlr3$^{-/-}$ mice (P<0.05, Two-way repeated measures ANOVA) (FIGS. 9A-C). Further, scratching induced by endothelin-1 and serotonin, as well as nonhistaminergic pruritogens SLIGRL-NH2 (41; 42) and trypsin, was abrogated in Tlr3$^{-/-}$ mice (P<0.05, Two-way ANOVA, repeated measures) (FIGS. 9D-G).

Finally, we tested scratching by low concentration of formalin (0.6%) (21) and the TLR7 agonist imiquimod, which was shown to induce itch via TLR7-dependent and independent mechanisms (34; 43). Both formalin and imiquimod-induced scratches were substantially reduced in Tlr3$^{-/-}$ mice (P<0.05, Two-way ANOVA, repeated measures) (FIGS. 9H-I) In parallel, an accumulated analysis of scratching in 30 min further confirmed that all forms of itch mentioned above were substantially decreased in Tlr3$^{-/-}$ mice (P<0.05, Student's t test) (FIG. 9J). Thus, TLR3 is indispensible for the full expression of itch behaviors in mice, regardless of the histamine dependency. By contrast, Tlr2$^{-/-}$ mice and Tlr4$^{-/-}$ mice exhibited comparable scratching responses to compound 48/80 and chloroquine (P>0.05) (FIGS. 10A,B).

Example 2

TLRs are Differently Involved in Pain and Itch in a Cheek Model

Figures 3A, 3B, 3C, 3D:
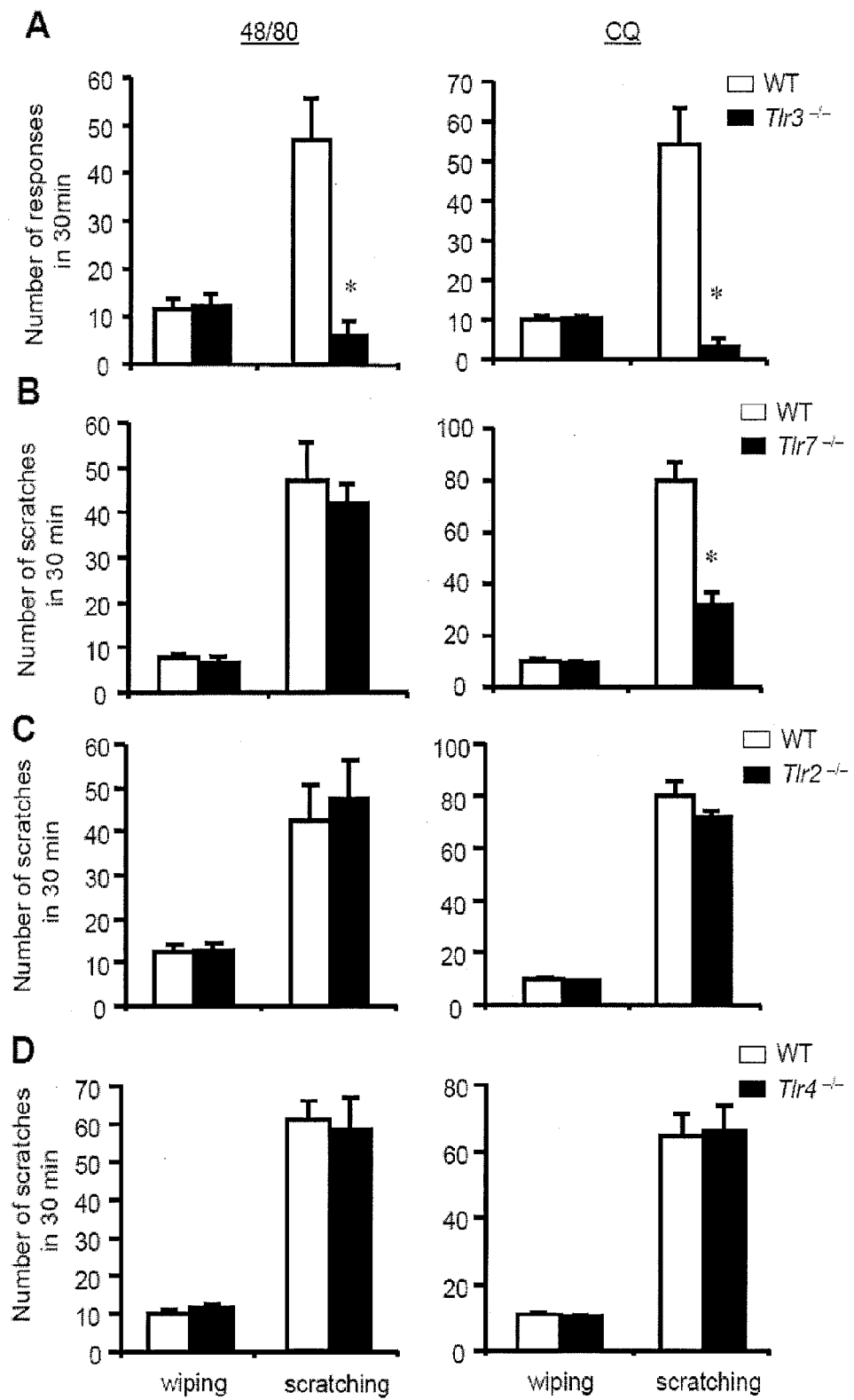
FIGS. 3A-3D are a series of eight bar graphs showing distinct roles of TLRs in regulating pain and itch in mouse cheek model. Intradermal injection of 48/80 (50 μg) and CQ (100 μg) in the cheek induces either pain-indicative wiping by forelimbs or itch-like scratching by the hind limb.

To further determine the distinct roles of TLRs in pain and itch, we used a recently developed cheek model that can distinguish pain versus itch (44; 45). In this model, intradermal injection of algesic or pruritogenic reagents in the cheek induces pain-indicative wiping by forelimbs and itch-like scratching by the hind limbs, respectively (44; 45). Tlr3$^{-/-}$ mice displayed a dramatic reduction in compound 48/80 and chloroquine-induced scratching behavior (P<0.05, Student's t test) (FIG. 3A), but unaltered wiping behavior (FIG. 3A), again supporting a role of TLR3 in itch but not acute nociception. Interestingly, Tlr7$^{-/-}$ mice only showed a reduction in chloroquine-induced scratching (P<0.05, Student's t test) (FIG. 3B) but no changes in wiping behavior and compound 48/80-induced scratching behaviors (FIG. 3B). These results support our previous observations that TLR7 is only involved in histamine-independent itch (34). Notably, Tlr2$^{-/-}$ and Tlr4$^{-/-}$ mice showed normal wiping and scratching behaviors induced by both compound 48/80 and chloroquine (FIGS. 3C; D).

Example 3

TLR3 is Expressed in a Subset of DRG Neurons of Adult Mice

Figures 4A, 4B:
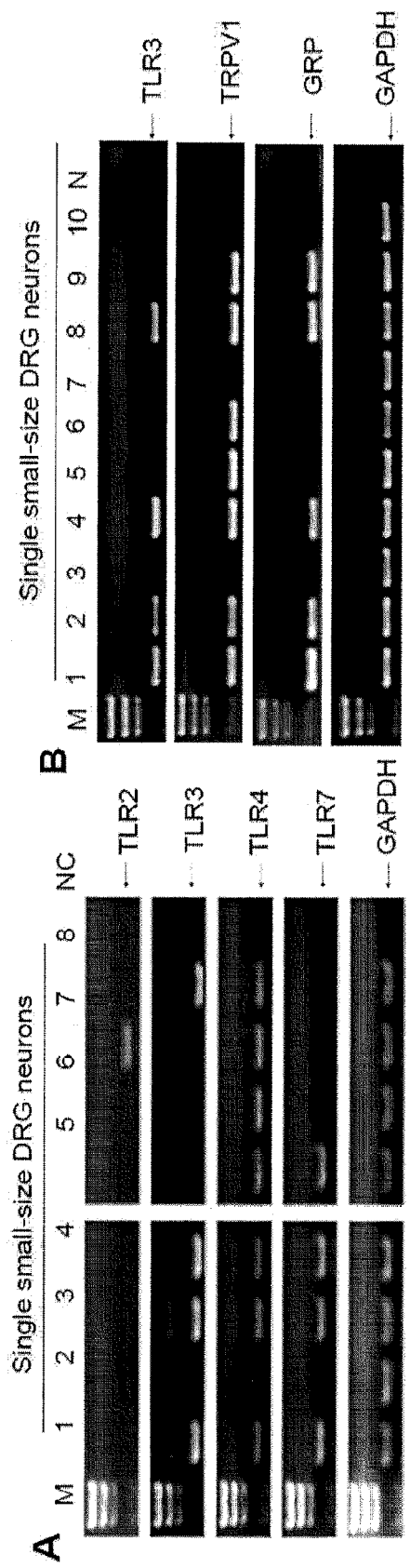
FIGS. 4A-4E are a series of graphs and photomicrographs showing expression of TLR3 in a subset of DRG neurons.
Figures 4C, 4D, 4E:
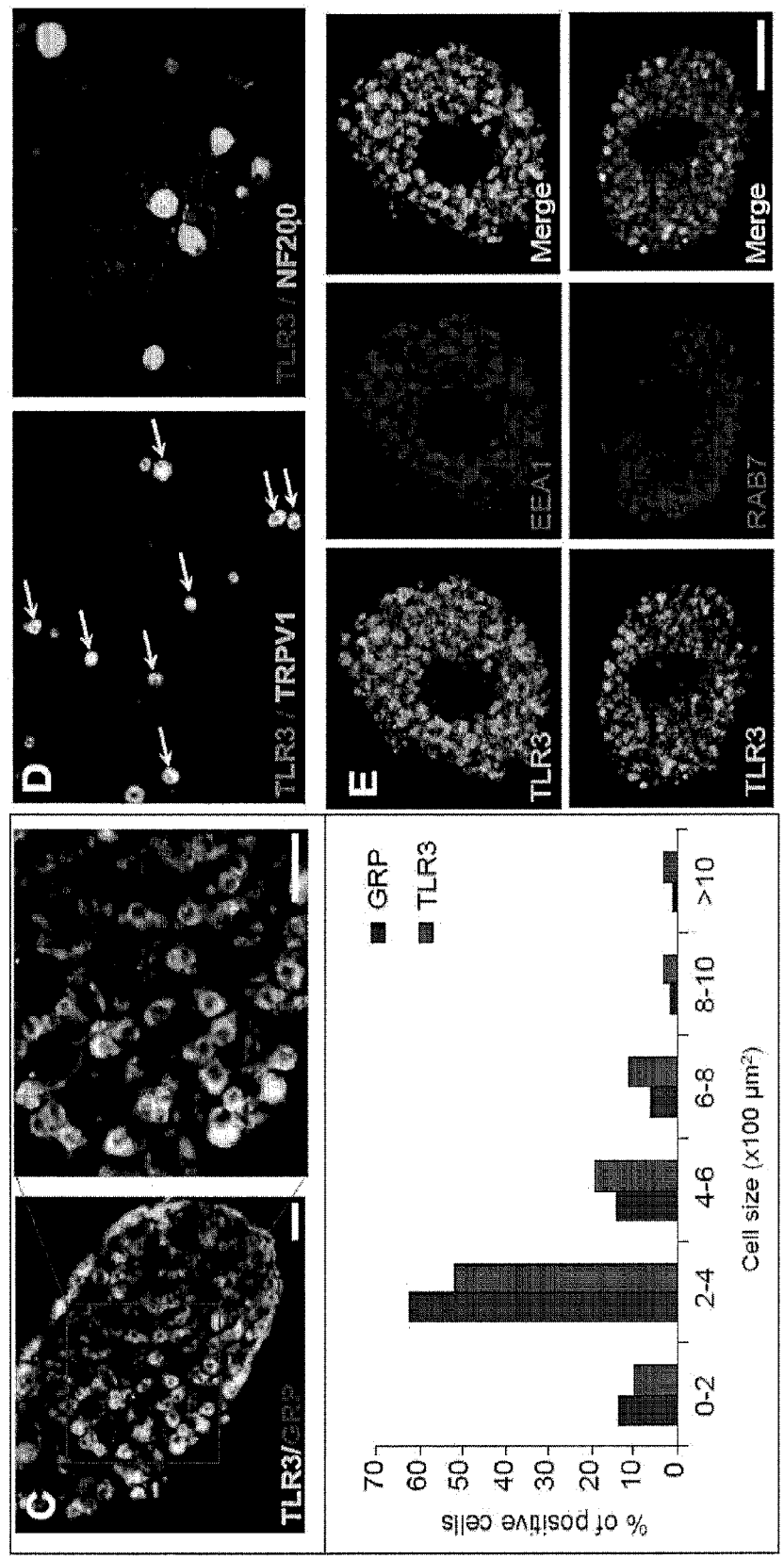

TLR3 was shown to be expressed by most embryonic DRG neurons during development (46). We characterized TLR3 expression in adult DRGs of mice using different methods. RT-PCR analysis revealed that TLR3 mRNA was expressed in adult DRGs, spinal cord, brain and spleen. In situ hybridization showed that TLR3 mRNA was expressed by ~25% DRG neurons, mainly in small-sized and some medium-sized neurons. We also preformed single cell RT-PCR analysis selectively in small-sized neurons to further characterize TLR3 expression in DRG neurons. We observed that TLR2, TLR3, TLR4 and TLR7 were expressed by distinct but overlapping populations of small DRG neurons (FIG. 4A). Approximately, 40%, 50%, and 70% small neurons expressed TLR3, GRP, and TRPV1, respectively (FIG. 4A). Notably, all TLR3+ neurons expressed TRPV1 and GRP, while all GRP+ neurons expressed TRPV1 (FIG. 4B). Immunohistochemistry in DRG tissues further confirmed that TLR3 was highly co-localized with GRP, and 77% (230/298) of TLR3+ neurons expressed GRP (FIG. 4C). Consistently, immunocytochemistry in dissociated DRG neurons showed that all TLR3+ neurons co-expressed TRPV1, but not NF200 (FIG. 4D). Finally, confocal microscopy revealed that TLR3 is co-localized with EEA1 (early endosome marker) and partially overlapped with Rab7 (late endosome marker) (FIG. 4E), indicating that TLR3 is located in intracellular endosomal compartments in DRG neurons, as in immune cells (23). Taken together, the unique localization of TLR3 in TRPV1- and GRP-expressing neurons has provided a cellular basis for the involvement of TLR3 in itch sensation.

Example 4

Figures 5A, 5B, 5C:
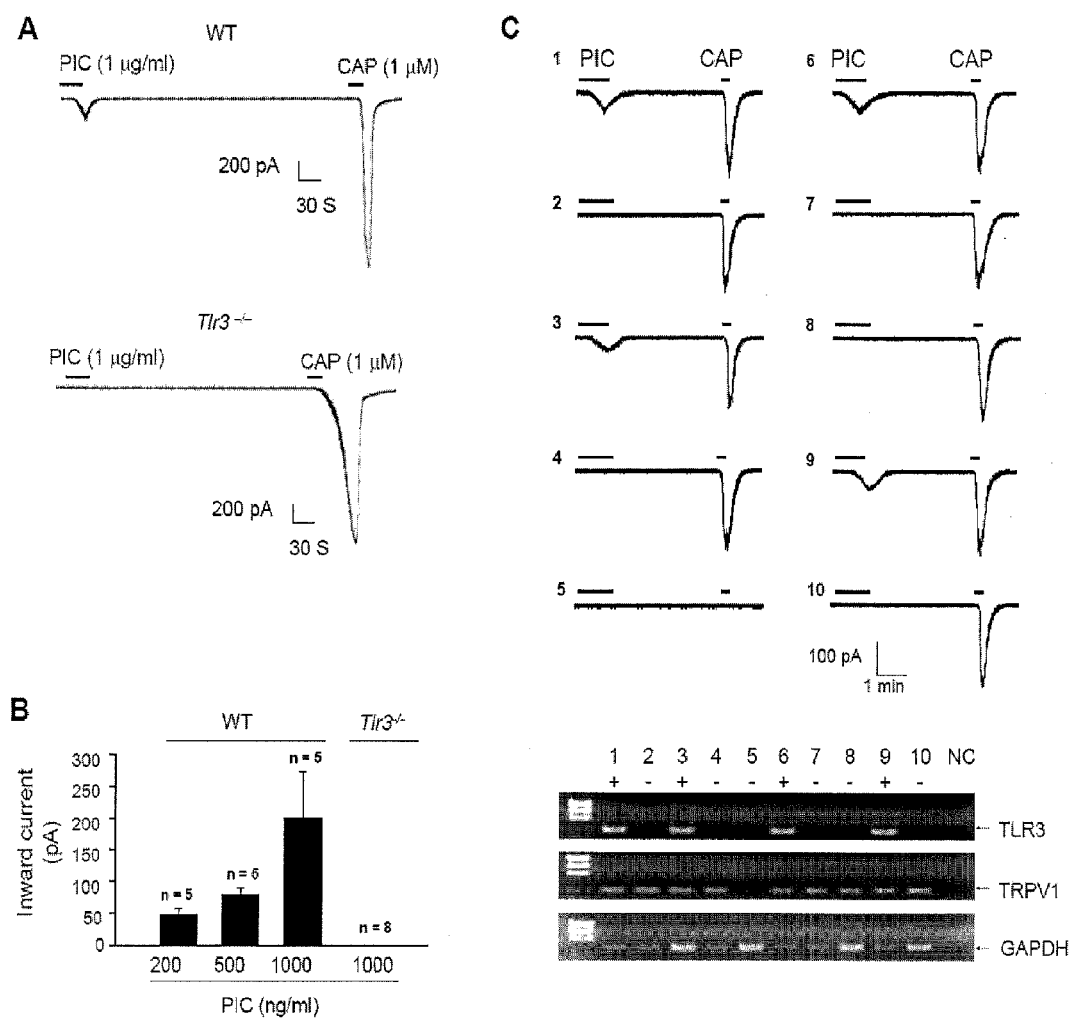
FIGS. 5A-5E are a series of graphs and photomicrographs showing that PIC induces inward current in dissociated DRG neurons and increases sEPSCs in lamina II neurons of spinal cord slices, in a TLR3-dependent manner.

TLR3 Agonist PIC Induces Inward Currents in DRG Neurons and Increases sEPSC in Spinal Cord Neurons: Evidence of Functional TLR3 in Soma and Central Terminals of DRG Neurons To further identify whether TLR3 expressed by DRG neurons is functional, we examined the responses of dissociated DRG neurons to a synthetic TLR3 agonist, polyribo-inosinic/cytidylic acid (PIC) in vitro. PIC elicited an inward current in 60% (5 out of 8) neurons in a dose-dependent manner (100-1000 ng/ml, FIG. 5A; B). Importantly, single cell RT-PCR analysis validated that all PIC-responsive neurons also expressed TLR3 (FIG. 5C). Conversely, PIC failed to induce inward currents DRG neurons from Tlr3$^{-/-}$ mice (FIGS. 5A; B), confirming a TLR3-dependent action. Of note capsaicin induced inward currents in all neurons that responded to PIC (FIG. 5A), in support of the immunocytochemical data (FIG. 4D).

Figures 5D, 5E:
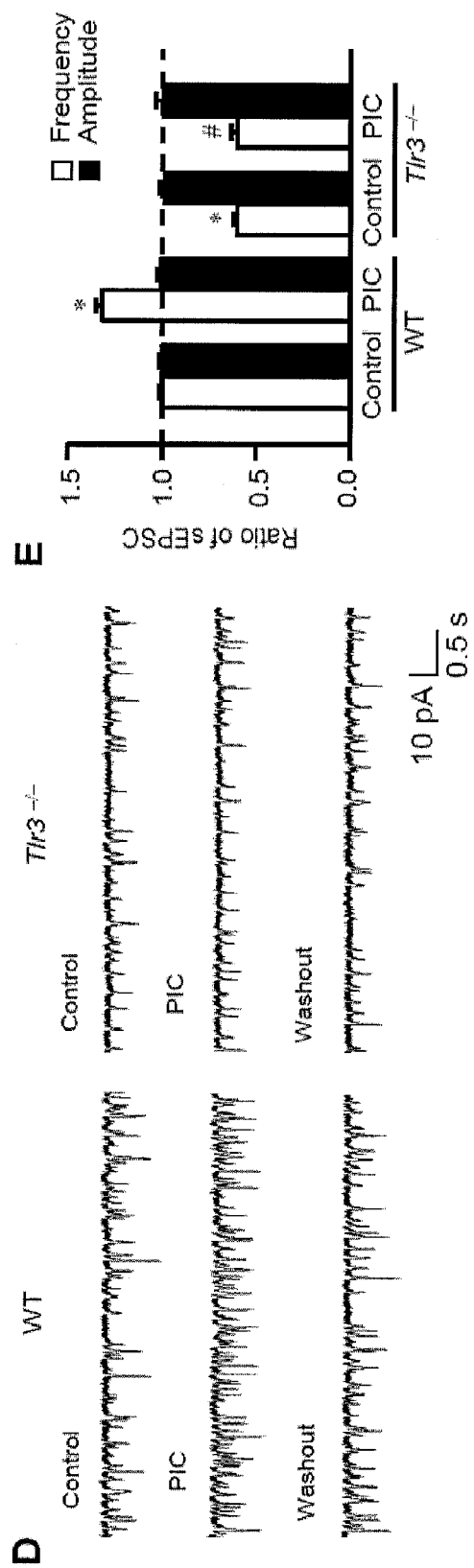

As DRG neurons project centrally to the spinal cord, we asked whether TLR3 can be transported from DRG cell bodies to their central terminals in the spinal cord. Double staining demonstrated that TLR3 is expressed both in TRPV1-positive dorsal root axons and substance P-positive primary afferent terminals in the dorsal horn. Next, we asked whether TLR3 in the central terminals is functional. We used patch clamp recording in lamina II neurons of spinal cord slices to investigate whether PIC would modulate glutamatergic neurotransmission. Perfusion of spinal cord slices with PIC increased the frequency but not the amplitude of spontaneous excitatory postsynaptic currents (sEPSC) in slices of WT but not Tlr3$^{-/-}$ mice (P<0.05, student's t test) (FIGS. 5D; E). Since the increase of sEPSC frequency is a result of enhanced glutamate release from presynaptic terminals (47), our results suggest that TLR3 modulates spinal basal glutamatergic neurotransmission via presynaptic mechanisms.

In addition, TLR3 was observed in TRPV1-expresing axons of the sciatic nerve and nerve terminals in the paw skin of mice, indicating that TLR3 is also transported to peripheral axons of DRG neurons.

Example 5

Lack of Tlr3 does not Affect Overall Development of DRG Neurons and Spinal Cord Circuits We asked whether itch deficiency in Tlr3$^{-/-}$ mice is a result of abnormal development of the DRG and spinal cord. We analyzed the size-distribution profile of DRG neurons using the pan-neuronal marker SCG-10 and found no evidence of neuronal loss or size changes of DRG neurons. Immunohistochemistry in DRG sections of Tlr3$^{-/-}$ mice also exhibited normal expression patterns of the neurochemical markers TRPV1, CGRP, P2X3 and NF-200. Therefore, TLR3 is not involved in survival and cell fate determination of DRG neurons. The expression of the neuronal markers NeuN and PKCγ, as well as the innervations of primary afferents (CGRP/IB4) in the spinal dorsal horn were also indistinguishable between WT and Tlr3$^{-/-}$ mice. Moreover, we examined nerve innervations in hairy or non-hairy skin in Tlr3$^{-/-}$ mice. We found that the staining of PGP9.5, a pan-neuronal marker, in both hairy and non-hairy skin was comparable in WT and Tlr3$^{-/-}$ mice. Real-time RT-PCR analysis revealed that the expression of TLR2, TLR4 and TLR7 mRNAs in DRG and skin were largely unaltered in Tlr3$^{-/-}$ mice, despite a moderate increase in TLR4 expression in skin. Thus, it is unlikely that the itch deficiency we observed in Tlr3$^{-/-}$ mice results from developmental defects of DRG and spinal cord.

Example 6

Algesic or Pruritic Agents Induce Normal Responsiveness in DRG Neurons of Tlr3$^{-/-}$ Mice We used calcium imaging to investigate the responsiveness of DRG neurons to algesic and pruritic agents, such as capsaicin, histamine and chloroquine. $Ca^{2+}$ imaging showed that capsaicin, histamine, and chloroquine induced intracellular $Ca^{2+}$ increases in 39%, 10%, and 5% neurons, respectively, in wild-type mice, in agreement with a previous observation (11). Of note, these response percentages did not alter in Tlr3$^{-/-}$ mice. Consistently, the amplitude of capsaicin-induced currents and the percentage of TRPV1-expressing DRG neurons were comparable between WT and Tlr3$^{-/-}$ mice (FIG. 5A). Thus, these data suggest that TLR3 deficiency does not alter responsiveness of DRG neurons to algesic or pruritic agents in mice.

Example 7

Figures 6A, 6B, 6C, 6D:
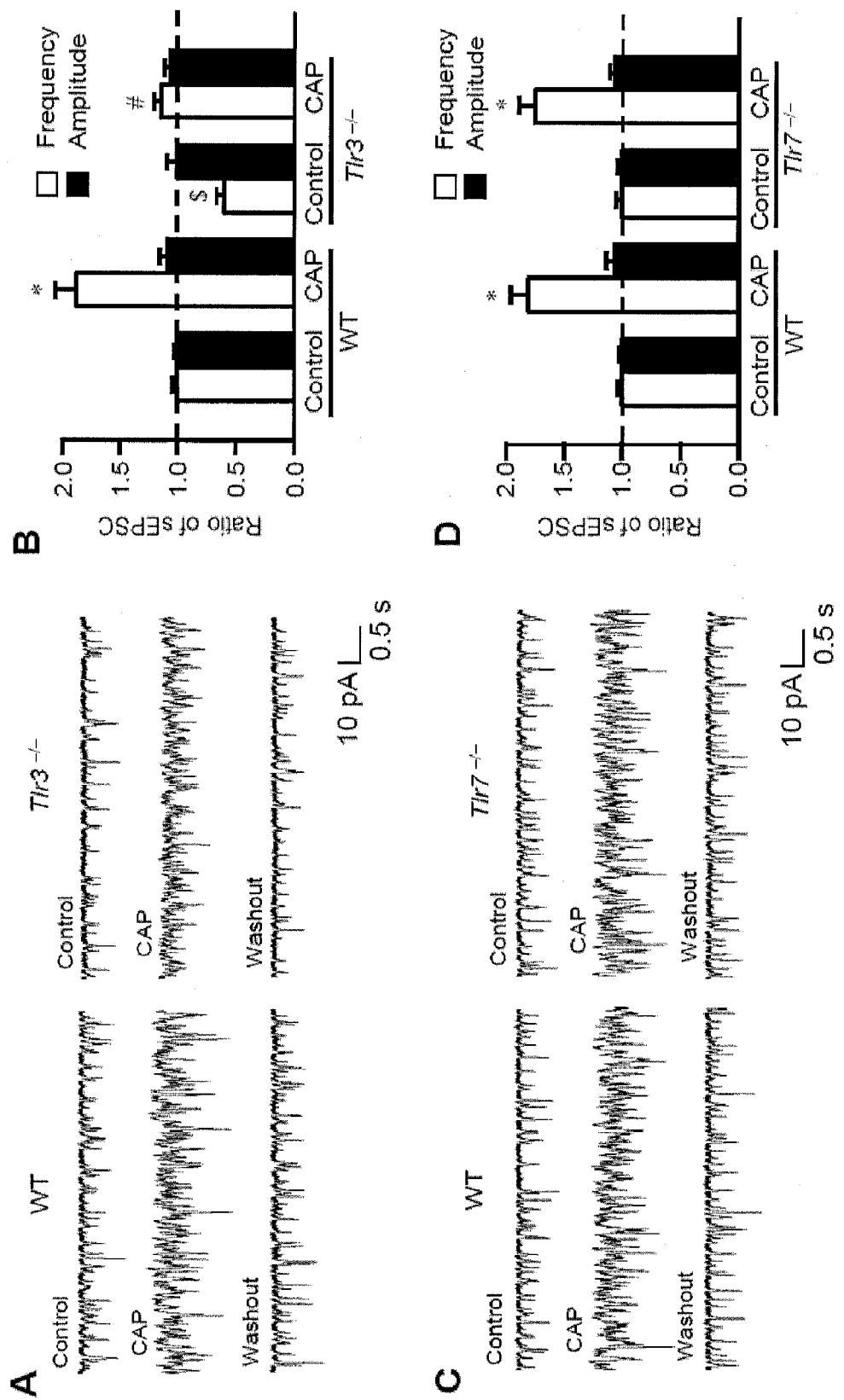
FIGS. 6A-6F are a series of graphs and photomicrographs showing impaired synaptic transmission and LTP induction in the spinal cord dorsal horn of Tlr3$^{-/-}$ mice but not Tkr$^{-/-}$ mice.

TRPV1-Evoked Enhancement of Synaptic Transmission and LTP Induction in the Spinal Cord are Impaired in Tlr3$^{-/-}$ Mice Since central terminals of TRPV1-expressing nociceptors are indispensible for all forms of itch (15), we examined possible deficits in the central branches of DRG neurons due to the loss of TLR3. Capsaicin application to spinal cord slices induced a dramatic increase of sEPSC frequency in lamina II neurons of WT mice, and this increase was abrogated in Tlr3$^{-/-}$ mice (FIGS. 6A,B), but fully remained in Tlr7$^{-/-}$ mice (FIGS. 6C,D). In parallel, the intensity of TRPV1-expressing axons/terminals in the superficial dorsal horn was also significantly reduced in Tlr3$^{-/-}$ mice (P<0.05, Student's t-test). Moreover, intrathecal injection of capsaicin induced biting, licking and scratching behavior on the body of WT mice, and these responses were substantially reduced in Tlr3$^{-/-}$ mice (P<0.05, Student's t-test). Collectively, these data point to a specific deficit of TRPV1 signaling in the spinal central terminals but not in the cell bodies and peripheral terminals of DRG neurons in Tlr3$^{-/-}$ mice.

Figures 6E, 6F:
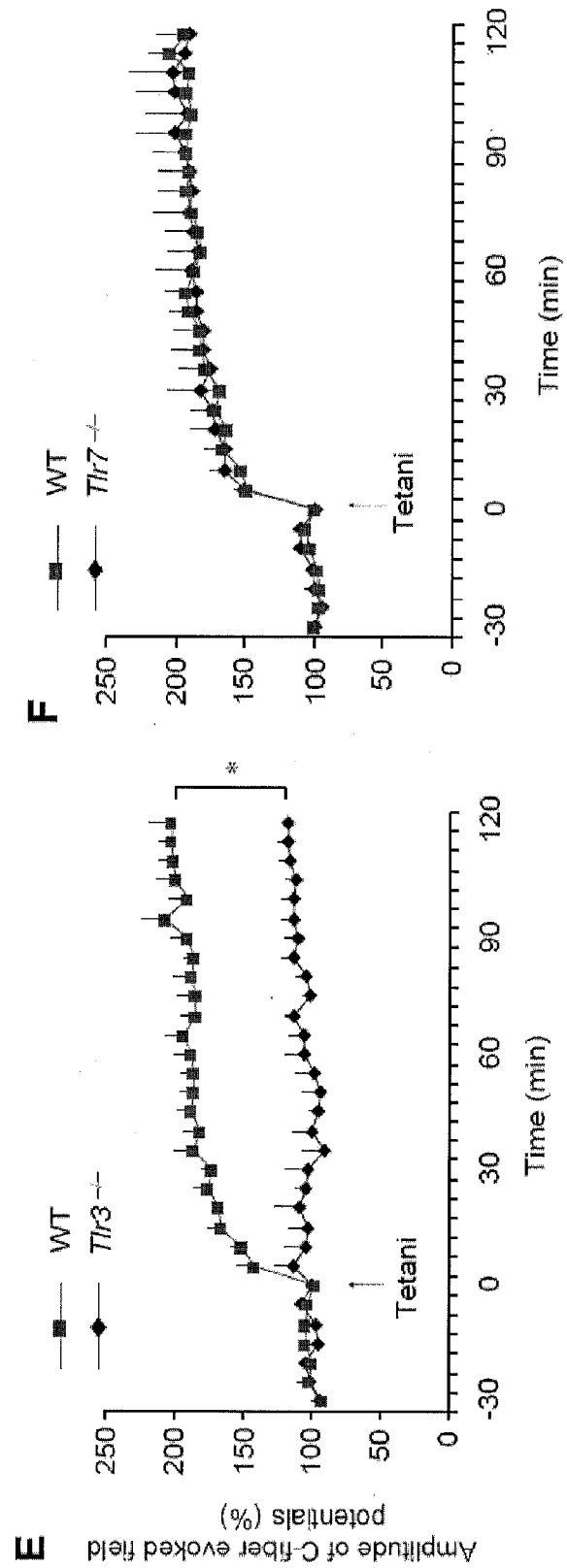

Long-term potentiation (LTP) is a unique form of synaptic plasticity (37) and central sensitization (35) in the spinal cord. Tetanic stimulation of the C-fibers of the sciatic nerve elicited LTP of the field potential in WT mice (FIG. 6E). Strikingly, spinal LTP was not induced in Tlr3$^{-/-}$ mice (P<0.05, Two-way ANOVA, repeated measures) (FIG. 6E). In contrast, spinal cord LTP was fully induced and maintained in Tlr7$^{-/-}$ mice (FIG. 6F). These results further support an essential role of TLR3, but not TLR7, in the genesis of activity-dependent central sensitization.

Given a critical role of spinal GRP/GRPR signaling in pruritus (9; 10), we also compared the spinal GRP expression in WT and Tlr3$^{-/-}$ mice. As previously reported (9), GRP is expressed in primary afferent axons and terminals in the superficial dorsal horn of WT mice, but this expression was reduced in Tlr3$^{-/-}$ mice (P<0.05, student's t-test). Of interest exogenous GRP$_{18-27}$ via intrathecal route was able to rescue the itch deficits in Tlr3$^{-/-}$ mice and elicited comparable scratching in Tlr3$^{-/-}$ and WT mice, indicating the ascending itch pathway from the secondary order spinal neurons to the brain is still intact in Tlr3$^{-/-}$ mice. Together, these results suggest that itch deficiency in Tlr3$^{-/-}$ mice may be attributed to an impairment in TRPV1 and GRP-mediated neurotransmission in the spinal cord.

Example 8

TLR3 in DRG is Required for the Full Expression of Itch in Adult WT Mice

Figures 7A, 7B, 7C, 7D:
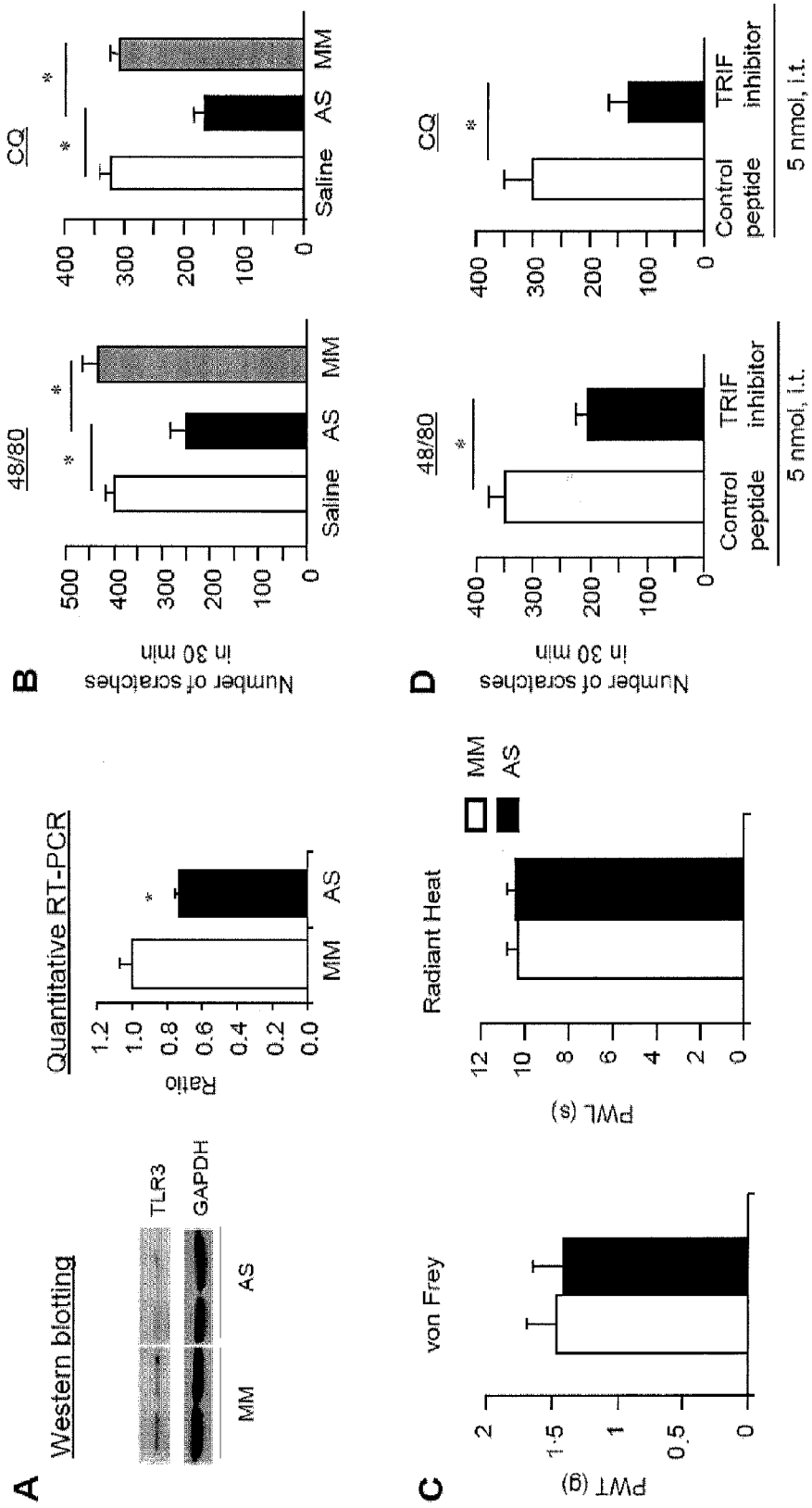
FIGS. 7A-7D are a series of graphs and photomicrographs showing that TLR3 signaling in DRGs of WT adult mice is required for pruritus.

To define the specific role of TLR3 in DRGs for itch sensation in adult mice, we used antisense oligodeoxynucleotides (ODNs) to knock down TLR3 expression in DRGs of adult WT mice. Intrathecal injections of TLR3 antisense ODNs (AS-ODNs, daily for 5 days) led to a partial knockdown of TLR3 protein and mRNA levels in DRGs (P<0.05, Student's t test) (FIG. 7A). As comparison, intrathecal AS-ODNs did not affect TLR4 expression in the DRG, confirming the specificity of the AS knockdown. Notably, TLR3-targeted AS-ODNs significantly inhibited compound 48/80 and chloroquine-induced scratching in adult mice (P<0.05, Student's t test) (FIG. 7B), without effects on mechanical and thermal sensitivity (FIG. 7C). Since TLR3 signals exclusively through the adaptor protein TRIF (23), we also tested the effects of a membrane permeable peptide inhibitor of TRIF (48). Intrathecal injection of the TRIF inhibitor in adult mice suppressed the scratches induced by both compound 48/80 and chloroquine (FIG. 7D). These results suggest that TLR3 signaling in DRG is also important for the full expression of histamine-dependent and independent itch in adult WT mice that do not have genetic complications of KO mice.

Example 9

TLR3 Plays an Essential Role in Dry Skin-Induced Chronic Pruritus

Pruritus is often associated with skin diseases (7), such as atopic dermatitis and psoriasis. We also examined the possible roles of TLR3 in a clinically relevant condition of dermatitis-elicited itch. First, we examined possible changes in the skin of Tlr3$^{-/-}$ mice. Histological evaluation did not reveal obvious changes in the thickness of epidermis and dermis, and the number of hair follicles remained unchanged. Given a crucial role of skin mast cells in pruritus, we also checked the number and functions of mast cells in Tlr3$^{-/-}$ mice. We found that the number of mast cells in hairy skin was unchanged in Tlr3$^{-/-}$ mice (P>0.05). ELISA analysis revealed that histamine level was similar in the skins of WT and Tlr3$^{-/-}$ mice (P>0.05). Moreover, histamine release in skin organ cultures, induced by compound 48/80, a mast cell degranulation stimulator, was comparable in WT and Tlr3$^{-/-}$ mice, indicating that loss of TLR3 did not affect the ability of mast cells to produce and release histamine. The expression of other mast cell markers, such as tryptase, chymases, c-Kit (CD117), and well nerve growth factor (NGF) was also unaltered in skins of Tlr3$^{-/-}$ mice (P>0.05). Together, the gross morphology and biochemical markers seem to be normal in Tlr3$^{-/-}$ mice.

Figures 8A, 8B, 8C, 8D, 8E, 8F:
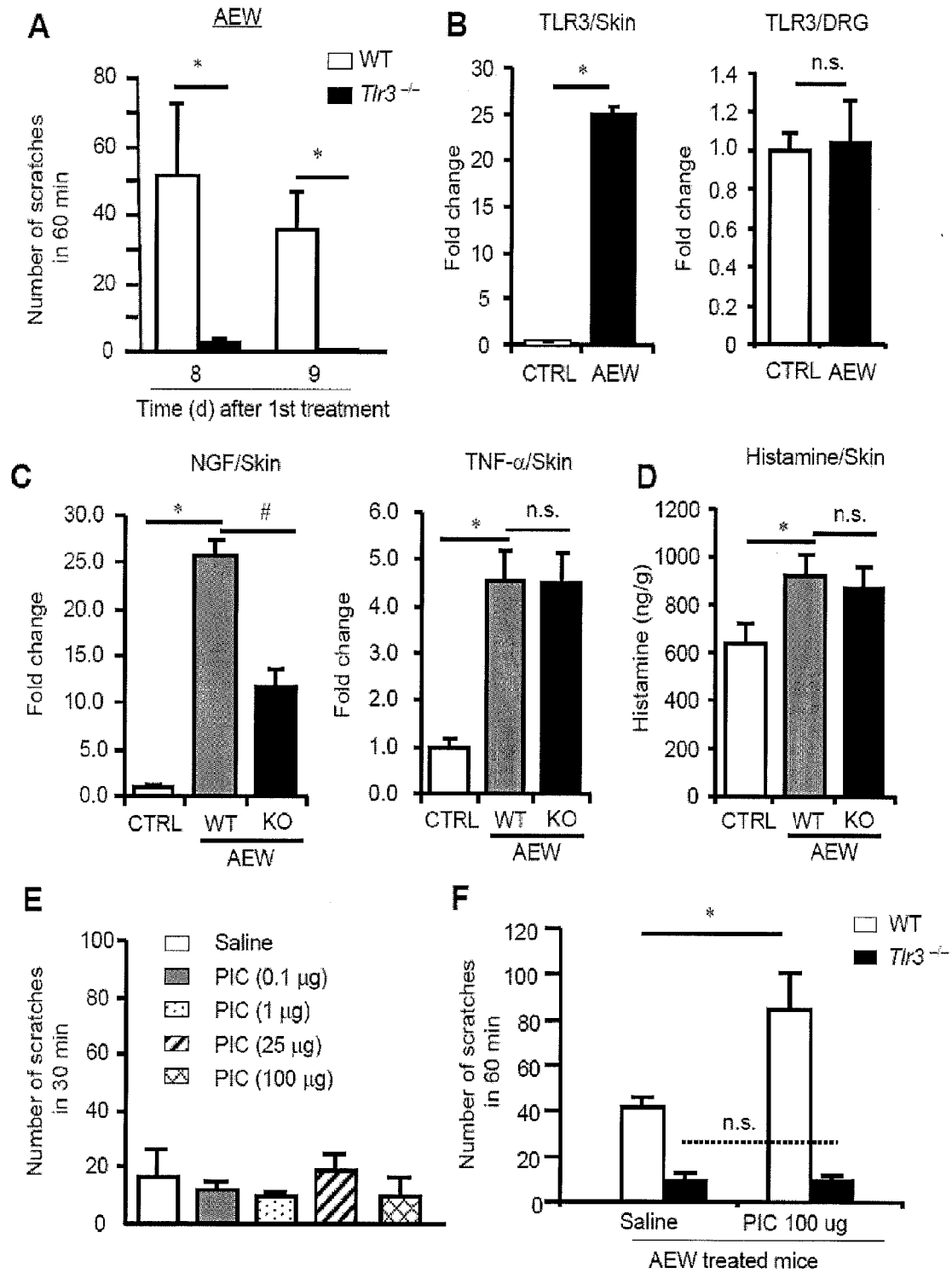
FIGS. 8A-8F are a series of eight bar graphs showing that TLR3 is involved in chronic spontaneous pruritus after dry skin-induced dermatitis.

To determine the role of TLR3 in pathological chronic itch, we painted skin with acetone and diethyether following by water (AEW) for 7 days to induce a dry skin condition in mice (49; 50). Seven days after AEW treatment, WT mice showed robust spontaneous scratching on day 8 and 9, but this spontaneous itch was eliminated in Tlr3$^{-/-}$ mice (P<0.05, Student's t test) (FIG. 8A). Notably, AEW treatment also elicited a dramatic increase of TLR3 expression in skin (P<0.05, Student's t test) but not in DRG (FIG. 8B). Further, AEW induced NGF up-regulation in WT mice, which was partially reduced in Tlr3$^{-/-}$ mice (P<0.05, Student's t test) (FIG. 8C). However, AEW-induced comparable up-regulation of TNF-α and histamine in WT and Tlr3$^{-/-}$ mice (FIGS. 8C; D).

Finally, we tested whether PIC is sufficient to induce itch. Intradermal injections of the TLR3 agonist PIC at various doses (0.1-100 μg) failed to induce obvious scratching responses in naïve mice (FIG. 8E). However, PIC was able to potentiate spontaneous scratching after AEW treatment, in a TLR3-dependent manner (P<0.05, student's t-test) (FIG. 8F).

Thus, upon the up-regulation of TLR3 in dry skin conditions, even exogenous TLR3 agonist could be pruritic.

Example 10

Toll-Like Receptor-7 Mediates Pruritus

TLRs play a critical role in triggering innate immune responses to pathogen-associated molecular patterns (PAMPs) in mammals. Except for TLR3, TLRs engage downstream signaling cascades via MyD88 to produce cytokines and chemokines and fight against pathogenic infection (Takeuchi, O. & Akira, S. Cell 140, 805-820 (2010)). Mammalian TLR family comprises at least 13 members (TLR1 to TLR13). TLR7 recognizes single-stranded RNAs from RNA viruses (Takeuchi, O. & Akira, S. Cell 140, 805-820 (2010)) (Marchand, F., Perretti, M., & McMahon, S. B. Nat. Rev. Neurosci 6, 521-532 (2005)). As innate immunity is strongly implicated in abnormal pain hypersensitivity (Marchand, F., Perretti, M., & McMahon, S. B. Nat. Rev. Neurosci 6, 521-532 (2005)), we first examined whether thermal and mechanical pain sensitivity or pathological pain is altered in Tlr7 knockout (Tlr7$^{-/-}$) mice.

Compared to wild type (WT) mice, Tlr7$^{-/-}$ mice exhibited normal thermal pain sensitivity, assessed by Hargreave's test and tail-flick test, and normal mechanical pain sensitivity, assessed by graded von Frey filaments and Randall-Selitto test. Acute inflammatory pain elicited by intraplantar injection of capsaicin, mustard oil, or formalin in both the first and second phases (FIG. 11a), as well as carrageenan-induced persistent inflammatory pain (FIG. 11b) and spinal nerve ligation-induced neuropathic pain was unaltered in Tlr7$^{-/-}$ mice. Consistently, Tlr7$^{-/-}$ mice did not show any developmental defects in the dorsal root ganglia (DRG) and spinal cord and the expression of neurochemical markers such as TRPV1, CGRP, and IB4 was normal.

Figures 11A, 11B, 11C:
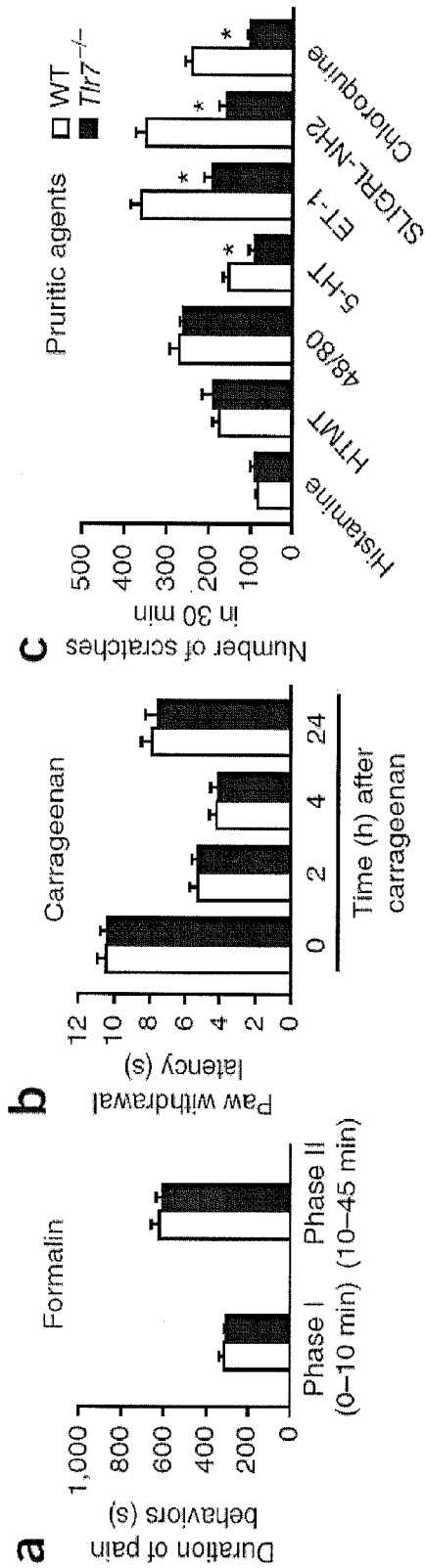
FIGS. 11A-11C are a series of three bar graphs showing that intact pain but impaired itch in Tlr7$^{-/-}$ mice.
Figures 12A, 12B, 12C:
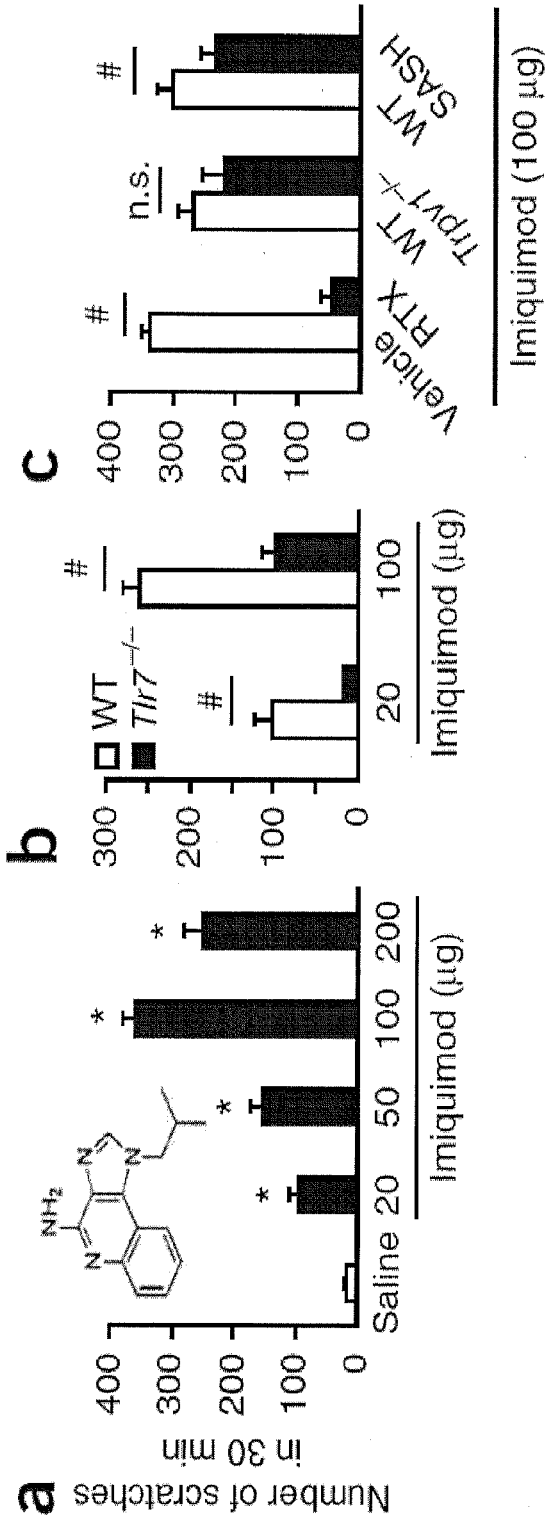
FIGS. 12A-12C are a series of three bar graphs showing number of scratches induced by imiquimod.
Figures 14A, 14B, 14C, 14D, 14E:
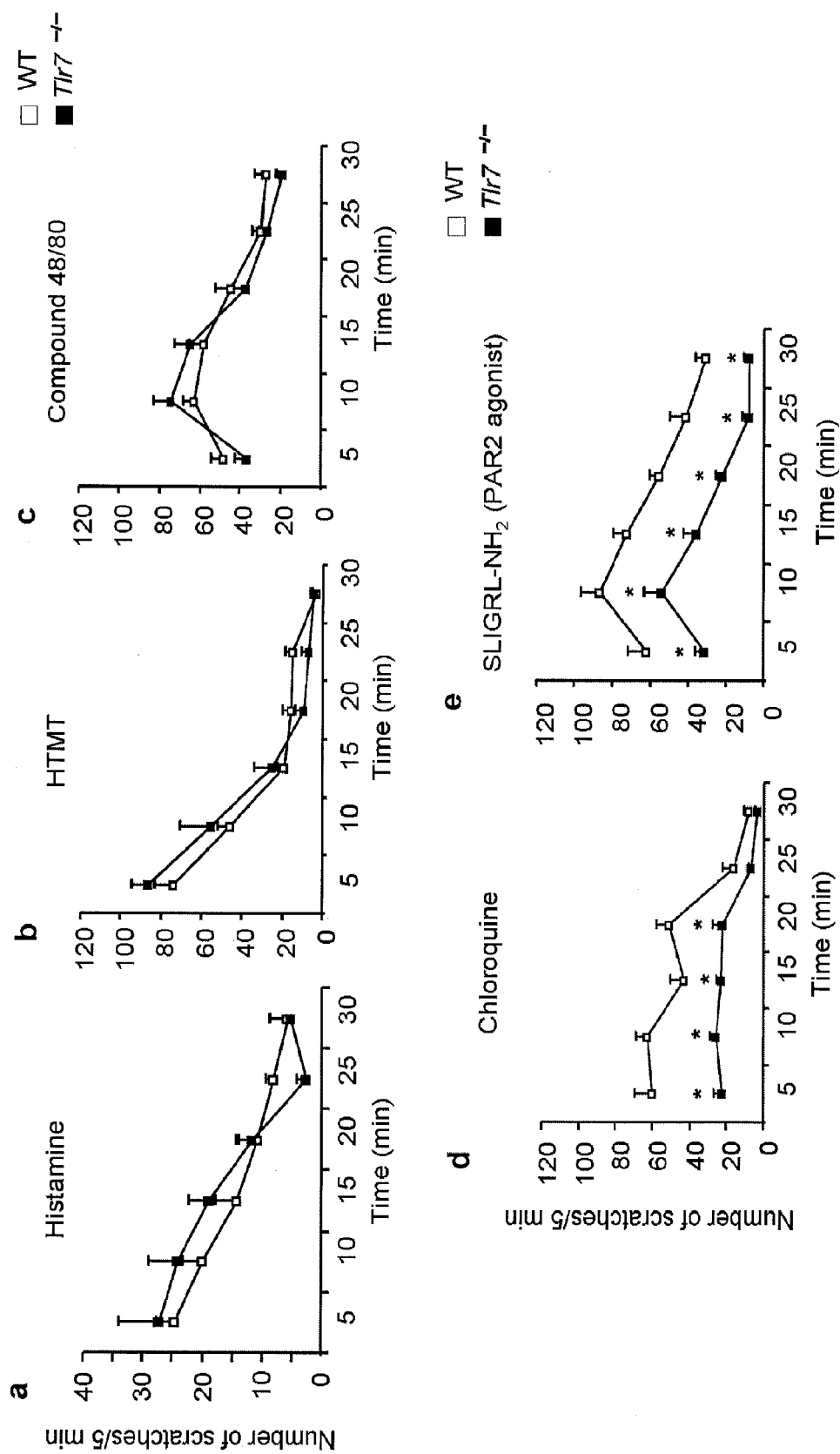
FIGS. 14A-14J is a panel of 10 bar graphs showing time course of scratching responses for a period of 30 minutes in Tlr7$^{-/-}$ and WT mice, following intradermal injection of 50 μl of pruritic agents including histamine (FIG. 14A, 500 μg), HTMT (FIG. 14B, H1 agonist, 100 μg), compound 48/80 (FIG. 14C, 100 μg), chloroquine (FIG. 14D, 200 μg), SLIGRL-NH2 (FIG. 14E, PAR2 agonist); serotonin (FIG. 14F, 5-HT; 20 μg), endothelin-1 (FIG. 14G, ET-1, 25 ng), imiquimod (FIG. 14H, 100 μg), R848 (FIG. 14I, 100 μg), and loxoribine (FIG. 14J, 100 μg). *P<0.05, versus WT control, n=5-8 mice. All data are means±s.e.m.
Figures 14F, 14G, 14H, 14I, 14J:
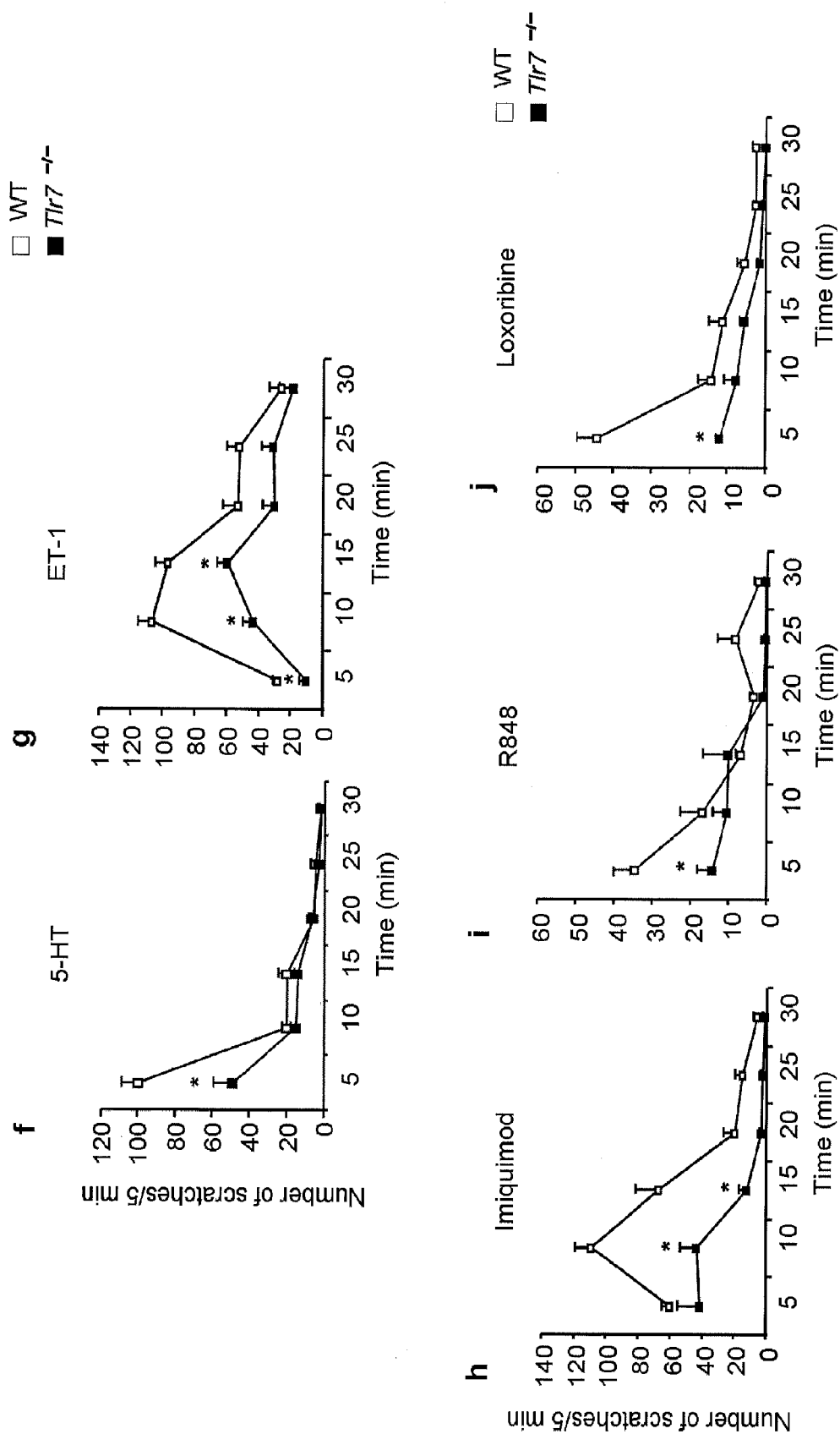

Recent studies have revealed distinct molecular mechanisms underlying pain and itch (Sun, Y. G. & Chen, Z. F. Nature 448, 700-703 (2007); Sun, Y. G. et al. Science 325, 1531-1534 (2009); Liu, Q. et al. Cell 139, 1353-1365 (2009)). We next evaluated whether TLR7 plays a role in itch sensation. We counted the number of scratches (bouts) by a hindpaw of mouse following intradermal injection of pruritogenic agents in the nape of the neck. Notably, scratches induced by histamine-dependent pruritogens, such as histamine, HTMT (histamine H1 receptor agonist), and compound 48/80 which is known to release histamine from mast cells, were comparable in Tlr7$^{-/-}$ and WT mice (FIG. 11c and FIGS. 14a-c). Strikingly, Tlr7$^{-/-}$ mice showed a marked reduction in scratching behaviors in response to nonhistaminergic pruritogens, including chloroquine (CQ), an antimalaria drug (Liu, Q. et al. Cell 139, 1353-1365 (2009)), and SLIGRL-NH2, an agonist of protease-activated receptor 2 (PAR2, FIG. 11c and FIGS. 14d,e). CQ-induced scratching in both sexes was reduced in Tlr7$^{-/-}$ mice. Notably, CQ induced a bell-shaped dose response curve, but scratching elicited by the highest dose (600 μg) was TLR7-independent. Further, scratches induced by serotonin (5-HT) and endothelin-1 (ET-1) were also impaired in Tlr7$^{-/-}$ mice (FIG. 11c and FIGS. 14f,g). TLR7 was originally identified to recognize imidazoquinoline derivatives such as imiquimod and resiquimod (R848) and guanine analogues such as loxoribine, and all have anti-viral and anti-tumor properties (Takeuchi, O. & Akira, S. Cell 140, 805-820 (2010); Hemmi, H. et al. Nat. Immunol. 3, 196-200 (2002); Lee, J. et al. Proc. Natl. Acad. Sci. U.S.A 100, 6646-6651 (2003)). Intradermal injection of imiquimod, R848, and loxoribine induced inverted-U-shaped dose response curve of scratching in mice (FIG. 12a). As expected, scratches induced by imiquimod, R848, and loxoribine were reduced in Tlr7$^{-/-}$ mice (FIG. 12b and FIGS. 14h-j).

Figures 15A, 15B, 15C:
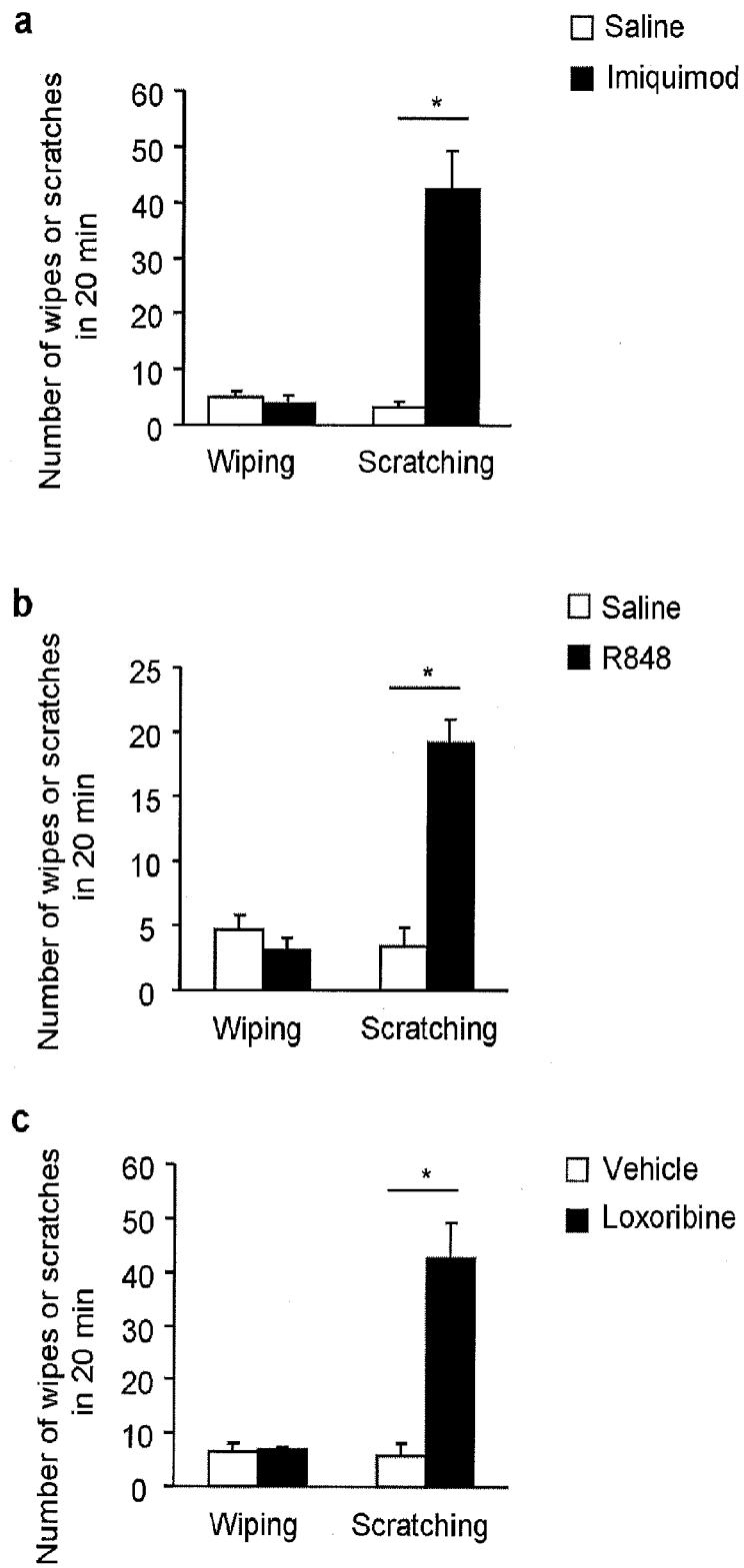
FIGS. 15A-15C is a series of three bar graphs showing a distinct role of TLR7 for mediating pain and itch in the "cheek model." Intradermal injection of TLR7 ligands imiquimod (20 μg, FIG. 15A), R848 (20 μg, FIG. 15B), and loxoribine (20 μg, FIG. 15C) into the cheek induces itch-like scratching by the hind limb but not pain-indicative wiping by forelimbs. P<0.05, n=5-8 mice.

To further investigate a unique role of TLR7 in itch versus pain, we used a recently developed "cheek model" of itch (Shimada, S. G. & LaMotte, R. H. Pain 139, 681-687 (2008)). The TLR7 ligands imiquimod, R848, and loxoribine all elicited itch-like scratching but not pain-indicative wiping behavior (FIG. 15), supporting a specific role of TLR7 in mediating itch rather than pain.

C-fibers, express transient receptor potential subtype V1 (TRPV1) and are indispensable for itch sensation by various pruritogens (Imamachi, N. et al. Proc. Natl. Acad. Sci. U.S.A 106, 11330-11335 (2009)). Pretreatment with resiniferatoxin (RTX), an ultra potent TRPV1 agonist, resulted in a loss of heat sensitivity and almost abolished imiquimod-induced scratches (FIG. 12c). Despite a marked reduction of histamine-induced scratching in Trpv1$^{-/-}$ mice (Shim, W. S. et al. J. Neurosci. 27, 2331-2337 (2007)), imiquimod-induced scratching remained unaltered in Trpv1$^{-/-}$ mice (FIG. 12c). Thus, TRPV1-expressing C-fibers but not TRPV1 per se are required for imiquimod-elicited itch. We also tested itch responses in mast cell-deficient SASH mice (Liu, Q. et al. Cell 139, 1353-1365 (2009)) and only found a moderate reduction (28%) in imiquimod-induced scratching (FIG. 12c).

Figures 13A, 13B, 13C, 13D, 13E, 13F:
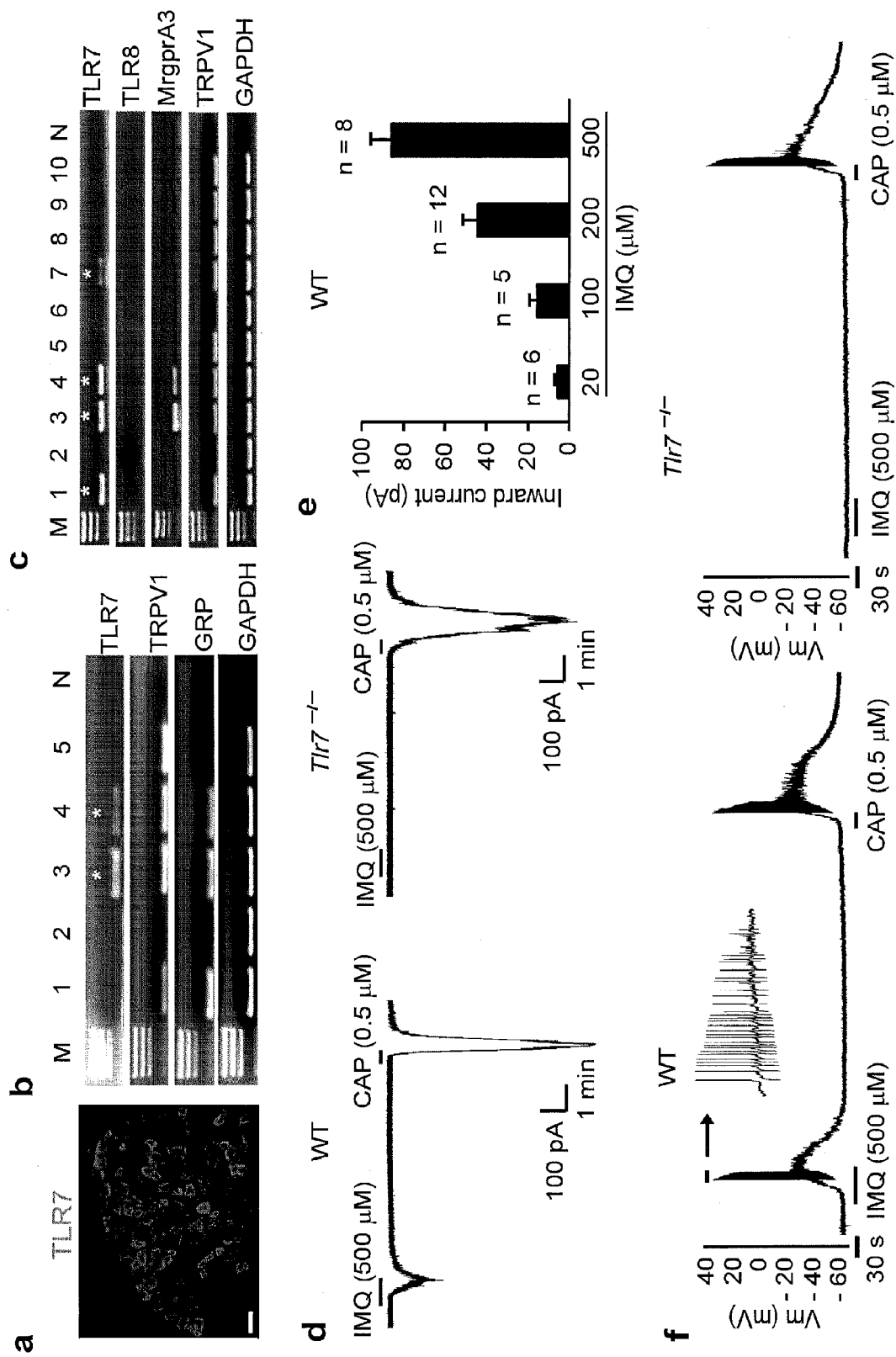
FIGS. 13A-13F are a series of graphs and photomicrographs showing expression of functional TLR7 in DRG neurons.

It is virtually unknown whether primary sensory neurons express functional TLR7. Immunohistochemistry revealed that TLR7 was mainly expressed in small-size dorsal DRG neurons (FIG. 13a). TLR7 is highly co-localized with TRPV1 and gastrin-releasing peptide (GRP), a neuropeptide that is known to elicit itch via GRP receptor expressed by spinal cord superficial dorsal horn neurons (Sun, Y. G. & Chen, Z. F. Nature 448, 700-703 (2007)). Absence of TLR7 staining in DRG sections of Tlr7$^{-/-}$ mice confirmed the specificity of TLR7 antibody. In situ hybridization also showed TLR7 mRNA expression in DRG neurons. Single cell RT-PCR analysis, conducted selectively in small-size DRG neurons, indicated that TLR7+ population is within GRP+ population which is within TRPV1+ population (FIG. 13b). Interestingly, the G protein-coupled receptor (GPCR) MrgprA3, which is known to mediate CQ-induced itch[5], was co-localized with TLR7 (FIG. 13c). In contrast, TLR8, the TLR family member that is phylogenetically most similar to TLR7, was not expressed in adult mouse DRG (FIG. 13c).

Patch clamp recording showed that imiquimod (20-500 μM) induced dose-dependent inward currents in capsaicin-responsive DRG neurons of WT but not Tlr7$^{-/-}$ mice (FIGS. 13d,e). Imiquimod also induced action potentials in DRG neurons of WT but not Tlr7$^{-/-}$ mice (FIG. 13f). Thus, imiquimod could directly excite DRG neurons in a TLR7-dependent manner. R848, a dual ligand for TLR7 and TLR8, was also able to induce TLR7-dependent inward currents.

Immunohistochemistry revealed TLR7 expression in nerve branches in the dermis and nerve terminals in the epidermis of skin tissues. RTX treatment ablated TLR7+ fibers in the skin. We also found TLR7 immunoreactivity in spinal cord axonal terminals. Thus, it is likely that TLR7 is transported from DRG cell bodies to skin nerve terminals to mediate pruritus.

In summary, we identified TLR7 as a novel mediator for itch sensation, which is quite different from previously identified GPCR receptors (Sun, Y. G. & Chen, Z. F. Nature 448, 700-703 (2007); Liu, Q. et al. Cell 139, 1353-1365 (2009); Shim, W.S. & Oh, U. Mol. Pain. 4, 29 (2008)). We found functional TLR7 receptors in small-size DRG neurons that co-express TRPV1, GRP, and MrgprA3. In particular, TLR7 is important for pruritus elicited primarily by nonhistaminergic pruritogens, although we do not exclude a partial role of TLR7 in histamine-dependent itch. Because TLR7 activation by imiquimod and R848 not only induced marked scratching but also generated inward currents and actions potentials in DRG neurons, TLR7 ligands are likely to elicit itch via a direct action on sensory neurons. However, we should not rule out a role of non-neuronal cells in the skin such as keratinocytes and mast cells in TLR7-mediated pruritus. Notably, topical application of imiquimod, a clinically used anti-viral and anti-tumor drug, frequently elicits pruritus in human (Madan, V., Lear, J. T., & Szeimies, R. M. Lancet 375, 673-685 (2010)) and also induces psoriasis-like skin inflammation in mice (van der Fits, L. et al. J. Immunol. 182, 5836-5845 (2009)), indicating a conservative role of TLR7 in pruritus across different species. Chronic itch is frequently associated with skin diseases and is often resistant to antihistamine treatment (Ikoma, A., Steinhoff, M., Stander, S., Yosipovitch, G., & Schmelz, M. Nat. Rev. Neurosci. 7, 535-547 (2006); Paus, R., Schmelz, M., Biro, T., & Steinhoff, M. J. Clin. Invest 116, 1174-1186 (2006)). Given a crucial role of TLR7 in pruritus, targeting TLR7 is promising for anti-itch treatment under skin disease conditions.

Example 11 siRNA Targeting TLR7 Reduces Scratching in Animal Model

4 μg siRNA targeting TLR7 (CCUUACACUAUUUC-CGAUA (SEQ ID NO:8)) (synthesized by Dharmacon, On-target Plus) or a non-targeting control siRNA (UAGCGAC-UAAACACAUCAAUU (SEQ ID NO:9)) was administered intrathecallly to wild type (CD1) mice at 24 and 48 hours before the mice received an injection of IMQ (20 mg). siRNA was dissolved in RNase-free water at 1 μg/μl as stock solution and mixed with polyethyleneimine (PEI, Fermentas Inc. Hanover, USA, 0.18 μl of PEI solution for 1 μg of siRNA), 10 minutes before injection, to increase cell membrane penetration and reduce the degradation. PEI was dissolved in 5% glucose. After behavioral testing, DRG tissues were collected for quantitative PCR analysis.

Figures 16A, 16B:
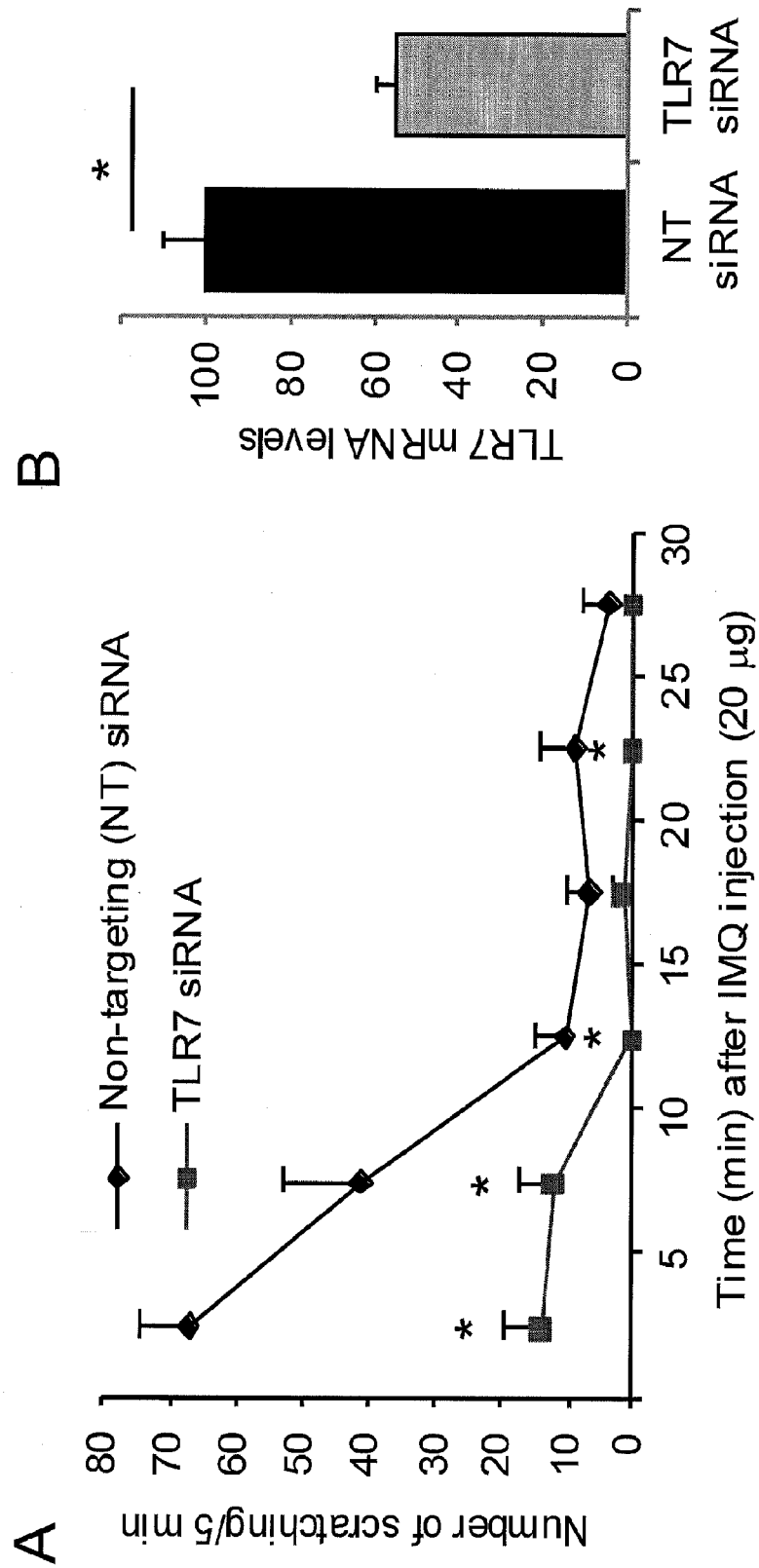
FIGS. 16A-16B are graphs showing that TLR7 siRNA reduces IMQ-induced itch.

As shown in FIG. 16A, mice receiving treatment with the TLR7 siRNA had significantly reduced IMQ induced scratches (*P<0.05, compared to NT siRNA, n=5).

Quantitative PCR demonstrated reduced levels of TLR7 mRNA levels in cervical DRGs, *P<0.05, n=5. See FIG. 16B.

These results demonstrate that siRNA targeting TLR7 can effectively reduce itching in an animal model of pruritus.

REFERENCES

1. Ikoma, A., Steinhoff, M., Stander, S., Yosipovitch, G., and Schmelz, M. 2006. The neurobiology of itch. *Nat. Rev. Neurosci.* 7:535-547.
2. Yosipovitch, G., Greaves, M. W., and Schmelz, M. 2003. Itch. *Lancet* 361:690-694.
3. Bieber, T. 2008. Atopic dermatitis. *N. Engl. J. Med.* 358:1483-1494.
4. Yamaoka, H., Sasaki, H., Yamasaki, H., Ogawa, K., Ohta, T., Furuta, H., Nishi, M., and Nanjo, K. 2010. Truncal pruritus of unknown origin may be a symptom of diabetic polyneuropathy. *Diabetes Care* 33:150-155.
5. Kremer, A. E., Martens, J. J., Kulik, W., Rueff, F., Kuiper, E. M., van Buuren, H. R., van Erpecum, K. J., Kondrackiene, J., Prieto, J., Rust, C. et al 2010. Lysophosphatidic acid is a potential mediator of cholestatic pruritus. *Gastroenterology* 139:1008-18, 1018.
6. Davidson, S., Zhang, X., Khasabov, S. G., Simone, D. A., and Giesler, G. J., Jr. 2009. Relief of itch by scratching: state-dependent inhibition of primate spinothalamic tract neurons. *Nat. Neurosci.* 12:544-546.
7. Paus, R., Schmelz, M., Biro, T., and Steinhoff, M. 2006. Frontiers in pruritus research: scratching the brain for more effective itch therapy. *J. Clin. Invest* 116:1174-1186.
8. Yosipovitch, G., Carstens, E., and McGlone, F. 2007. Chronic itch and chronic pain: Analogous mechanisms. *Pain* 131:4-7.
9. Sun, Y. G., and Chen, Z. F. 2007. A gastrin-releasing peptide receptor mediates the itch sensation in the spinal cord. *Nature* 448:700-703.
10. Sun, Y. G., Zhao, Z. Q., Meng, X. L., Yin, J., Liu, X. Y., and Chen, Z. F. 2009. Cellular basis of itch sensation. *Science* 325:1531-1534.
11. Liu, Q., Tang, Z., Surdenikova, L., Kim, S., Patel, K. N., Kim, A., Ru, F., Guan, Y., Weng, H. J., Geng, Y. et al 2009. Sensory neuron-specific GPCR Mrgprs are itch receptors mediating chloroquine-induced pruritus. *Cell* 139:1353-1365.
12. Davidson, S., Zhang, X., Yoon, C. H., Khasabov, S. G., Simone, D. A., and Giesler, G. J., Jr. 2007. The itch-producing agents histamine and cowhage activate separate populations of primate spinothalamic tract neurons. *J. Neurosci.* 27:10007-10014.
13. Shim, W. S., and Oh, U. 2008. Histamine-induced itch and its relationship with pain. *Mol. Pain.* 4:29.
14. Han, S. K., Mancino, V., and Simon, M. I. 2006. Phospholipase Cbeta 3 mediates the scratching response activated by the histamine H1 receptor on C-fiber nociceptive neurons. *Neuron* 52:691-703.
15. Imamachi, N., Park, G. H., Lee, H., Anderson, D. J., Simon, M. I., Basbaum, A. I., and Han, S. K. 2009. TRPV1-expressing primary afferents generate behavioral responses to pruritogens via multiple mechanisms. *Proc. Natl. Acad. Sci. U.S.A* 106:11330-11335.
16. Rossbach, K., Nassenstein, C., Gschwandtner, M., Schnell, D., Sander, K., Seifert, R., Stark, H., Kietzmann, M., and Baumer, W. 2011. Histamine H(1), H(3) and H(4) receptors are involved in pruritus. *Neuroscience*.
17. Wilson, S. R., Gerhold, K. A., Bifolck-Fisher, A., Liu, Q., Patel, K. N., Dong, X., and Bautista, D. M. 2011. TRPA1 is required for histamine-independent, Mas-related G protein-coupled receptor-mediated itch. *Nat. Neurosci.* 14:595-602.
18. Mishra, S. K., Tisel, S. M., Orestes, P., Bhangoo, S. K., and Hoon, M. A. 2011. TRPV1-lineage neurons are required for thermal sensation. *EMBO J.* 30:582-593.
19. Lagerstrom, M. C., Rogoz, K., Abrahamsen, B., Persson, E., Reinius, B., Nordenankar, K., Olund, C., Smith, C., Mendez, J. A., Chen, Z. F. et al 2010. VGLUT2-dependent sensory neurons in the TRPV1 population regulate pain and itch. *Neuron* 68:529-542.
20. Liu, Y., Abdel, S. O., Zhang, L., Duan, B., Tong, Q., Lopes, C., Ji, R. R., Lowell, B. B., and Ma, Q. 2010. VGLUT2-dependent glutamate release from nociceptors is required to sense pain and suppress itch. *Neuron* 68:543-556.
21. Ross, S. E., Mardinly, A. R., McCord, A. E., Zurawski, J., Cohen, S., Jung, C., Hu, L., Mok, S. I., Shah, A., Savner, E. M. et al 2010. Loss of inhibitory interneurons in the dorsal spinal cord and elevated itch in Bhlhb5 mutant mice. *Neuron* 65:886-898.

22. Akira, S., Uematsu, S., and Takeuchi, O. 2006. Pathogen recognition and innate immunity. *Cell* 124:783-801.
23. Kawai, T., and Akira, S. 2010. The role of pattern-recognition receptors in innate immunity: update on Toll-like receptors. Nat. Immunol. 11:373-384.
24. Wang, T., Town, T., Alexopoulou, L., Anderson, J. F., Fikrig, E., and Flavell, R. A. 2004. Toll-like receptor 3 mediates West Nile virus entry into the brain causing lethal encephalitis. *Nat. Med.* 10:1366-1373.
25. Town, T., Jeng, D., Alexopoulou, L., Tan, J., and Flavell, R. A. 2006. Microglia recognize double-stranded RNA via TLR3. *J. Immunol.* 176:3804-3812.
26. Heil, F., Hemmi, H., Hochrein, H., Ampenberger, F., Kirschning, C., Akira, S., Lipford, G., Wagner, H., and Bauer, S. 2004. Species-specific recognition of single-stranded RNA via toll-like receptor 7 and 8. *Science* 303: 1526-1529.
27. Lund, J. M., Alexopoulou, L., Sato, A., Karow, M., Adams, N. C., Gale, N. W., Iwasaki, A., and Flavell, R. A. 2004. Recognition of single-stranded RNA viruses by Toll-like receptor 7. *Proc. Natl. Acad. Sci. U.S.A* 101:5598-5603.
28. Kim, D., Kim, M. A., Cho, I. H., Kim, M. S., Lee, S., Jo, E. K., Choi, S. Y., Park, K., Kim, J. S., Akira, S. et al 2007. A critical role of toll-like receptor 2 in nerve injury-induced spinal cord glial cell activation and pain hypersensitivity. *J. Biol. Chem.* 282:14975-14983.
29. Obata, K., Katsura, H., Miyoshi, K., Kondo, T., Yamanaka, H., Kobayashi, K., Dai, Y., Fukuoka, T., Akira, S., and Noguchi, K. 2008. Toll-like receptor 3 contributes to spinal glial activation and tactile allodynia after nerve injury. J. *Neurochem.* 105:2249-2259.
30. Tanga, F. Y., Nutile-McMenemy, N., and Deleo, J. A. 2005. The CNS role of Toll-like receptor 4 in innate neuroimmunity and painful neuropathy. *Proc. Natl. Acad. Sci. U.S.A* 102:5856-5861.
31. Wadachi, R., and Hargreaves, K. M. 2006. Trigeminal nociceptors express TLR-4 and CD14: a mechanism for pain due to infection. *J. Dent. Res.* 85:49-53.
32. Diogenes, A., Ferraz, C. C., Akopian, A. N., Henry, M. A., and Hargreaves, K. M. 2011. LPS sensitizes TRPV1 via activation of TLR4 in trigeminal sensory neurons. *J. Dent. Res.* 90:759-764.
33. Cameron, J. S., Alexopoulou, L., Sloane, J. A., DiBernardo, A. B., Ma, Y., Kosaras, B., Flavell, R., Strittmatter, S. M., Volpe, J., Sidman, R. et al 2007. Toll-like receptor 3 is a potent negative regulator of axonal growth in mammals. *J. Neurosci.* 27:13033-13041.
34. Liu, T., Xu, Z. Z., Park, C. K., Berta, T., and Ji, R. R. 2010. Toll-like receptor 7 mediates pruritus. *Nat. Neurosci.* 13:1460-1462.
35. Ji, R. R., Kohno, T., Moore, K. A., and Woolf, C. J. 2003. Central sensitization and LTP: do pain and memory share similar mechanisms? *Trends Neurosci.* 26:696-705.
36. Patel, K. N., and Dong, X. 2010. An itch to be scratched. *Neuron* 68:334-339.
37. Ruscheweyh, R., Wilder-Smith, O., Drdla, R., Liu, X. G., and Sandkuhler, J. 2011. Long-term potentiation in spinal nociceptive pathways as a novel target for pain therapy. *Mol. Pain.* 7:20.
38. Schwartz, E. S., Kim, H. Y., Wang, J., Lee, I., Klann, E., Chung, J. M., and Chung, K. 2009. Persistent pain is dependent on spinal mitochondrial antioxidant levels. *J. Neurosci.* 29:159-168.
39. Alexopoulou, L., Holt, A. C., Medzhitov, R., and Flavell, R. A. 2001. Recognition of double-stranded RNA and activation of NF-kappaB by Toll-like receptor 3. *Nature* 413: 732-738.
40. Akiyama, T., Merrill, A. W., Carstens, M. I., and Carstens, E. 2009. Activation of superficial dorsal horn neurons in the mouse by a PAR-2 agonist and 5-HT: potential role in itch. *J. Neurosci.* 29:6691-6699.
41. Steinhoff, M., Neisius, U., Ikoma, A., Fartasch, M., Heyer, G., Skov, P. S., Luger, T. A., and Schmelz, M. 2003. Proteinase-activated receptor-2 mediates itch: a novel pathway for pruritus in human skin. *J. Neurosci.* 23:6176-6180.
42. Liu, Q., Weng, H. J., Patel, K. N., Tang, Z., Bai, H., Steinhoff, M., and Dong, X. 2011. The Distinct Roles of Two GPCRs, MrgprC11 and PAR2, in Itch and Hyperalgesia. *Sci. Signal.* 4:ra45.
43. Kim, S. J., Park, G. H., Kim, D., Lee, J., Min, H., Wall, E., Lee, C. J., Simon, M. I., Lee, S. J., and Han, S. K. 2011. Analysis of cellular and behavioral responses to imiquimod reveals a unique itch pathway in transient receptor potential vanilloid 1 (TRPV1)-expressing neurons. *Proc. Natl. Acad. Sci. U.S.A* 108:3371-3376.
44. Shimada, S. G., and LaMotte, R. H.2008. Behavioral differentiation between itch and pain in mouse. *Pain* 139: 681-687.
45. Akiyama, T., Carstens, M. I., and Carstens, E. 2010. Facial injections of pruritogens and algogens excite partly overlapping populations of primary and second-order trigeminal neurons in mice. *J. Neurophysiol.* 104:2442-2450.
46. Cameron, J. S., Alexopoulou, L., Sloane, J. A., DiBernardo, A. B., Ma, Y., Kosaras, B., Flavell, R., Strittmatter, S. M., Volpe, J., Sidman, R. et al 2007. Toll-like receptor 3 is a potent negative regulator of axonal growth in mammals. *J. Neurosci.* 27:13033-13041.
47. Kawasaki, Y. 2008. Cytokine mechanisms of central sensitization: distinct and overlapping role of interleukin-1beta, interleukin-6, and tumor necrosis factor-alpha in regulating synaptic and neuronal activity in the superficial spinal cord.
48. Toshchakov, V. U., Basu, S., Fenton, M. J., and Vogel, S. N. 2005. Differential involvement of BB loops of toll-IL-1 resistance (TIR) domain-containing adapter proteins in. *J. Immunol.* 175:494-500.
49. Miyamoto, T., Nojima, H., Shinkado, T., Nakahashi, T., and Kuraishi, Y. 2002. Itch-associated response induced by experimental dry skin in mice. *Jpn. J. Pharmacol.* 88:285-292.
50. Akiyama, T., Carstens, M. I., and Carstens, E. 2010. Enhanced scratching evoked by PAR-2 agonist and 5-HT but not histamine in a mouse model of chronic dry skin itch. *Pain* 151:378-383.
51. Shimada, S. G., and LaMotte, R. H.2008. Behavioral differentiation between itch and pain in mouse. *Pain* 139: 681-687.
52. Okun, E., Griffioen, K., Barak, B., Rob erts, N. J., Castro, K., Pita, M. A., Cheng, A., Mughal, M. R., Wan, R., Ashery, U. et al 2010. Toll-like receptor 3 inhibits memory retention and constrains adult hippocampal neurogenesis. *Proc. Natl. Acad. Sci. U.S.A* 107:15625-15630.
53. Ma, Q. 2010. Labeled lines meet and talk: population coding of somatic sensations. *J. Clin. Invest* 120:3773-3778.

Other Embodiments

It is to be understood that while the invention has been described in conjunction with the detailed description thereof, the foregoing description is intended to illustrate and not limit the scope of the invention, which is defined by the scope of the appended claims. Other aspects, advantages, and modifications are within the scope of the following claims.

What is claimed is:

1. A method of reducing pruritus in a subject, the method comprising administering to the subject a therapeutically effective amount of a toll-like receptor (TLR) 3 or TLR7 inhibitor, thereby reducing pruritus in the subject.

2. The method of claim 1, wherein the method comprises administering to the subject a therapeutically effective amount of a TLR3 inhibitor.

3. The method of claim 2, wherein the TLR3 inhibitor is an anti-TLR3 antibody or an antigen-binding fragment thereof.

4. The method of claim 2, wherein the TLR3 inhibitor is an inhibitory nucleic acid effective to specifically reduce expression of TLR3.

5. The method of claim 4, wherein the inhibitory nucleic acid is a small interfering RNA molecule or antisense nucleic acid.

6. The method of claim 2, wherein the TLR3 inhibitor is a small molecule.

7. The method of claim 1, wherein method comprises administering to the subject a therapeutically effective amount of a TLR7 inhibitor.

8. The method of claim 7, wherein the TLR7 inhibitor is an anti-TLR7 antibody or an antigen-binding fragment thereof.

9. The method of claim 7, wherein the TLR7 inhibitor is an inhibitory nucleic acid effective to specifically reduce expression of TLR7.

10. The method of claim 9, wherein the inhibitory nucleic acid is a small interfering RNA molecule or antisense nucleic acid.

11. The method of claim 7, wherein the TLR7 inhibitor is a small molecule.

12. The method of claim 1, wherein the subject has, or is at risk of developing, pruritus.

13. The method of claim 1, wherein the subject has atopic dermatitis, psoriasis, renal disease, or liver disease.

14. The method of claim 1, wherein the subject is infected with a virus.

15. The method of claim 14, wherein the virus is human immunodeficiency virus or varicella zoster virus.

16. The method of claim 1, wherein the subject is being treated with chloroquine.

17. The method of claim 1, wherein the subject is a black African.

18. The method of claim 1, wherein the subject is a mammal.

19. The method of claim 1, wherein the subject is a human.

20. The method of claim 1, wherein administration is topical.

* * * * *